(12) United States Patent
Kang et al.

(10) Patent No.: US 9,139,812 B2
(45) Date of Patent: Sep. 22, 2015

(54) CD49F PROMOTING PROLIFERATION, MULTIPOTENCY AND REPROGRAMMING OF ADULT STEM CELLS THROUGH PI3K/AKT/GSK3 PATHWAY

(75) Inventors: Kyung Sun Kang, Seoul (KR); Kyung Rok Yu, Seoul (KR)

(73) Assignee: KANG STEM HOLDINGS CO., LTD, Seoul (KR)

(*) Notice: Subject to any disclaimer, the term of this patent is extended or adjusted under 35 U.S.C. 154(b) by 0 days.

(21) Appl. No.: 13/638,262

(22) PCT Filed: Feb. 18, 2011

(86) PCT No.: PCT/KR2011/001103
§ 371 (c)(1),
(2), (4) Date: Dec. 10, 2012

(87) PCT Pub. No.: WO2011/102680
PCT Pub. Date: Aug. 25, 2011

(65) Prior Publication Data
US 2013/0089885 A1     Apr. 11, 2013

(30) Foreign Application Priority Data
Feb. 18, 2010   (KR) .................... 10-2010-0014771

(51) Int. Cl.
| C12N 5/071 | (2010.01) |
| C12Q 1/24 | (2006.01) |
| G01N 33/50 | (2006.01) |
| C12N 5/0775 | (2010.01) |
| A61K 35/12 | (2015.01) |

(52) U.S. Cl.
CPC ............ *C12N 5/0602* (2013.01); *C12N 5/0663* (2013.01); *C12N 5/0665* (2013.01); *C12N 5/0667* (2013.01); *C12Q 1/24* (2013.01); *G01N 33/5073* (2013.01); *A61K 2035/124* (2013.01); *G01N 2333/7055* (2013.01)

(58) Field of Classification Search
None
See application file for complete search history.

(56) References Cited

U.S. PATENT DOCUMENTS
2006/0205075 A1   9/2006   Nakatsuji et al.

FOREIGN PATENT DOCUMENTS
| WO | 2004/020597 A2 | 11/2004 |
| WO | 2009/154770 A2 | 12/2009 |

OTHER PUBLICATIONS

Xin et al. "Self-Renewal and Multilineage Differentiation In Vitro from Murine Prostate Stem Cells." Stem Cells vol. 25, pp. 2760-2769, 2007.*
Xin et al. Supplemental (A) 2007 Stem Cells vol. 25, pp. 1-3.*
Xin et al.. Supplemental (B) 2007 Stem Cells vol. 25, pp. 1.*
Shi et al. "Anchorage-independent culture maintains prostate stem cells." Developmental Biology vol. 312, pp. 396-406, 2007.*
Coutu et al. "Roles of FGF signaling in stem cell self-renewal, senescence and aging." Aging. (Oct. 2011);3(10):pp. 920-933.*
Zhang et al. "Maintenance of high proliferation and multipotent potential of human hair follicle-derived mesenchymal stem cells by growth factors." International Journal of Molecular Medicine International Journal of Molecular Medicine. (2013); 31(4): pp. 913-921.*
Dragoo et al., "Tissue-engineered cartilage and bone using stem cells from human infrapatellar fat pads," J Bone Joint Surg [Br] 85-B: 740-747, 2003.
Erickson et al., "Chondrogenic Potential of Adipose Tissue-Derived Stromal Cells in Vitro and in Vivo," Biochemical and Biophysical Research Communications 290: 763-769, 2002.
Halvorsen et al., "Extracellular Matrix Mineralization and Osteoblast Gene Expression by Human Adipose Tissue-Derived Stromal Cells," Tissue Engineering 7(6): 729-741, 2001.
Jin Sup Jung, "Adipose Tissue Derived Mesenchymal Stem Cells," J Korean Soc Transplant 22: 183-196, 2008.
Klinowska et al., "Epithelial Development and Differentiation in the Mammary Gland Is Not Dependent on alpha3 or alpha6 IntegrinSubunits," Developmental Bioloy 233: 449-467, 2001.
Lawson et al., "Isolation and functional characterization of murine prostate stem cells," PNAS 104(1): 181-186, Jan. 2, 2007.
Lee et al., "The CD34-like protein PODXL and alpha6-integrin (CD49f) identify early progenitor MSCs with increased clonogeneicity and migration to infarcted heart in mice," Blood 113: 816-826, 2009.
Notta et al., "Isolation of Single Human Hematopoietic Stem Cells Capable of Long-Term Multilineage Engraftment," Science 333: 218-221, Jul. 8, 2011.
Stingl et al., "Purification and unique properties of mammary epithelial stem cells," Nature 439: 993-997, Feb. 23, 2006.
Toma et al., "Isolation of multipotent adult stem cells from the dermis of mammalian skin," Nature Cell Biology 3: 778-784, Sep. 2001.
Woodward et al., "On mammary stem cells," Journal of Cell Science 118(16): 3585-3594, 2005.
Yuan Jing et al., "3-D spheroid culture of bone marrow mesenchymal stem cell of rhesus monkey with improved multi-differentiation potential to epithelial progenitors and neuron in vitro," Clinical and Experimental Ophthalmology 39: 808-819, 2011.

* cited by examiner

Primary Examiner — Thaian N Ton
Assistant Examiner — Titilayo Moloye
(74) Attorney, Agent, or Firm — Cooley LLP

(57) ABSTRACT

The present invention relates to a method for obtaining adult stem cells, which have a surface antigen of CD49f, excellent formation of spheres due to sphere formation and high expression of OCT4 and SOX2, from a cell source including stem cells, and a cell therapeutic agent containing adult stem cells obtained by the method or cells differentiated therefrom as an active ingredient.
According to the present invention, adult stem cells derived from spheres are suitable for mass culture of adult stem cells because of more rapid growth thereof compared with stem cells obtained by a known adhesive culture method, have a specific surface antigen so as to be homogeneously obtained by using the specific surface antigen, and are useful for preparing a cell therapeutic agent using the same because of excellent differentiation thereof.

16 Claims, 39 Drawing Sheets

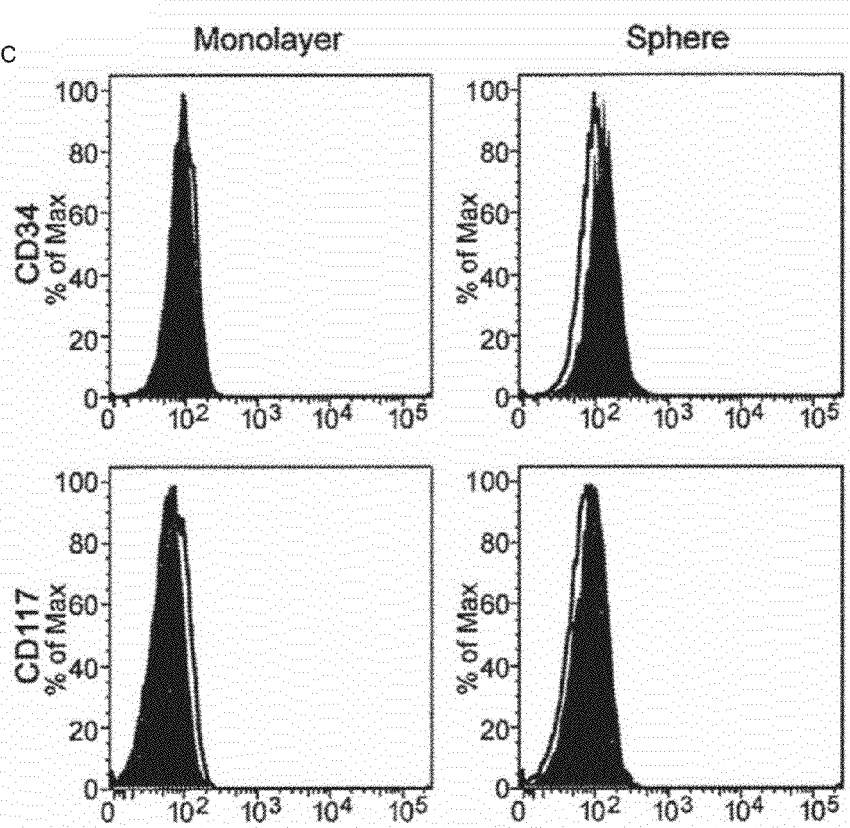

Figure 4E
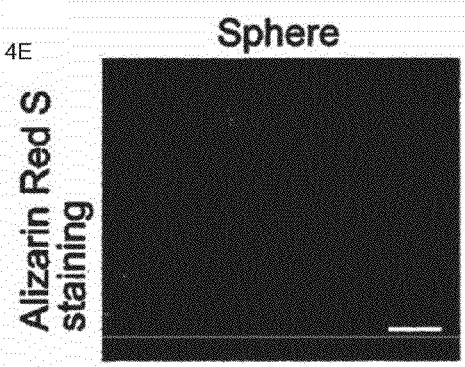
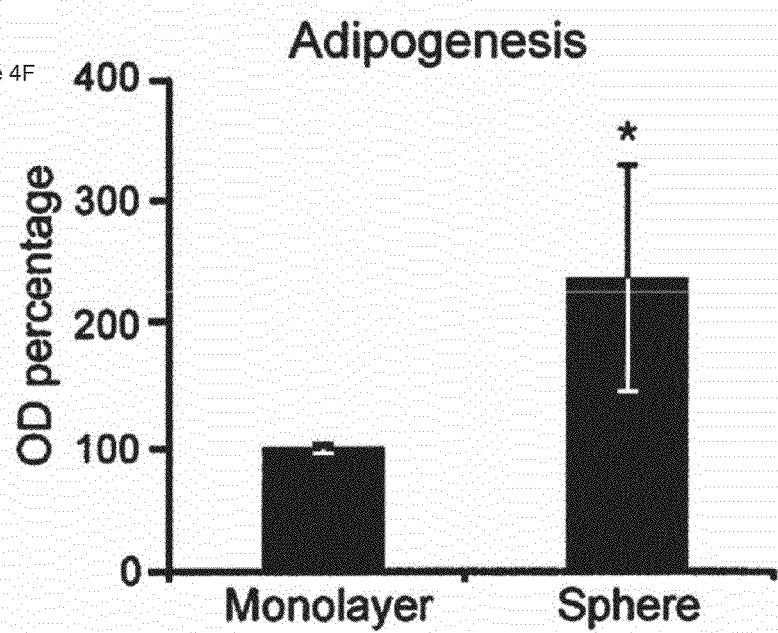

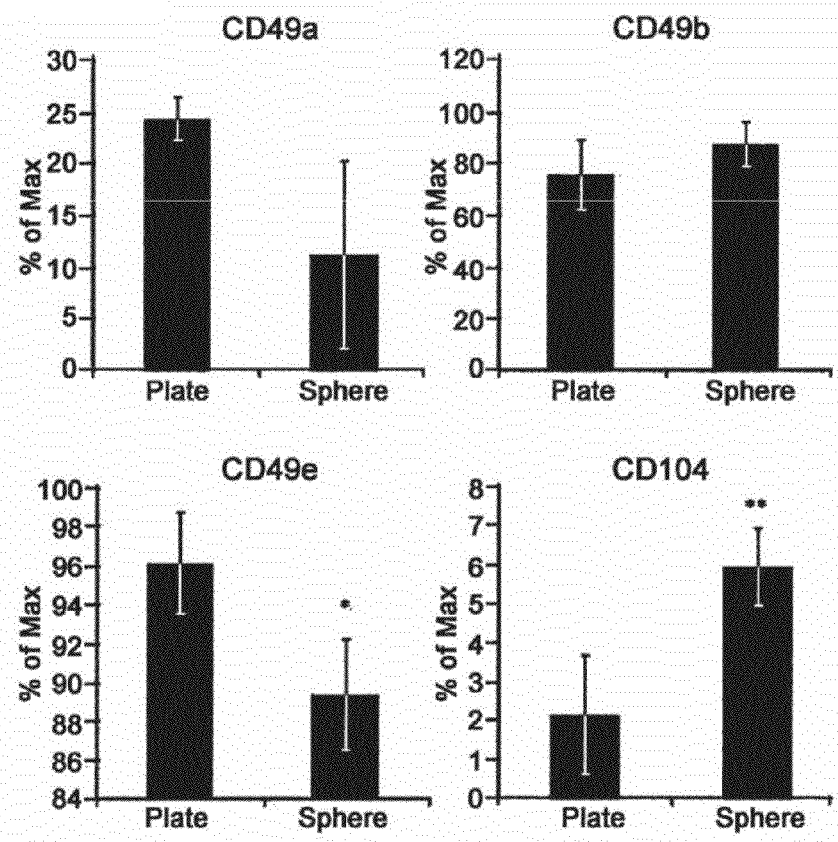

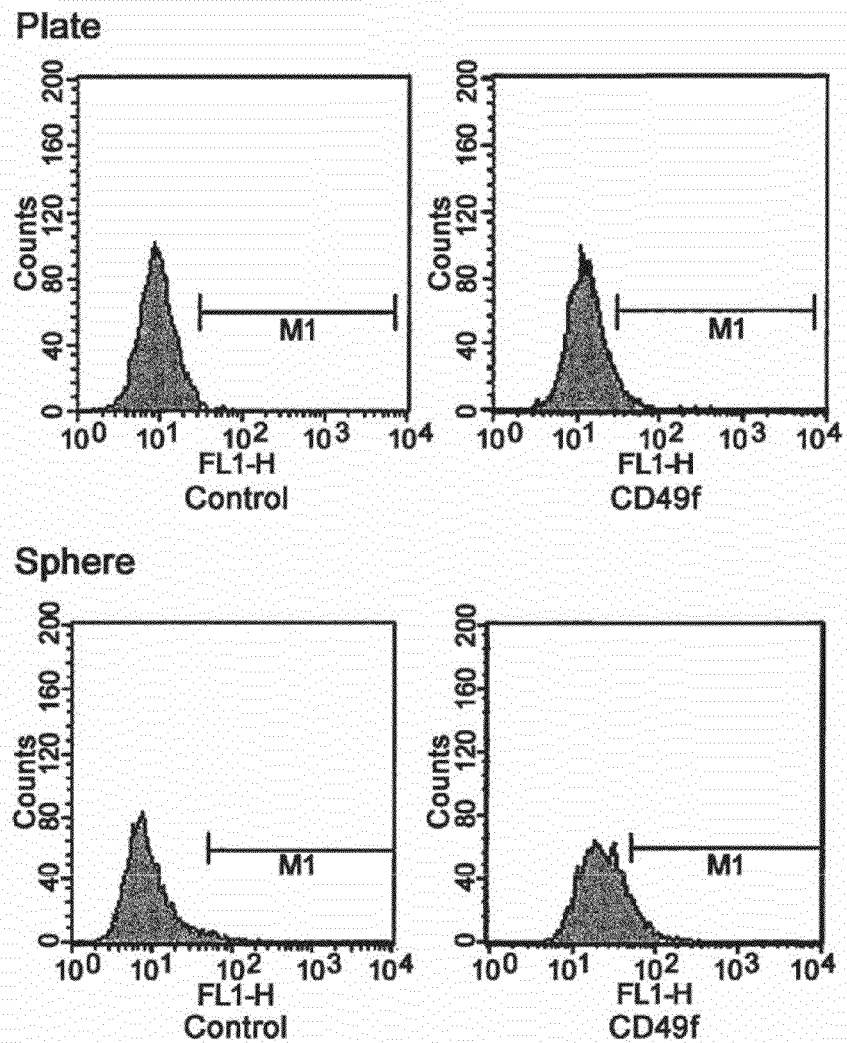

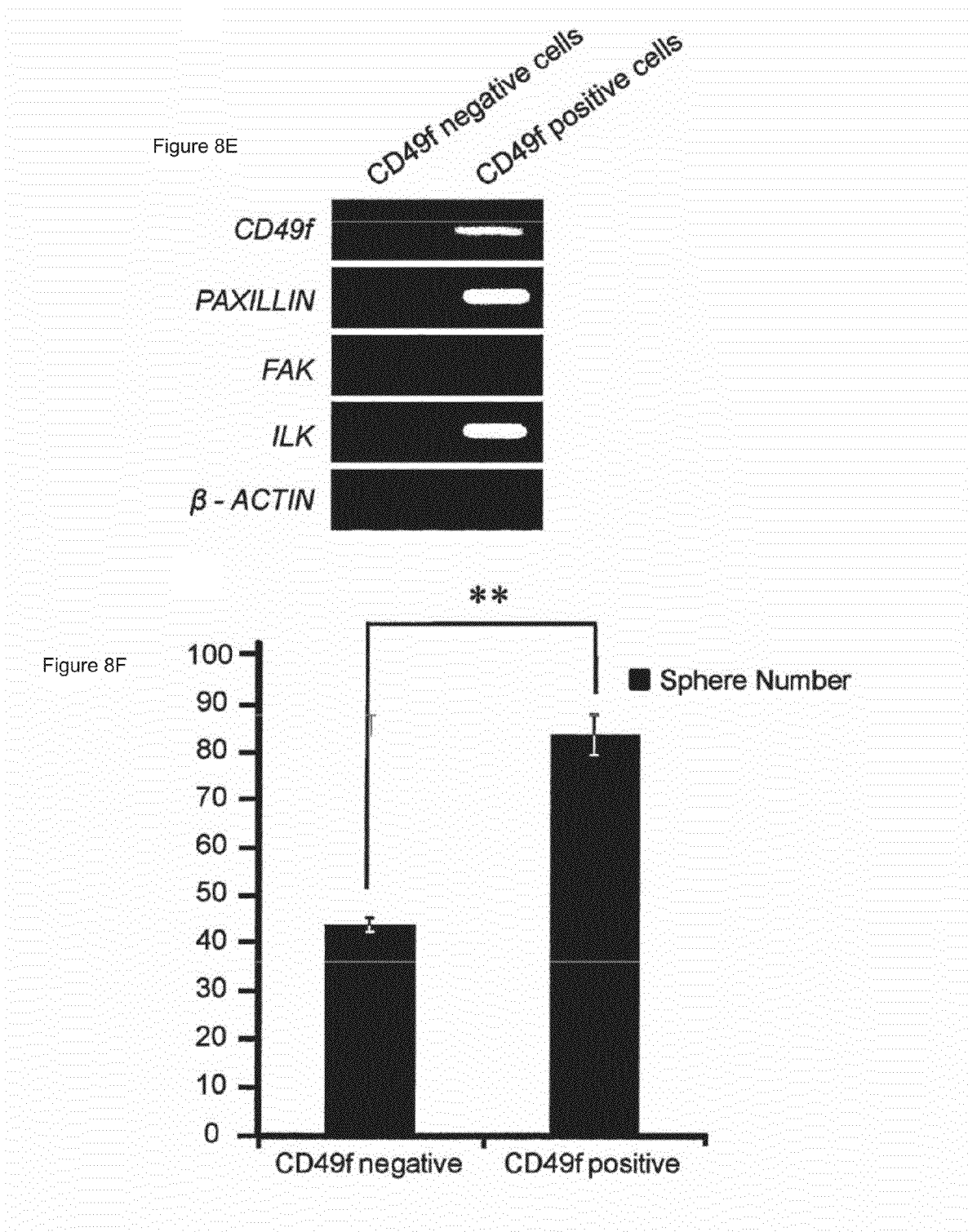

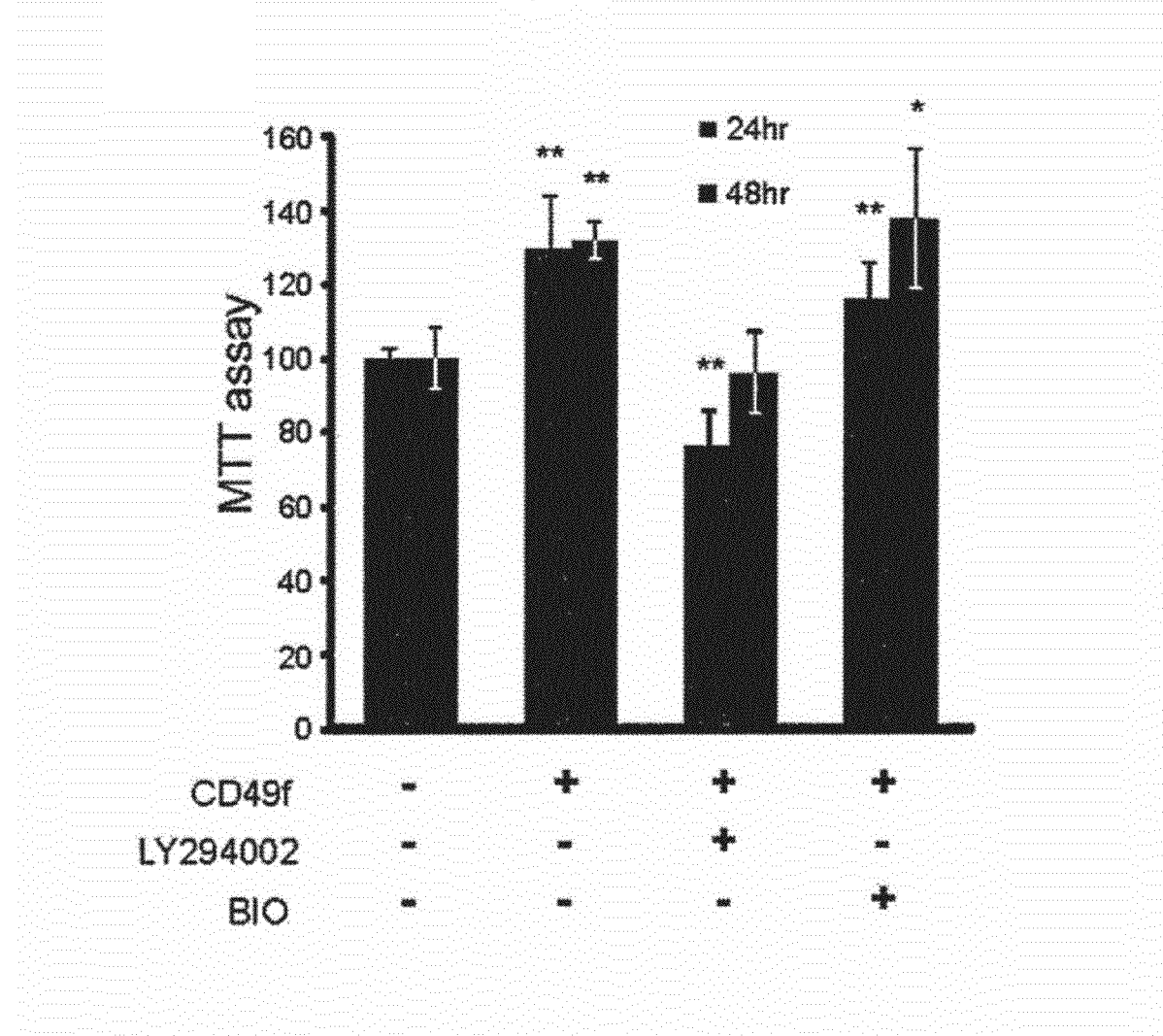

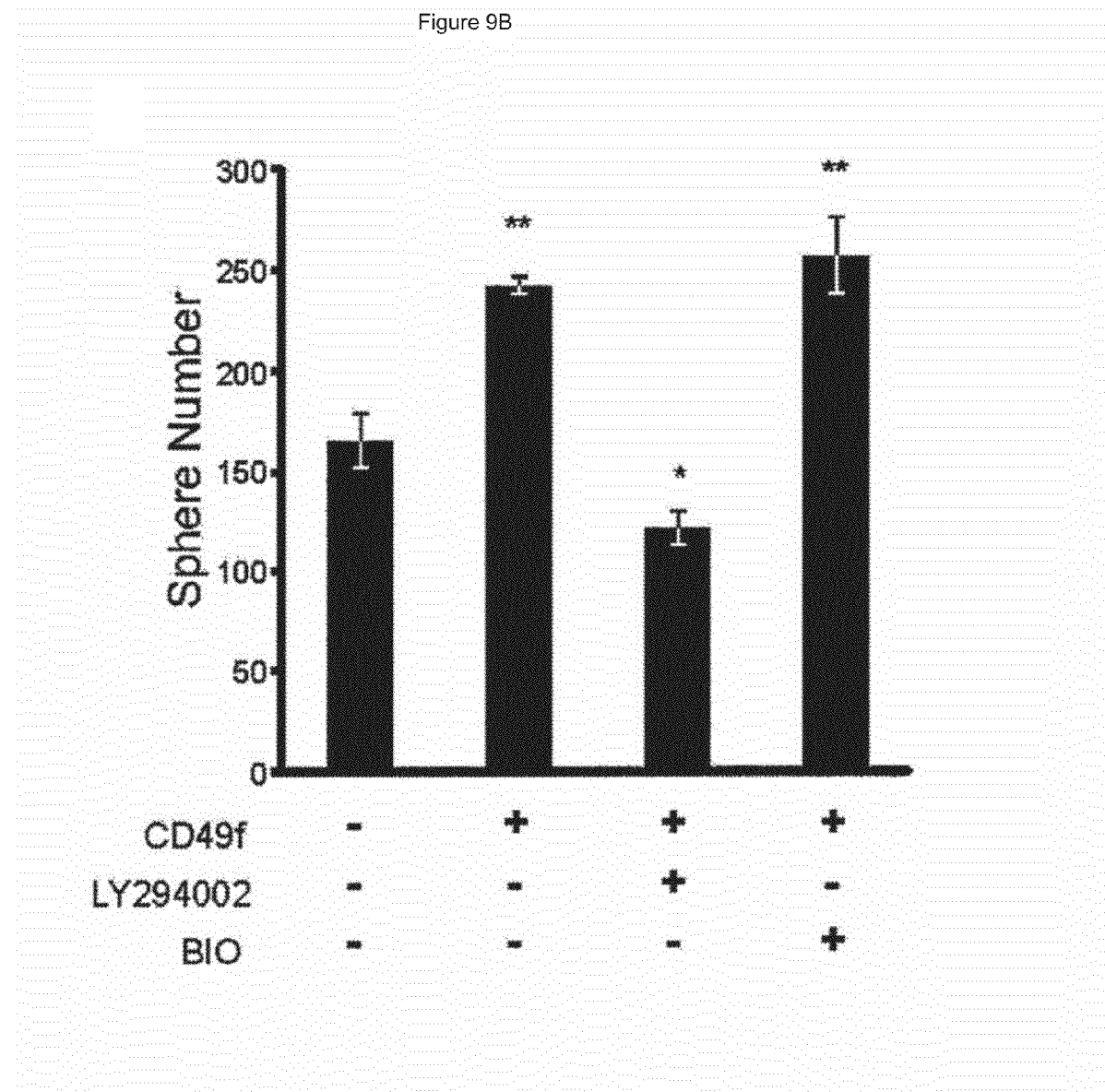

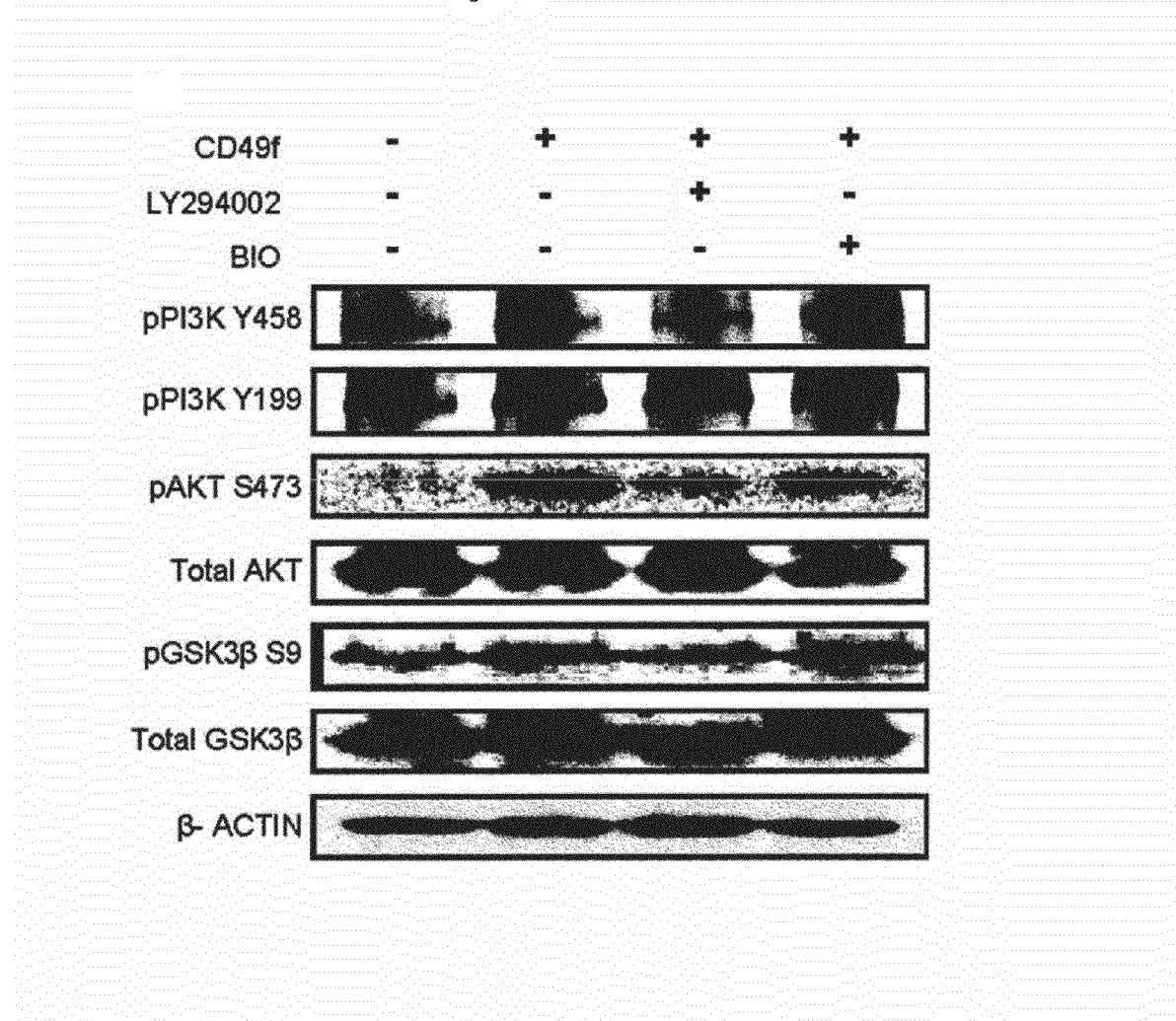

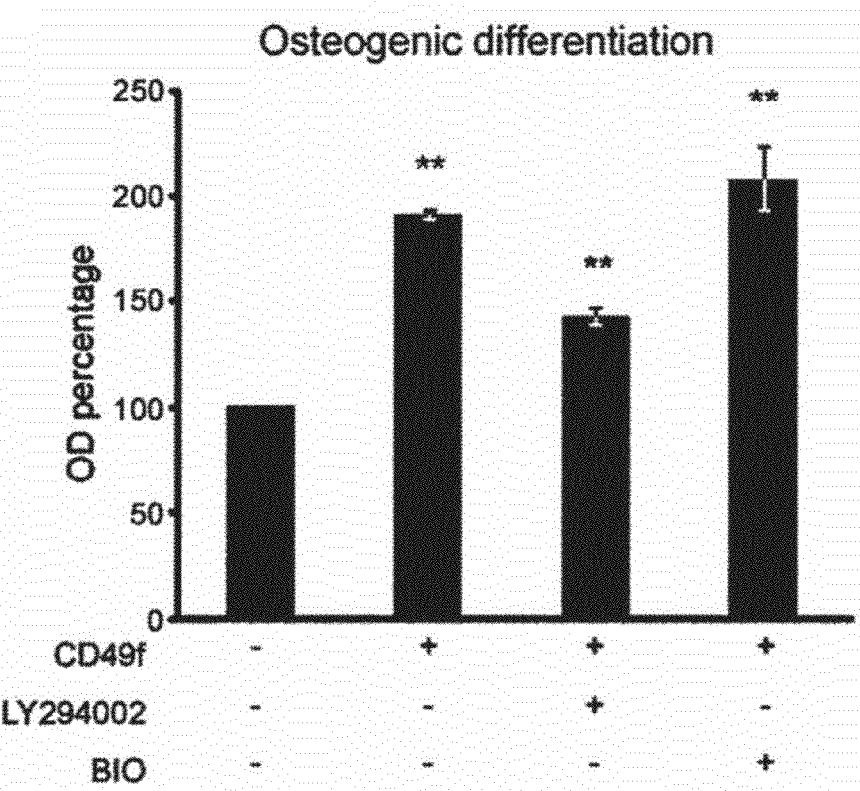

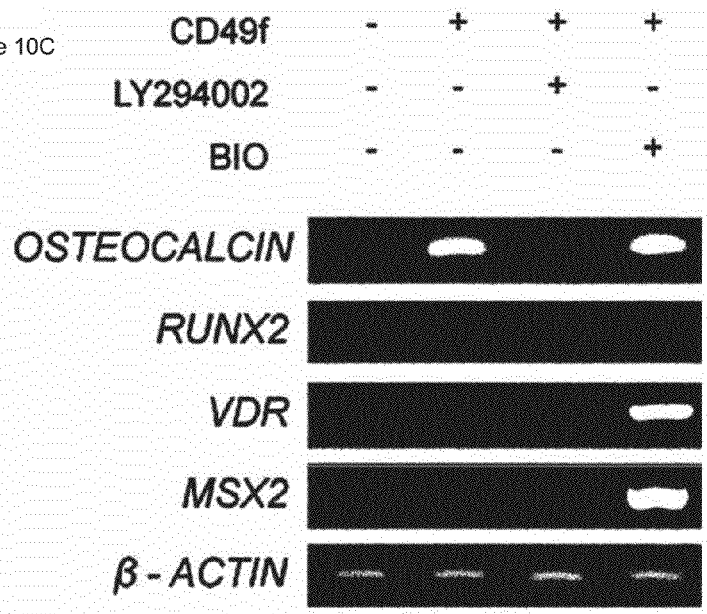
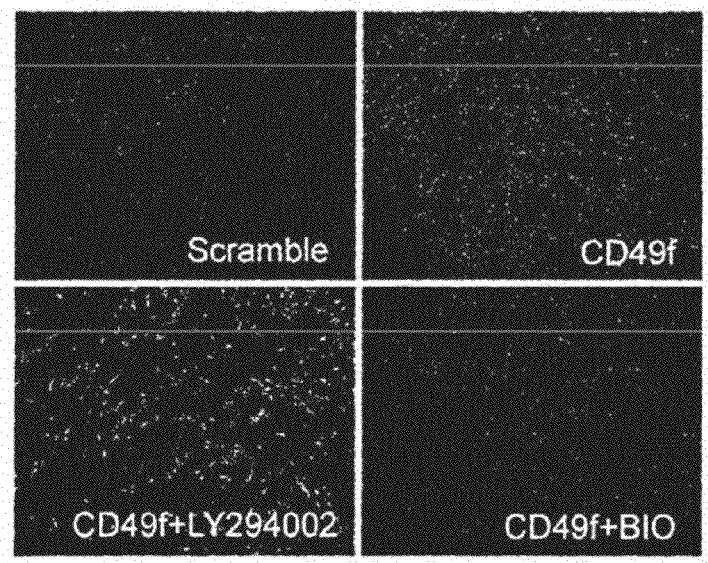

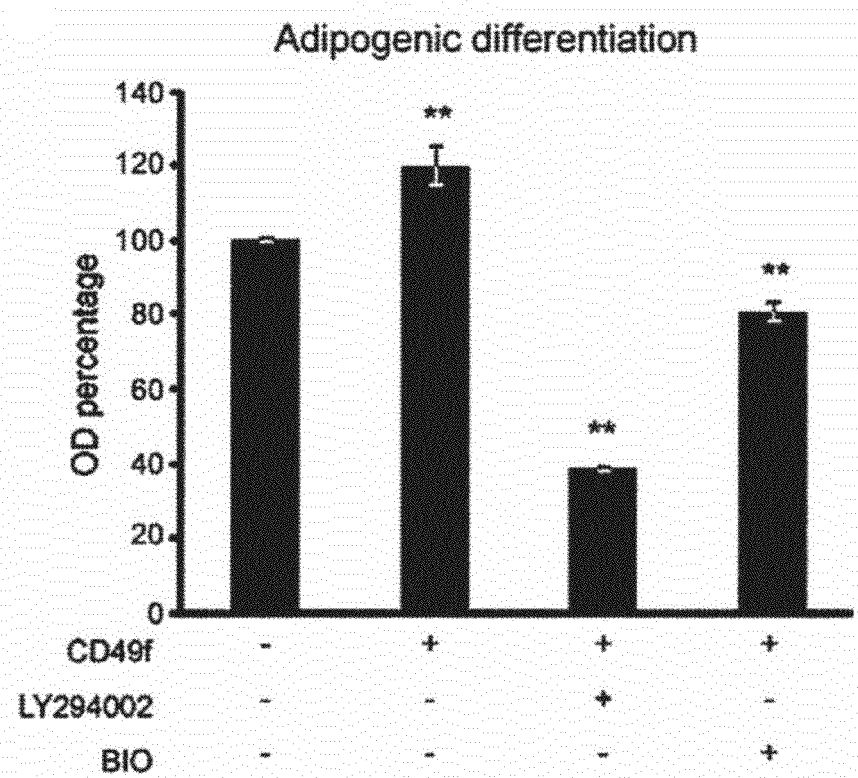

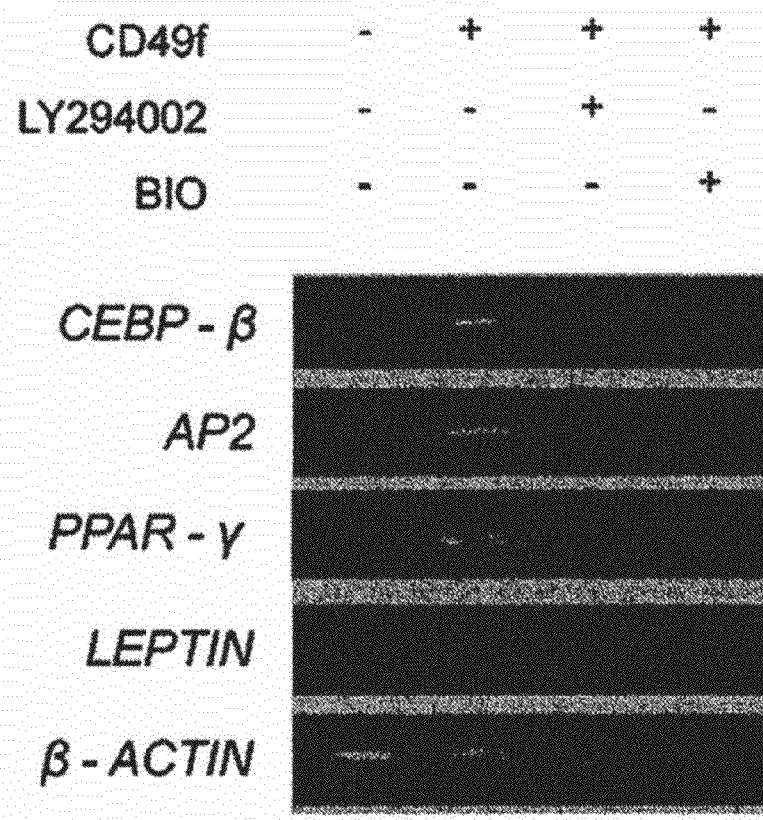

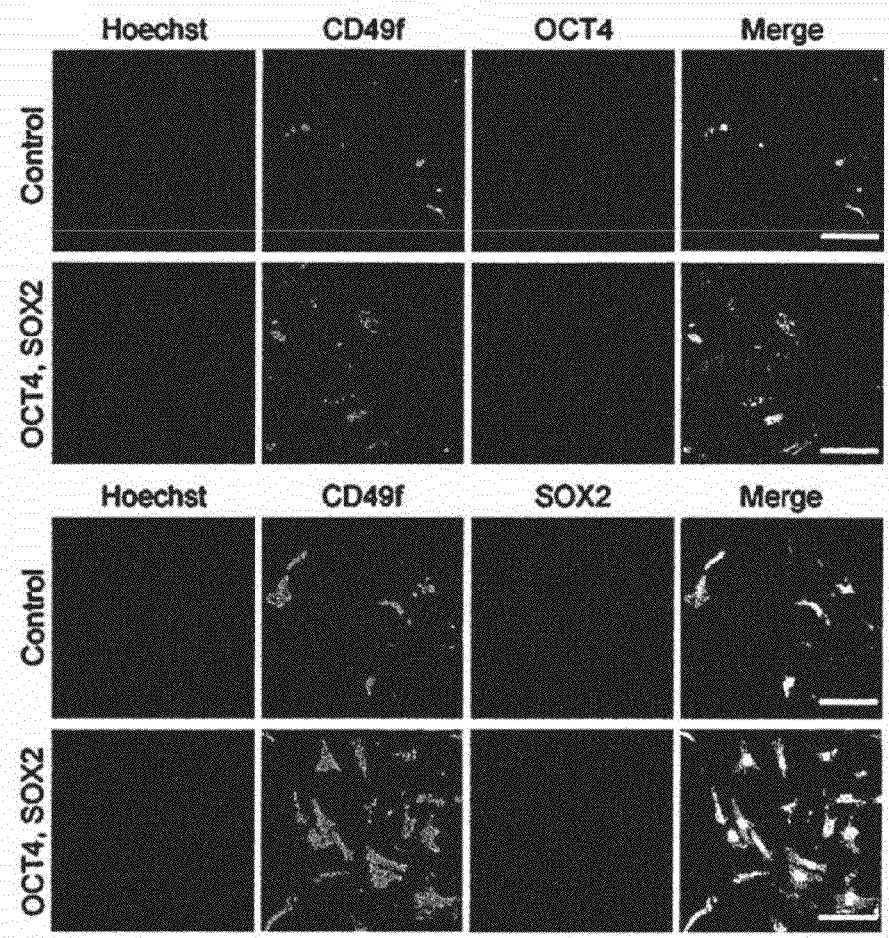

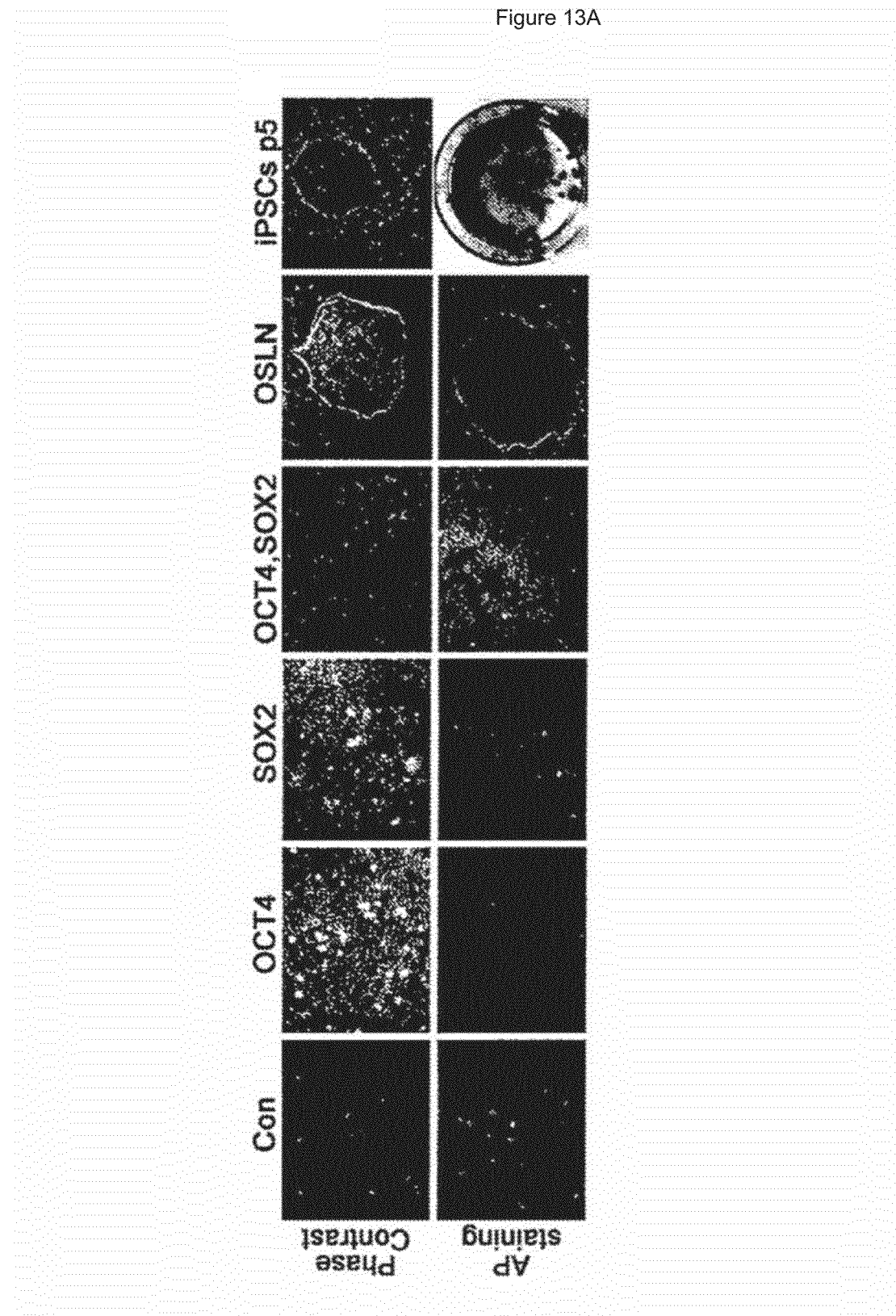

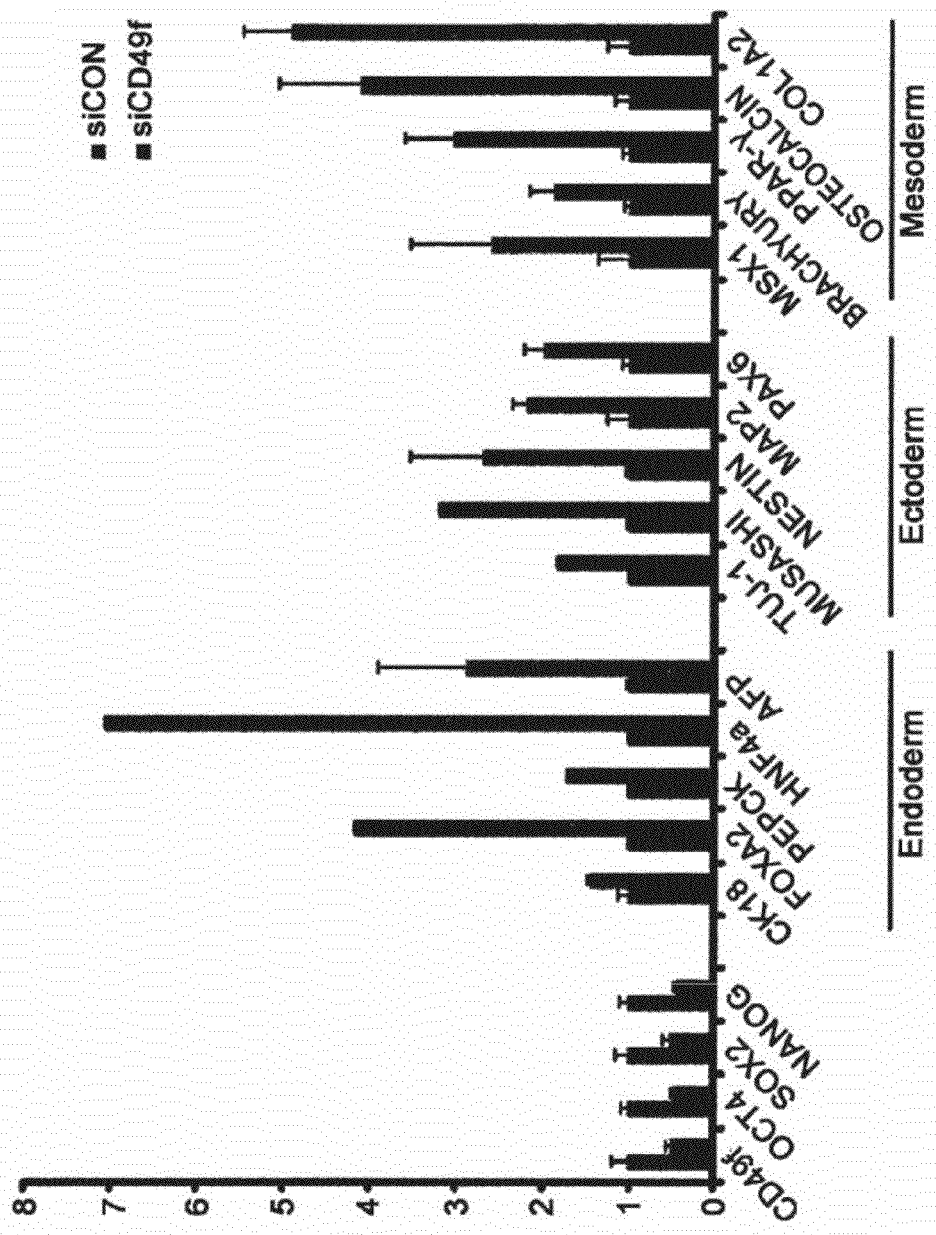

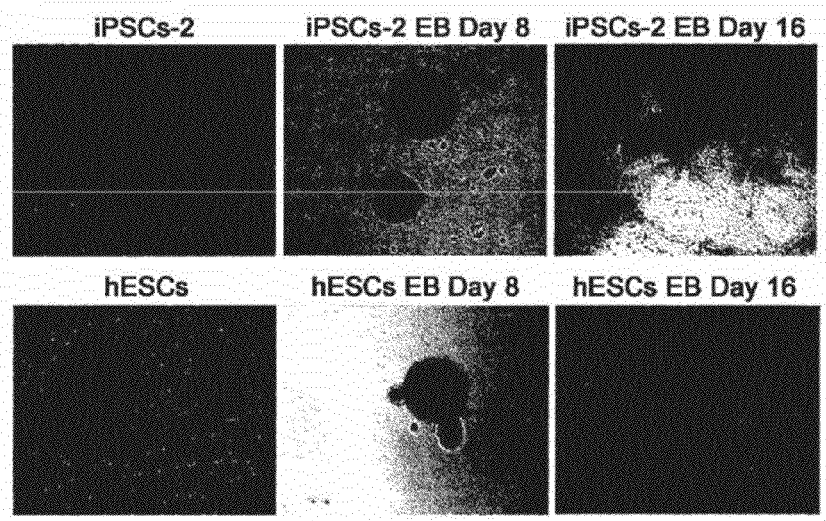
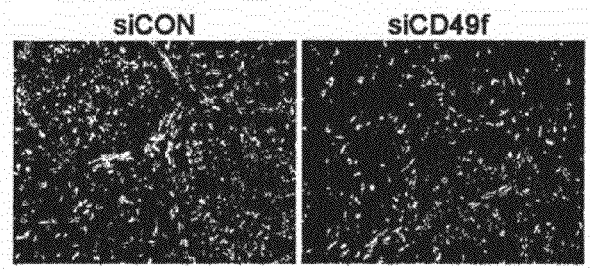

SEQUENCE LISTING

<160> NUMBER OF SEQ ID NOS: 76

<210> SEQ ID NO 1
<211> LENGTH: 20
<212> TYPE: DNA

```
<213> ORGANISM: Artificial Sequence
<220> FEATURE:
<223> OTHER INFORMATION: Forward primer for beta-actin

<400> SEQUENCE: 1
agagctacga gctgcctgac                                                    20

<210> SEQ ID NO 2
<211> LENGTH: 20
<212> TYPE: DNA
<213> ORGANISM: Artificial Sequence
<220> FEATURE:
<223> OTHER INFORMATION: Reverse primer for beta-actin

<400> SEQUENCE: 2
agcactgtgt tggcgtacag                                                    20

<210> SEQ ID NO 3
<211> LENGTH: 20
<212> TYPE: DNA
<213> ORGANISM: Artificial Sequence
<220> FEATURE:
<223> OTHER INFORMATION: Forward primer for C/EBP-beta

<400> SEQUENCE: 3
gcgcgcttac ctcggctacc                                                    20

<210> SEQ ID NO 4
<211> LENGTH: 20
<212> TYPE: DNA
<213> ORGANISM: Artificial Sequence
<220> FEATURE:
<223> OTHER INFORMATION: Reverse primer for C/EBP-beta

<400> SEQUENCE: 4
tggccttgtc gcggctcttg                                                    20

<210> SEQ ID NO 5
<211> LENGTH: 20
<212> TYPE: DNA
<213> ORGANISM: Artificial Sequence
<220> FEATURE:
<223> OTHER INFORMATION: Forward primer for AP2

<400> SEQUENCE: 5
gggtcacagc accctcctga                                                    20

<210> SEQ ID NO 6
<211> LENGTH: 20
<212> TYPE: DNA
<213> ORGANISM: Artificial Sequence
<220> FEATURE:
<223> OTHER INFORMATION: Reverse primer for AP2

<400> SEQUENCE: 6
ggtttggcca tgccagccac                                                    20

<210> SEQ ID NO 7
<211> LENGTH: 20
<212> TYPE: DNA
<213> ORGANISM: Artificial Sequence
<220> FEATURE:
<223> OTHER INFORMATION: Forward primer for PPAR-gamma

<400> SEQUENCE: 7
cctccgggcc ctggcaaaac                                                    20
```

```
<210> SEQ ID NO 8
<211> LENGTH: 20
<212> TYPE: DNA
<213> ORGANISM: Artificial Sequence
<220> FEATURE:
<223> OTHER INFORMATION: Reverse primer for PPAR-gamma

<400> SEQUENCE: 8
ctcctgcaca gcctccacgg                                          20

<210> SEQ ID NO 9
<211> LENGTH: 20
<212> TYPE: DNA
<213> ORGANISM: Artificial Sequence
<220> FEATURE:
<223> OTHER INFORMATION: Forward primer for LEPTIN

<400> SEQUENCE: 9
gaagaccaca tccacacacg                                          20

<210> SEQ ID NO 10
<211> LENGTH: 20
<212> TYPE: DNA
<213> ORGANISM: Artificial Sequence
<220> FEATURE:
<223> OTHER INFORMATION: Reverse primer for LEPTIN

<400> SEQUENCE: 10
agctcagcca gacccatcta                                          20

<210> SEQ ID NO 11
<211> LENGTH: 20
<212> TYPE: DNA
<213> ORGANISM: Artificial Sequence
<220> FEATURE:
<223> OTHER INFORMATION: Forward primer for OSTEOCALCIN

<400> SEQUENCE: 11
cctattggcc ctggccgcac                                          20

<210> SEQ ID NO 12
<211> LENGTH: 20
<212> TYPE: DNA
<213> ORGANISM: Artificial Sequence
<220> FEATURE:
<223> OTHER INFORMATION: Reverse primer for OSTEOCALCIN

<400> SEQUENCE: 12
gacaccctag accgggccgt                                          20

<210> SEQ ID NO 13
<211> LENGTH: 20
<212> TYPE: DNA
<213> ORGANISM: Artificial Sequence
<220> FEATURE:
<223> OTHER INFORMATION: Forward primer for RUNX2

<400> SEQUENCE: 13
cttgaccata accgtcttca                                          20

<210> SEQ ID NO 14
<211> LENGTH: 20
<212> TYPE: DNA
<213> ORGANISM: Artificial Sequence
<220> FEATURE:
```

<223> OTHER INFORMATION: Reverse primer for RUNX2

<400> SEQUENCE: 14
gtcatcaatc ttctgtctgt                                               20

<210> SEQ ID NO 15
<211> LENGTH: 20
<212> TYPE: DNA
<213> ORGANISM: Artificial Sequence
<220> FEATURE:
<223> OTHER INFORMATION: Forward primer for Paxillin

<400> SEQUENCE: 15
aactggttga agggtgttgc                                               20

<210> SEQ ID NO 16
<211> LENGTH: 20
<212> TYPE: DNA
<213> ORGANISM: Artificial Sequence
<220> FEATURE:
<223> OTHER INFORMATION: Reverse primer for Paxillin

<400> SEQUENCE: 16
aggttcagtg ggttcacagg                                               20

<210> SEQ ID NO 17
<211> LENGTH: 20
<212> TYPE: DNA
<213> ORGANISM: Artificial Sequence
<220> FEATURE:
<223> OTHER INFORMATION: Forward primer for FAK

<400> SEQUENCE: 17
cgagagattg agatggcaca                                               20

<210> SEQ ID NO 18
<211> LENGTH: 20
<212> TYPE: DNA
<213> ORGANISM: Artificial Sequence
<220> FEATURE:
<223> OTHER INFORMATION: Reverse primer for FAK

<400> SEQUENCE: 18
tactcttgct ggaggctggt                                               20

<210> SEQ ID NO 19
<211> LENGTH: 20
<212> TYPE: DNA
<213> ORGANISM: Artificial Sequence
<220> FEATURE:
<223> OTHER INFORMATION: Forward primer for ILK

<400> SEQUENCE: 19
aaggtgctga aggttcgaga                                               20

<210> SEQ ID NO 20
<211> LENGTH: 20
<212> TYPE: DNA
<213> ORGANISM: Artificial Sequence
<220> FEATURE:
<223> OTHER INFORMATION: Reverse primer for ILK

<400> SEQUENCE: 20
atacggcatc cagtgtgtga                                               20

-continued

```
<210> SEQ ID NO 21
<211> LENGTH: 20
<212> TYPE: DNA
<213> ORGANISM: Artificial Sequence
<220> FEATURE:
<223> OTHER INFORMATION: Forward primer for VDR

<400> SEQUENCE: 21
cggccggacc agaagccttt                                                   20

<210> SEQ ID NO 22
<211> LENGTH: 20
<212> TYPE: DNA
<213> ORGANISM: Artificial Sequence
<220> FEATURE:
<223> OTHER INFORMATION: Reverse primer for VDR

<400> SEQUENCE: 22
ctggcagtgg cgtcggttgt                                                   20

<210> SEQ ID NO 23
<211> LENGTH: 20
<212> TYPE: DNA
<213> ORGANISM: Artificial Sequence
<220> FEATURE:
<223> OTHER INFORMATION: Forward primer for MSX2

<400> SEQUENCE: 23
ccctggagcg caagttccgt                                                   20

<210> SEQ ID NO 24
<211> LENGTH: 20
<212> TYPE: DNA
<213> ORGANISM: Artificial Sequence
<220> FEATURE:
<223> OTHER INFORMATION: Reverse primer for MSX2

<400> SEQUENCE: 24
ggcgggatgg gaagcacagg                                                   20

<210> SEQ ID NO 25
<211> LENGTH: 20
<212> TYPE: DNA
<213> ORGANISM: Artificial Sequence
<220> FEATURE:
<223> OTHER INFORMATION: Forward primer for CD49f

<400> SEQUENCE: 25
tcatggatct gcaaatggaa                                                   20

<210> SEQ ID NO 26
<211> LENGTH: 20
<212> TYPE: DNA
<213> ORGANISM: Artificial Sequence
<220> FEATURE:
<223> OTHER INFORMATION: Reverse primer for CD49f

<400> SEQUENCE: 26
agggaaccaa cagcaacatc                                                   20

<210> SEQ ID NO 27
<211> LENGTH: 20
<212> TYPE: DNA
<213> ORGANISM: Artificial Sequence
<220> FEATURE:
<223> OTHER INFORMATION: Forward primer for OCT4
```

<400> SEQUENCE: 27
gtggaggaag ctgacaacaa                                               20

<210> SEQ ID NO 28
<211> LENGTH: 20
<212> TYPE: DNA
<213> ORGANISM: Artificial Sequence
<220> FEATURE:
<223> OTHER INFORMATION: Reverse primer for OCT4

<400> SEQUENCE: 28
attctccagg ttgcctctca                                               20

<210> SEQ ID NO 29
<211> LENGTH: 20
<212> TYPE: DNA
<213> ORGANISM: Artificial Sequence
<220> FEATURE:
<223> OTHER INFORMATION: Forward primer for SOX2

<400> SEQUENCE: 29
tggcgaacca tctctgtggt                                               20

<210> SEQ ID NO 30
<211> LENGTH: 20
<212> TYPE: DNA
<213> ORGANISM: Artificial Sequence
<220> FEATURE:
<223> OTHER INFORMATION: Reverse primer for SOX2

<400> SEQUENCE: 30
ccaacggtgt caacctgcat                                               20

<210> SEQ ID NO 31
<211> LENGTH: 20
<212> TYPE: DNA
<213> ORGANISM: Artificial Sequence
<220> FEATURE:
<223> OTHER INFORMATION: Forward primer for LIN28

<400> SEQUENCE: 31
ggggaatcac cctacaacct                                               20

<210> SEQ ID NO 32
<211> LENGTH: 20
<212> TYPE: DNA
<213> ORGANISM: Artificial Sequence
<220> FEATURE:
<223> OTHER INFORMATION: Reverse primer for LIN28

<400> SEQUENCE: 32
cttggctcca tgaatctggt                                               20

<210> SEQ ID NO 33
<211> LENGTH: 20
<212> TYPE: DNA
<213> ORGANISM: Artificial Sequence
<220> FEATURE:
<223> OTHER INFORMATION: Forward primer for NANOG

<400> SEQUENCE: 33
accttggctg ccgtctctgg                                               20

<210> SEQ ID NO 34
<211> LENGTH: 21

```
<212> TYPE: DNA
<213> ORGANISM: Artificial Sequence
<220> FEATURE:
<223> OTHER INFORMATION: Reverse primer for NANOG

<400> SEQUENCE: 34
agcaaagcct cccaatccca a                                        21

<210> SEQ ID NO 35
<211> LENGTH: 20
<212> TYPE: DNA
<213> ORGANISM: Artificial Sequence
<220> FEATURE:
<223> OTHER INFORMATION: Forward primer for CMYC

<400> SEQUENCE: 35
aagacagcgg cagcccgaac                                          20

<210> SEQ ID NO 36
<211> LENGTH: 20
<212> TYPE: DNA
<213> ORGANISM: Artificial Sequence
<220> FEATURE:
<223> OTHER INFORMATION: Reverse primer for CMYC

<400> SEQUENCE: 36
tgggcgagct gctgtcgttg                                          20

<210> SEQ ID NO 37
<211> LENGTH: 20
<212> TYPE: DNA
<213> ORGANISM: Artificial Sequence
<220> FEATURE:
<223> OTHER INFORMATION: Forward primer for KLF4

<400> SEQUENCE: 37
ggctgcacac gacttccccc                                          20

<210> SEQ ID NO 38
<211> LENGTH: 20
<212> TYPE: DNA
<213> ORGANISM: Artificial Sequence
<220> FEATURE:
<223> OTHER INFORMATION: Reverse primer for KLF4

<400> SEQUENCE: 38
ggtggcggtc cttttccggg                                          20

<210> SEQ ID NO 39
<211> LENGTH: 24
<212> TYPE: DNA
<213> ORGANISM: Artificial Sequence
<220> FEATURE:
<223> OTHER INFORMATION: Forward primer for CK18

<400> SEQUENCE: 39
aatgggaggc atccagaacg agaa                                     24

<210> SEQ ID NO 40
<211> LENGTH: 24
<212> TYPE: DNA
<213> ORGANISM: Artificial Sequence
<220> FEATURE:
<223> OTHER INFORMATION: Reverse primer for CK18

<400> SEQUENCE: 40
```

```
gggcattgtc cacagtattt gcga                                          24

<210> SEQ ID NO 41
<211> LENGTH: 20
<212> TYPE: DNA
<213> ORGANISM: Artificial Sequence
<220> FEATURE:
<223> OTHER INFORMATION: Forward primer for FOXA2

<400> SEQUENCE: 41
tgggagcggt gaagatggaa                                               20

<210> SEQ ID NO 42
<211> LENGTH: 20
<212> TYPE: DNA
<213> ORGANISM: Artificial Sequence
<220> FEATURE:
<223> OTHER INFORMATION: Reverse primer for FOXA2

<400> SEQUENCE: 42
tcatgccagc gcccacgtac                                               20

<210> SEQ ID NO 43
<211> LENGTH: 19
<212> TYPE: DNA
<213> ORGANISM: Artificial Sequence
<220> FEATURE:
<223> OTHER INFORMATION: Forward primer for PEPCK

<400> SEQUENCE: 43
ttagatggga caaagcctg                                                19

<210> SEQ ID NO 44
<211> LENGTH: 20
<212> TYPE: DNA
<213> ORGANISM: Artificial Sequence
<220> FEATURE:
<223> OTHER INFORMATION: Reverse primer for PEPCK

<400> SEQUENCE: 44
gcaagacggt gattgtaact                                               20

<210> SEQ ID NO 45
<211> LENGTH: 20
<212> TYPE: DNA
<213> ORGANISM: Artificial Sequence
<220> FEATURE:
<223> OTHER INFORMATION: Forward primer for HNF4a

<400> SEQUENCE: 45
ggaacatatg ggaaccaacg                                               20

<210> SEQ ID NO 46
<211> LENGTH: 20
<212> TYPE: DNA
<213> ORGANISM: Artificial Sequence
<220> FEATURE:
<223> OTHER INFORMATION: Reverse primer for HNF4a

<400> SEQUENCE: 46
aacttcctgc ttggtgatgg                                               20

<210> SEQ ID NO 47
<211> LENGTH: 20
<212> TYPE: DNA
<213> ORGANISM: Artificial Sequence
```

```
<220> FEATURE:
<223> OTHER INFORMATION: Forward primer for AFP

<400> SEQUENCE: 47
gaatgctgca aactgaccac                                              20

<210> SEQ ID NO 48
<211> LENGTH: 20
<212> TYPE: DNA
<213> ORGANISM: Artificial Sequence
<220> FEATURE:
<223> OTHER INFORMATION: Reverse primer for AFP

<400> SEQUENCE: 48
tggcattcaa gagggttttc                                              20

<210> SEQ ID NO 49
<211> LENGTH: 20
<212> TYPE: DNA
<213> ORGANISM: Artificial Sequence
<220> FEATURE:
<223> OTHER INFORMATION: Forward primer for TUJ-1

<400> SEQUENCE: 49
cagtgacctg caactggaga                                              20

<210> SEQ ID NO 50
<211> LENGTH: 20
<212> TYPE: DNA
<213> ORGANISM: Artificial Sequence
<220> FEATURE:
<223> OTHER INFORMATION: Reverse primer for TUJ-1

<400> SEQUENCE: 50
gattggccaa acacgaagtt                                              20

<210> SEQ ID NO 51
<211> LENGTH: 18
<212> TYPE: DNA
<213> ORGANISM: Artificial Sequence
<220> FEATURE:
<223> OTHER INFORMATION: Forward primer for MUSASHI

<400> SEQUENCE: 51
gcccaagatg gtgactcg                                                18

<210> SEQ ID NO 52
<211> LENGTH: 18
<212> TYPE: DNA
<213> ORGANISM: Artificial Sequence
<220> FEATURE:
<223> OTHER INFORMATION: Reverse primer for MUSASHI

<400> SEQUENCE: 52
atggcgtcgt ccaccttc                                                18

<210> SEQ ID NO 53
<211> LENGTH: 21
<212> TYPE: DNA
<213> ORGANISM: Artificial Sequence
<220> FEATURE:
<223> OTHER INFORMATION: Forward primer for NESTIN

<400> SEQUENCE: 53
aacagcgacg gactgtctct a                                            21
```

```
<210> SEQ ID NO 54
<211> LENGTH: 20
<212> TYPE: DNA
<213> ORGANISM: Artificial Sequence
<220> FEATURE:
<223> OTHER INFORMATION: Reverse primer for NESTIN

<400> SEQUENCE: 54
ttctcttgtc ccgcagactt                                                  20

<210> SEQ ID NO 55
<211> LENGTH: 20
<212> TYPE: DNA
<213> ORGANISM: Artificial Sequence
<220> FEATURE:
<223> OTHER INFORMATION: Forward primer for MAP2

<400> SEQUENCE: 55
ccaatggatt cccatacagg                                                  20

<210> SEQ ID NO 56
<211> LENGTH: 20
<212> TYPE: DNA
<213> ORGANISM: Artificial Sequence
<220> FEATURE:
<223> OTHER INFORMATION: Reverse primer for MAP2

<400> SEQUENCE: 56
tctccgttga tcccattctc                                                  20

<210> SEQ ID NO 57
<211> LENGTH: 20
<212> TYPE: DNA
<213> ORGANISM: Artificial Sequence
<220> FEATURE:
<223> OTHER INFORMATION: Forward primer for PAX6

<400> SEQUENCE: 57
acccattatc cagatgtgtt                                                  20

<210> SEQ ID NO 58
<211> LENGTH: 20
<212> TYPE: DNA
<213> ORGANISM: Artificial Sequence
<220> FEATURE:
<223> OTHER INFORMATION: Reverse primer for PAX6

<400> SEQUENCE: 58
atggtgaagc tgggcatagg                                                  20

<210> SEQ ID NO 59
<211> LENGTH: 20
<212> TYPE: DNA
<213> ORGANISM: Artificial Sequence
<220> FEATURE:
<223> OTHER INFORMATION: Forward primer for MSX1

<400> SEQUENCE: 59
cgagaggacc ccgtggatgc                                                  20

<210> SEQ ID NO 60
<211> LENGTH: 20
<212> TYPE: DNA
<213> ORGANISM: Artificial Sequence
<220> FEATURE:
<223> OTHER INFORMATION: Reverse primer for MSX1
```

```
<400> SEQUENCE: 60
ggcggccatc ttcagcttct                                               20

<210> SEQ ID NO 61
<211> LENGTH: 21
<212> TYPE: DNA
<213> ORGANISM: Artificial Sequence
<220> FEATURE:
<223> OTHER INFORMATION: Forward primer for BRACHYURY

<400> SEQUENCE: 61
gccctctccc tccccctcca c                                             21

<210> SEQ ID NO 62
<211> LENGTH: 20
<212> TYPE: DNA
<213> ORGANISM: Artificial Sequence
<220> FEATURE:
<223> OTHER INFORMATION: Reverse primer for BRACHYURY

<400> SEQUENCE: 62
ggcgccgttg ctcacagacc                                               20

<210> SEQ ID NO 63
<211> LENGTH: 20
<212> TYPE: DNA
<213> ORGANISM: Artificial Sequence
<220> FEATURE:
<223> OTHER INFORMATION: Forward primer for ColA2

<400> SEQUENCE: 63
ctggtgctgc tggccgagtc                                               20

<210> SEQ ID NO 64
<211> LENGTH: 20
<212> TYPE: DNA
<213> ORGANISM: Artificial Sequence
<220> FEATURE:
<223> OTHER INFORMATION: Reverse primer for ColA2

<400> SEQUENCE: 64
gggaccaggg ggaccacgtt                                               20

<210> SEQ ID NO 65
<211> LENGTH: 20
<212> TYPE: DNA
<213> ORGANISM: Artificial Sequence
<220> FEATURE:
<223> OTHER INFORMATION: Forward primer for CD49f primer-1

<400> SEQUENCE: 65
agaacaacgg gctcattcag                                               20

<210> SEQ ID NO 66
<211> LENGTH: 20
<212> TYPE: DNA
<213> ORGANISM: Artificial Sequence
<220> FEATURE:
<223> OTHER INFORMATION: Reverse primer for CD49f primer-1

<400> SEQUENCE: 66
cgacaggtag agcaagcaca                                               20

<210> SEQ ID NO 67
```

```
<211> LENGTH: 20
<212> TYPE: DNA
<213> ORGANISM: Artificial Sequence
<220> FEATURE:
<223> OTHER INFORMATION: Forward primer for CD49f primer-2

<400> SEQUENCE: 67
taggaaagaa cggcatcgtc                                               20

<210> SEQ ID NO 68
<211> LENGTH: 20
<212> TYPE: DNA
<213> ORGANISM: Artificial Sequence
<220> FEATURE:
<223> OTHER INFORMATION: Reverse primer for CD49f primer-2

<400> SEQUENCE: 68
ctaggatttt gcccaggtga                                               20

<210> SEQ ID NO 69
<211> LENGTH: 20
<212> TYPE: DNA
<213> ORGANISM: Artificial Sequence
<220> FEATURE:
<223> OTHER INFORMATION: Forward primer for CD49f primer-3

<400> SEQUENCE: 69
aacccctgca ggataaggtt                                               20

<210> SEQ ID NO 70
<211> LENGTH: 20
<212> TYPE: DNA
<213> ORGANISM: Artificial Sequence
<220> FEATURE:
<223> OTHER INFORMATION: Reverse primer for CD49f primer-3

<400> SEQUENCE: 70
agttgtgggg agaactgctg                                               20

<210> SEQ ID NO 71
<211> LENGTH: 20
<212> TYPE: DNA
<213> ORGANISM: Artificial Sequence
<220> FEATURE:
<223> OTHER INFORMATION: Forward primer for CD49f primer-4

<400> SEQUENCE: 71
tgatgttcac gcagcttttc                                               20

<210> SEQ ID NO 72
<211> LENGTH: 20
<212> TYPE: DNA
<213> ORGANISM: Artificial Sequence
<220> FEATURE:
<223> OTHER INFORMATION: Reverse primer for CD49f primer-4

<400> SEQUENCE: 72
ggaatctgac atccctgcat                                               20

<210> SEQ ID NO 73
<211> LENGTH: 20
<212> TYPE: DNA
<213> ORGANISM: Artificial Sequence
<220> FEATURE:
<223> OTHER INFORMATION: Forward primer for CD49f primer-5

<400> SEQUENCE: 73
```

```
acatggggat atccaagcag                                              20

<210> SEQ ID NO 74
<211> LENGTH: 20
<212> TYPE: DNA
<213> ORGANISM: Artificial Sequence
<220> FEATURE:
<223> OTHER INFORMATION: Reverse primer for CD49f primer-5

<400> SEQUENCE: 74
tgcccttagt tcctcacagg                                              20

<210> SEQ ID NO 75
<211> LENGTH: 20
<212> TYPE: DNA
<213> ORGANISM: Artificial Sequence
<220> FEATURE:
<223> OTHER INFORMATION: Forward primer for CD49f primer-6

<400> SEQUENCE: 75
ctggccaaaa cttgatggtt                                              20

<210> SEQ ID NO 76
<211> LENGTH: 20
<212> TYPE: DNA
<213> ORGANISM: Artificial Sequence
<220> FEATURE:
<223> OTHER INFORMATION: Reverse primer for CD49f primer-6

<400> SEQUENCE: 76
ccatcgcaaa tggaaaactt                                              20
```

CD49F PROMOTING PROLIFERATION, MULTIPOTENCY AND REPROGRAMMING OF ADULT STEM CELLS THROUGH PI3K/AKT/GSK3 PATHWAY

CROSS-REFERENCES TO RELATED APPLICATIONS

This application is a U.S. national phase application of International PCT Patent Application No. PCT/KR2011/001103, which was filed on Feb. 18, 2011, which claims priority to Korean Patent Application No. 10-2010-0014771, filed Feb. 18, 2010. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_017_01US_ST25.txt. The text file is 17 KB, was created on Dec. 10, 2012, and is being submitted electronically via EFS-Web.

TECHNICAL FIELD

The present invention relates to a method for obtaining adult stem cells, which have a surface antigen of CD49f, excellent formation of spheres due to sphere formation, and high expression of OCT4 and SOX2, from a cell source including stem cells, and a cell therapeutic agent containing adult stem cells obtained by said method or cells differentiated therefrom as an active ingredient.

BACKGROUND ART

Embryonic stem cells, as cells which can be generated from all of tridermic-derived cells and tissues, are obtained from inner cell mass (ICM) of blastocyst formed after about 4-5 days from fertilization, and therefore involve ethical problems. Further, because of their pluripotency, they can be highly proliferated and variously differentiated, but have problems that they are hard to control and may be converted into cancer cells.

On the other hand, adult stem cells can be obtained from bone marrow, umbilical cord blood, adipose tissues, etc., and thus, may avoid any ethical problem. Furthermore, it has been demonstrated that although adult stem cells have a plasticity inferior to embryonic stem cells, they have a multipotency, which allows them to differentiate into various cells including endothelium, bone, muscle, nerve cells.

Mesenchymal stem cells are a kind of adult stem cells, i.e. stem cells having a multipotency, which allows them to differentiate into hematopoietic system cells as well as tissues including muscle, nerve, bone, adipose tissue, etc. In general, they can be obtained through isolation from bone marrow, and in addition, can be obtained from various areas in the adult body. Adult stem cells derived from bone marrow have disadvantages in that their plasticity and proliferation potency are much poor as compared to other stem cells and the procedures for extracting them are invasive. Therefore, recently umbilical cord blood has come into notice as the alternative source of adult stem cells which can be used instead of bone marrow. Although the characteristics of umbilical cord blood-derived stem cells are substantially similar to those of bone marrow-derived mesenchymal stem cells, umbilical cord blood-derived stem cells have the characteristic properties which are superior to bone marrow-derived stem cells in view of the plasticity and proliferation potency.

Meanwhile, mesenchymal stem cells are adult stem cells characterized in that they are adhered and grown on the surface of cell culture plate, and have been demonstrated that they can be differentiated into adipocytes, chondrocyte, osteocytes, etc. under appropriate culture conditions (Erickson et al., Biochem. Biophys. Res. Commun., 290: 763, 2002; Halvorsen et al., Tissue Eng., 7:729, 2001; Wickham et al., Clin. Orthop. Relat. Res., 412:196, 2003; Dragoo et al., J. Bone Joint Surg., Br., 85:740, 2003). In addition, it has been reported that mesenchymal stem cells not only have an ability to differentiate into mesodermic cells including adipocytes, muscle cells, osteocytes, chondrocyte, etc., but also can be differentiated into non-mesodermic cells including pancreatic endocrine cells, liver cells, vascular endothelial cells and myocardial cells, and thus, an effort to use mesenchymal stem cells as a tool of cell therapeutic agents or gene therapeutic agents via self-transplantation has been actively made (Chung Jin Sup, J Korean Soc Transplant, 22:183-196, 2008).

At the present technical level, to use adult stem cells as the cell therapeutic agent it is required to standardize the culture conditions under which undifferentiated state can be maintained. In addition, since adult stem cells isolated from tissues are present in the mixed state of various kinds of cells, the technology capable of culturing homogeneous adult stem cells in a mass scale is also one of the problems sought to be solved.

In particular, the method for isolating adult stem cells from tissues or blood can generally include, for example, cell sorting utilizing antibodies for numerous surface antigens. However, said method has the limitation that the surface antigens for adult stem cells should be understood, and further, its use is greatly restricted by the problems that the common surface antigen (hereinafter, referred to as "marker") for adult stem cells has not been known; and markers for adult stem cells are not variously developed, and further, even the known markers show different degrees of expression depending on the differentiation state; and particularly, the sorting equipment is expensive.

In order to obtain adult stem cells in a large quantity, while maintaining a multipotent property, in vitro culture technologies have generally utilized the characteristic feature that said cells adhere to the cell culture plate.

Said method is accomplished by removing mononuclear cells from bone marrow or blood with density gradient centrifugation using Ficoll-Pague, and selectively culturing the adult stem cells adhered to the culture plate in the serum-containing culture solution. The cells obtained from the above procedures comprise adult stem cells, which may possibly be mixed with other mononuclear cells and other stem cells. However, such mixed cell culture conditions may result in differing the distribution degree of nutrients, thereby leading to the heterogeneity of cell differentiation state. In the end, the problem that said cells cannot be produced as the homogeneous cell population serves as the fatal disadvantage that when they are used as the therapeutic agent, the actual effect may be different from the intended effect. Therefore, there is an urgent need for development of the effective culture technology which can provide homogeneous adult stem cells in a large quantity.

DISCLOSURE

Technical Problem

Thus, the present inventors have found that in the courses of culturing and amplifying adult stem cells derived from umbilical cord blood, adipose tissue (hAD-MSC) and bone marrow (hBM-MSC) adult stem cells having an excellent sphere formation and a rapid culture rate have a specific surface antigen and an excellent plasticity property.

Further, the present inventors also have found that CD49f promotes proliferation, multipotency and reprogramming of adult stem cells through PI3K/AKT/GSK3 pathway.

The present invention is completed on the basis of such findings.

Technical Solution

The present invention provides the first method for preparing adult stem cells, which have CD49f-positive characteristic as the cell surface marker and improved homogeneity as compared to pre-culture stem cells, comprising (a) the first step of culturing adult stem cells under non-adhesive culture conditions; and (b) the second step of isolating adult stem cells from cell populations, which form spheres by sphere formation.

After completion of the first step for one week, the number of adult stem cell spheres can be 30 to 50 spheres per $1 \times 10^4$ cells, and the average diameter of spheres can be 100 to 150 μm.

The first method of the present invention can be conducted by repeating 2 times or more the first step and the second step. In such case, the first method can further comprise the step of separating the cell populations forming spheres into single cells after second step and before the repeated first step.

In addition, the present invention provides the second method for preparing homogeneous adult stem cells, comprising (a) the first step of preparing the cell source comprising stem cells; and (b) the second step of isolating CD49f-positive adult stem cells from said cell source.

Furthermore, the present invention provides CD49f-positive adult stem cells as prepared and isolated by the first method and the second method according to the present invention.

The present invention also provides a cell therapeutic agent containing as the active ingredient CD49f-positive adult stem cells as prepared and isolated by the first method and the second method according to the present invention, or cells differentiated therefrom.

The cell therapeutic agent provided by the present invention can have an ability to treat skeletal system disorders, tissue reconstruction, circular system disorders, nerve system disorders and immunological disorders. In addition, the cell therapeutic agent can uniformly control the differentiation state of cells because it contains homogeneous adult stem cells having CD49f-positive characteristics as the active ingredient.

The present invention also provides the method for proliferating adult stem cells, which comprises the step of culturing CD49f-positive adult stem cells as prepared and isolated by the first method and the second method according to the present invention.

Furthermore, the present invention provides the method for preparing differentiated cells from adult stem cells, which comprises the step of differentiating CD49f-positive, homogeneous adult stem cells as prepared and isolated by the first method and the second method according to the present invention.

In addition, the present invention provides a marker comprising CD49f for reprogramming into pluripotent cells.

Further, the present invention provides the method for identifying whether the pluripotency is reprogrammed in target cells for analysis or whether target cells for analysis maintains the pluripotency, characterized in that said method includes the step of measuring the level expression of CD49f in target cells for analysis. Furthermore, the present invention provides the method for improving the multipotency of stem cells by maintaining the expression of CD49f. In this case, CD49f can improve the multipotency, which is mediated by CD49f-PI3K/AKT/GSK3β signal transduction.

In addition, the present invention provides the method for maintaining the multipotency of stem cells characterized in that stem cells are incubated under non-adhesive culture conditions to maintain CD49f expression of cells at a high level via sphere formation.

Furthermore, the present invention provides the method for differentiating stem cells into a specific cell by inhibiting or knocking down the expression of CD49f.

Hereinafter, the present invention will be illustrated in detail.

Mesenchymal stem cells (MSCs), which can be derived from bone marrow (BM), adipose tissue (AD), and umbilical cord blood (UCB) are one of the stem cell sources for the therapeutic purpose.

MSCs have the multipotency, which means the multi-lineage plasticity, and allows them to differentiate into mesodermal as well as ectodermal nerve cells and endodermal stem cells in in-vitro experiment.

However, MSCs are generally incubated as the heterogeneous population. During the proliferation, the cell population is diversified in view of the self-renewal and plasticity. Therefore, it is required to isolate more homogenous cell population.

Although the important subject of the study is to find the markers for tissue-specific adult stem cells having higher multipotency from heterogeneous cell population, up to present there was no accurate marker for isolating adult stem cells. The present inventors have studied to find the methods for screening adult stem cells having higher multipotency, and thus identified that CD49f is an important novel marker, which can improve the self-renewal and plasticity of multipotent cells, reprogram the multipotent cells into pluripotent cell, and then maintain the pluripotent cells.

The term "anchorage independence" means the growth of three-dimensional eukaryotic cells, which are not adhered to solid substratum such as plastic culture plates or micro-carrier beads. Non-transformed somatic cells require extracellular matrix (ECM) for their anchorage and survival. Otherwise, cells undergo cell death process called anoikis. On the other hand, cancer cells having great tumorigenic and metastatic properties tend to survive without contacting with solid surface. The anchorage independent growth often forms the three-dimensional organoids called "spheres".

The present inventors have identified that adult stem cells can also form spheres under non-adhesive culture conditions and maintain the characteristics of adult stem cells even after formation of spheres of adult stem cells, by culturing adult stem cells derived from umbilical cord blood, adipose tissues (hAD-MSC) and bone marrow (hBM-MSC) in the non-adhesive culture plate coated with agar or agarose on the bottom thereof so that stem cells are not adhered to the bottom of cell culture plate, rather than using the common adhesive culture method taking advantage of the anchorage dependent property of cells.

The tissue plasticity, which means an ability of progeny cells capable of differentiating into the defined lineage in vitro, is an important characteristic of stem cells. The present inventors have demonstrated via tissue-specific staining and marker expression (FIG. 4) that all of adult stem cells obtained from monolayer culture or derived from spheres can be differentiated into adipose tissue, osteocyte systems. Surprisingly, cells derived from adult stem cell spheres had greater plasticity to differentiate into adipocytes and osteocytes, as compared to monolayer-incubated adult stem cells. Further, the proliferation rate of cells derived from adult stem cell spheres was faster than that of monolayer-incubated adult stem cells.

The present inventors have established the new mechanism of sphere format ion of adult stem cells, and also found that a certain integer in CD49f can affect the activity of PI3K/AKT/GSK3β to control the cell proliferation and differentiation. In addition, CD49f is involved in maintaining the pluripotency of hESCs and hiPSCs, and during the reprogramming process there is a crosstalk between OCT4, SOX2 and CD49f as pluripotency markers. That is, the present inventors have found that higher proliferation and multipotency in adult stem cell spheres are dependent on the signal transduction of CD49f-PI3K/AKT/GSK3 (see FIG. 1).

In general, intergrins, as a cell surface marker, are the counterparts of the constituents of ECM (extracellular matrix), and transmit the signal to a series of signal transduction pathways related to cell survival and proliferation, such as FAK (Focal Adhesion Kinases) and phosphatidylinositol 3-kinase (PI3K)/AKT pathways. When PI3K/AKT signal transduction is downregulated, the differentiation of hESCs is induced, and therefore, PI3K/AKT signal transduction is important in maintaining the pluripotency of hESCs. The signal transduction pathways initiated by interaction between integrins and ECM are cross-talked with signal transduction of growth factors via synergism to operate the cell cycle device.

In relation to molecular signal transduction cascades, PI3K and its downstream protein kinases (e.g., AKT and GSK3β) were increased in adult stem cell spheres as compared to the monolayer-incubated cells.

To confirm that PI3K signals are important in formation of adult stem cell spheres, chemical inhibitors for PI3K and chemical inhibitors for GSK3β as the downstream effector of PI3K were used. BIO as the inhibitor for GSK3β increased both the number and size of adult stem cell spheres. On the other hand, when incubated with LY294002 as an inhibitor of PI3K signal transduction the number of spheres was decreased. This result shows that the signal transduction of integrins-PI3K/AKT-GSK3β is important in forming MSC spheres.

On the basis of the hypothesis that PI3K/AKT survival signal is important in the cell-cell interaction involved in sphere formation, the levels of integrin expression were analyzed. Integrins belong to the cell anchorage-related family, which forms the heterogeneous dimeric complex between alpha-subunits and beta-subunits. It has been confirmed through immunocytochemistry and FACS analysis that among integrins CD49f (alpha 6) and CD104 (beta 4) were upregulated in sphere-derived cells.

The complex of integrin alpha 6/beta 4 is important in PI3K/AKT activation and cell proliferation via interaction with laminin and kallinin (anchorage filament protein). The downstream signal tranducers of integrins, for example, FAK and PAXILLIN were activated in sphere cells. This means that integrin signal is sufficient for priming PI3K/AKT signal pathway. Moreover, it has been confirmed that the sphere-forming efficiency and the size of spheres were significantly increased in CD49f-positive cells as compared to CD49f-negative cells. This means that CD49f-PI3K/AKT/GSK3 signal transduction plays an important role in survival and proliferation of adult stem cells under anchorage-independent growth conditions. Therefore, the present invention selects the sphere-derived cells, which become much rich in CD49f-positive cell groups as the new target for screening relatively homogeneous cell groups having greater proliferation and plasticity from heterogeneous cell population of adult stem cells.

In addition, the present inventors have confirmed that CD49f can directly control the proliferation and differentiation of adult stem cells.

Integrins are the major receptor, which mediates the anchorage of cells to cells or the anchorage of cells to ECM (extracellular matrix). It has been known that integrins are required for stimulating cell cycles via strengthened crosstalk between integrins and growth factor pathways. Moreover, it has been also known that CD49f-enriched adult stem cells can be more efficiently differentiated and have a superior colony-forming potential, as compared to other adult stem cells, which are not rich in CD49f.

Consistently with such results of studies, the present invention has confirmed through experiments that CD49f-overexpressing adult stem cells exhibit an improvement in proliferation potential, sphere-forming potential and plasticity into adipocyte, osteocyte systems.

Because cells derived from adult stem cell spheres exhibit relatively high activity in view of the cellular potency, the present inventors have set up the hypothesis that CD49f overexpression activates the PI3K/AKT/GSK3β pathway in adult stem cells. Although it has been known that in carcinoma cells CD49f activates PI3K/AKT pathway [Gambaletta et al., 2000; Trusolino et al., 2001], there is no evidence supporting any connection of CD49f with the signal transduction events related to proliferation and multipotency of stem cells. To confirm such connection the present inventors used Western blotting and inhibitors of signal transduction in adult stem cells in which CD49f is overexpressed. Interestingly, when CD49f and PI3K/AKT/GSK3β pathways were activated, the proliferation and sphere formation of adult stem cells were upregulated. As the sphere-forming efficiency is consistent with the proliferation and multipotency of adult stem cells, the sphere-forming efficiency can be representative of the cell plasticity of adult stem cells.

In combination with the results of other studies, which mention that PI3K/AKT network is important in osteogenic differentiation and bone growth (Fujita et al., 2004; Mukherjee and Rotwein, 2009), it appears that the activation of PI3K/AKT/GSK3β pathway by CD49f promotes the induction of differentiation of adult stem cells into osteocytes. Moreover, the present inventors have identified that treatment of adult stem cells with BIO as the inhibitor of GSK3 does not adversely affect the survival potential, and increases the propensity of adult stem cells to differentiate into osteocytes.

Although constitutively activated PI3K/AKT induces spontaneous differentiation into adipocytes (Kohn et al., 1996; Xu and Liao, 2004), the inhibition of GSK3 inhibits the differentiation into adipocytes by suppressing PPARγ as the main factor to regulate the production of adipocytes (Kang et al., 2007). Consistently with this, when BIO is present the osteogenic marker genes were upregulated, whereas the adipogenic marker genes were significantly reduced. The examples of the present invention have demonstrated that the signal transduction regulated by CD49f activates the PI3K/AKT/GSK3β pathway, and thus, is involved in stimulating the plasticity of adult stem cells.

In addition, the present inventors have identified that CD49f is an important, novel marker for reprogramming and maintaining the pluripotency.

According to recent studies, OCT4 as the pluripotency marker gene can regulate the proliferation potential, colony format ion and systematic plasticity of MSC (Greco et al., 2007; Liu et al., 2009; Tondreau et al., 2005). OCT4 and SOX2 are the transcription factors essential for maintaining the self-renewal capacity of undifferentiated embryonic stem cells (ESC). Such genes expressed in embryonic stem cells and tissue-specific adult stem cells such as MSCs help cells to maintain undifferentiated state and to not be differentiated. In addition, according to recent studies, it has been demonstrated that even differentiated cells can be converted into the pluripotent state by transduction of exogeneous plutipotent genes such as OCT4 and SOX2.

Since the proliferation and differentiation abilities of cells derived from hUCB-MSC spheres were significantly upregulated, the present inventors compared the expression level of pluripotent markers with that of monolayer-incubated hUCB-MSC. In cells derived from hUCB-MSC spheres the expression level of OCT4/SOX2/LIN28/NANOG was higher (FIG. 11). Thus result means that the formation of spheres can upregulate the expression of pluripotent markers to increase the pluripotency, thereby strengthening both the self-renewal and plasticity.

Moreover, the present inventors have also silenced OCT4 or SOX2 to downregulate the activity of CD49f, and further strengthened the expression of OCT4 and SOX2 to activate the intrinsic transcripts and proteins of CD49f. To ascertain whether the regulation of CD49f by OCT4 and SOX2 is due to the direct binding, the chromatin immunoprecipitation assay (CHIP) was conducted. Using the antibodies specific to OCT4 and SOX2, it has been ascertained by ChIP that those two transcription factors are combined to the presumed promoter domains of CD49f (FIG. 11). The interaction of OCT4 and SOX2 with CD49f can also be described as a transcription regulating loop through PI3K/AKT/GSK3β (FIG. 1).

Interestingly, the expression of CD49f was significantly improved in OCT4/SOX2/LIN28/NANOG-overexpressed adult stem cells. According to previous studies, it has been reported that 4 transcription factors (OCT4/SOX2/LIN28/NANOG or OCT4/SOX2/CMYC/KLF4) are sufficient for reprogramming differentiated cells to undifferentiated pluripotent stem cells (Takahashi et al., 2007; Yu et al., 2007). Consistently with the upregulated expression of CD49f, ectopic OCT4/SOX2/LIN28/NANOG-overexpressed MSCs exhibited a strong AP activity, and showed a morphology change into hESC-like colonies. In addition, the upregulated expression of intrinsic CD49f was significantly reduced as the induction of embryoid body (EB) formation is progressed in hiPSCs and hESCs. Such results mean that intrinsic CD49f expression can reflect the reprogramming state, and can be used as the reprogramming marker.

The knockdown of intrinsic CD49f induced the differentiation of hESCs, and reduced the level of intrinsic OCT4, SOX2 and NANOG. In addition to this, the blocking of CD49f inhibited PI3K/AKT/GSK3β pathway, which serves as the kernel factor in maintaining the pluripotency and/or survival potential in hESCs. Treatment with LY294002 as PI3K inhibitor specific to hESCs dependently inhibited the expression of NANOG and CD49f. FIG. 1 shows the schematic diagram of CD49f-PI3K/AKT/GSK3β pathway. Together with this, such findings suggest that during reprogramming procedures CD49f can be crosstalked with OCT4 and SOX2, and CD49 can contribute to the maintenance of pluripotency mediated by CD49f-PI3K/AKT/GSK3β signal transduction.

OCT4, SOX2 and NANOG can be combined to their promoters as well as to each other's promoters. Such autoregulatory circuitry stabilizes the pluripotent condition and genetic expression of hESCs and/or hiPSCs. OCT4 and SOX2 can co-occupy and activate the autoregulatory loop, and as the result, can activate the intrinsic pluripotency marker and induce the pluripotency. The present inventors have demonstrated that CD49f can be regulated by the auto-regulatory circuit of OCT4 and SOX2.

In the present specification, a spherical form or sphere means to include the complete spherical form as well as the ellipsoidal form. In the present specification, the "sphere formation" means the characteristic feature that in culture some cells capable of growing even without adhering to the bottom among adult stem cells form many aggregated spheres.

In the present specification, the "adult stem cells" are present in cartilage, bone, adipose tissue, bone marrow stroma, muscle, nerve, etc. and can be used together with the mesenchymal stromal cells, mesenchymal stem cells, or stromal cells.

The "adult stem cells" obtained by the first method or the second method of the present invention are the stem cells belonging to the sub-population, which has the ability to form spheres; the CD49f-positive characteristics in adult stem cells derived from adipose tissue, bone marrow and umbilical cord blood, preferably derived from umbilical cord blood; and also an ability of highly expressing OCT4 and SOX2 as the markers of pluripotent stem cells.

Although the adult stem cells obtained by the first method or the second method of the present invention are present in the state of spheres in culture, they can be dispersed as a single stem cell by the conventional methods, which can be readily selected by a person skilled in the art, such as enzyme treatment or physical methods.

The adult stem cells prepared by the first method can express ZNF281 or c-MYC, or both of them. The fact that adult stem cells of the present invention express Oct-4, Sox-2, c-myc, and ZNF281 means that said cells are maintained in the undifferentiated state.

The adult stem cells having CD49f-positive characteristics as obtained according to the second method of the present invention have the ability to form spheres due to the sphere formation, and can also have the ability to highly express OCT4 and SOX2.

In addition, the adult stem cells of the present invention, as compared to the spindle-shape adult stem cells incubated with adhering to the cell culture plate, have the ability to highly express proteins encoded by one or more genes selected from the group consisting of c-myc, paxillin, ilk, pI3K and nanog, and also have the characteristics that PI3K and GSK3β are highly phosphorylated.

The basis to judge the "high expression" in the present invention is to determine the high expression by comparing the identical properties of the adult stem cells derived from spheres as obtained by the non-adhesive culture, and the spindle-shaped adult stem cells as incubated with adhering to the bottom of cell culture plates according to the conventional culture method. In the adult stem cell of the present invention, the expression of OCT4 and SOX2 was shown to increase by more than about 9 times and 7 times, respectively.

The "cell source comprising stem cells" can include incubated adult stem cells, as well as adipose tissue, bone marrow, peripheral blood, umbilical cord blood, etc. comprising adult stem cells, umbilical cord blood being preferably used. Said cell sources derived from adipose tissue, bone marrow and umbilical cord blood can be in the mixed state of MSCs (mesenchymal stem cells) as well as blood cells, fibroblasts, endothelial cells, preadipocytes, etc.

Meanwhile, the isolation of adult stem cells having certain cell-surface antigenic and immunological properties, for example, the isolation by treatment with antibodies can utilize the means to detect fluorescence, magnets and nanoparticles.

Said means to detect fluorescence, magnets and nanoparticles are attached to antibodies, which can be isolated by the methods utilizing immunological properties of cells including, but not limited to, Fluorescence Activated Cell Sorter (FACS) or Magnetic Activated Cell Sorter (MACS), wherein said methods can be readily selected by a person with ordinary skills in the art.

The adult stem cells obtained by the first method or the second method of the present invention can be used as a cell therapeutic agent having an ability to treat one or more disorders selected from the group consisting of skeletal system disorders, tissue reconstruction, circular system disorders, nerve system disorders and immunological disorders, due to their excellent plasticity. The active ingredient of the cell therapeutic agent according to the present invention can be stem cells in the undifferentiated state or in the differentiated state into a certain cell.

The adult stem cells as the active ingredient of the cell therapeutic agent according to the present invention are cells belonging to the sub-population of MSCs, and therefore, can be differentiated according to the same method as in MSCs.

The MSCs can be differentiated into osteoblasts even in vitro by addition of dexamethasone, ascorbic acid phosphate, β-glycerophosphate, etc. It has been known that taking advantage of such plasticity said cells either alone or together with a carrier can treat a broad range of fracture. Particularly, although MSCs can be transplanted into damaged area to obtain the effect due to direct differentiation, it has been identified that in case of patients having oesteogenesis imperfecta, which is a congenital disease characterized by type I gelatinoid forming disorder, the systemic transplantation of homologous stem cells through blood flow can provide a therapeutic effect.

In addition, the cartilage-derived culture solution containing insulin, transferrin, selenous acid, etc. can be used to readily differentiate MSCs into cartilage tissues. It has been known that taking advantage of such plasticity it can be transplanted together with a carrier such as PCL, PLA, fibrin gel, etc. to restore the cartilage tissue in case of arthritis to which drug treatment is limited, or damage of articular cartilage.

The mesenchymal stem cells can be differentiated into adipocytes in vitro by using dexamethasone, indometacin, isobutylxanthin, insulin, etc., and taking advantage of such plasticity, their use has been gradually increased in relation to tissue reconstruction in the field of a plastic surgery utilizing adipocytes.

In addition, it has been known that MSCs can be differentiated into myocardial cell by treatment with 5-azacytidine, and that when MSCs are injected into brain they not only are transferred to the frontal lobe and cerebellum, but also provide a neurofilament positive reaction. Thus, it has been identified that said cells have an ability to regenerate nerve tissues. Therefore, it has been known that they can be used as a therapeutic agent for neurodegenerative disease such as Parkinson's disease, Huntington's disease, Alzheimer syndrome, multiple sclerosis, and damage of spinal cord, etc.

In addition to this, MSCs can be represented by MHC I$^+$, MHCII$^-$, CD40$^-$.CD80$^-$.CD86$^-$, and are characterized in that they can activate T cells by MHC I but have no costimulatory factor so that they cannot induce immune response due to T cells. Therefore, it has been known that in case of homograft there is no need to administer the immunosuppressant. Moreover, they are characterized in that they inhibit differentiation and functions of dendritic cell, and further inhibit proliferation, differentiation and chemotaxis of B cells. Utilizing such immunosuppressive function of MSCs a potential of MSCs to treat immunological disorders including rheumatoid arthritis, acute inflammation, etc. has been identified.

The present invention also provides a method for proliferating adult stem cells, which comprises the step of culturing adult stem cells prepared by the first method or the second method of the present invention and having CD49f-positive characteristics.

In the proliferation method of the present invention, the said culture of adult stem cells can be carried out by either suspension culture or adhesive culture.

The said suspension culture can use the culture plate of which bottom is coated with agarose, such that stem cells are not adhered to the bottom of cell incubator, and the said adhesive culture can be accomplished by common methods for culturing cells.

In general, the cell culture plates are specially treated in order to induce cell anchorage. Therefore, in addition to 1% to 10% agarose coating methods, the culture plates to which cells are not adhered and in which the suspension culture of cells is possible, for example, petri dish for culturing microorganisms, glass-made vessels, etc. can be used for culture. The concentration of said agarose and culture plates can be readily selected by a person skilled in the art.

The medium used in the proliferation method of the present invention includes all of the common mediums, which are used in the art relevant to said cell culture, with Dulbecco's Modified Eagle's Medium (DMEM) being most preferably used. In addition, antibiotics, fetal bovine serum (FBS) and growth factors can be added to the basal culture medium. The culture conditions including incubation temperature and incubation period can also be readily selected by a person skilled in the art.

The growth factors which can be added to the medium used for the proliferation method of the present invention can include, but not limited to, Bone Morphogenetic Proteins (BMPs), EGF Family, growth differentiation factors (GDFs), IGF Family, VEGF/PDFG Family, etc.

The proliferation method of the present invention can be utilized for proliferating said stem cells when much stem cells are needed for use as the cell therapeutic agent.

The present invention can obtain stem cells having uniform cytological properties in a large quantity, since in the present invention adult stem cells having CD49f-positive characteristics are isolated and incubated.

Further, in case where stem cells are amplified according to the proliferation method of the present invention, the present invention can more rapidly obtain adult stem cells in a large quantity as compared to prior methods, due to a rapid cell growth as compared to CD49f-negative stem cells.

Advantageous Effects

According to the present invention, adult stem cells derived from spheres are suitable for mass culture of adult stem cells because of more rapid growth thereof compared with stem cells obtained by a known adhesive culture method, have a specific surface antigen so as to be homogeneously obtained by using the specific surface antigen, and are useful for preparing a cell therapeutic agent using the same because of excellent differentiation thereof.

DESCRIPTION OF DRAWINGS

FIG. 2 shows the results from identification of spheres obtained by culture of respective tissues and stem cell markers present in said spheres. FIG. 2(C) is the expression conditions of CD34 and CD117, which are hematopoietic cell-specific markers, in monolayer-incubated MSCs and MSC-derived spheres as measured by FACS.

FIG. 4 (H) is the adipocyte differentiation efficiency as measured by the expression of adipocyte marker genes such as C/EBP β, AP2, PPARγ, and LEPTIN.

FIGS. 7 and 7B are the result of observation of the expression of integrin-related surface antigens in adhesive culture-monolayer formation (Comparative Example 1) and sphere-derived cells (Example 1). That is, the expression levels of CD49a, CD49b, CD49e, CD49f, and CD104 in MSC sphere-derived cells (Example 1) and monolayer-incubated MSCs (Comparative Example 1) as measured by FACS. The results were charted after conducting FACS analysis three times (*, $P<0.05$; **, $P<0.01$).

FIG. 8(E) shows the result obtained by conducting RT-PCR for both of CD49f-negative and CD49f-positive cell groups to analyze the expression levels of CD49f, PAXILLIN, FAK, ILK as integrin-related markers. FIG. 8(F) shows the result obtained by sorting cells into CD49f-negative and -positive cells with flow cytometer, and then identifying the sphere-forming efficiency of respective cell group (*, $P<0.05$; **, $P<0.01$).

FIG. 9(A) shows the result of MTT cell proliferation analysis in the presence or absence of CD49f, LY294002, BIO. Cells were seeded onto 24-well plate, and then the optical density was measured after 24 hour and 48 hours (*, $P<0.05$; **, $P<0.01$). FIG. 9(B) is the result of measuring a size of spheres in the presence or absence of CD49f, LY294002, BIO (*, $P<0.05$; **, $P<0.01$). FIG. 9(C) is the result of Western blot analysis for PI3K/AKT/GSK3β. CD49f expression vector was transduced into cells, which were than treated with LY294002 and BIO. Using phospho-specific antibodies for respective proteins the phosphorylation level of protein kinases was identified via Western blotting. 20 μg of protein lysate was loaded onto each well.

FIG. 10(B) shows the result obtained by incubating the Alizarin Red S stained plate with cetylpyridinium chloride, and then identifying the eluted Alizarin Red S solution via ELISA at 570 nm (*, $P<0.05$; **, $P<0.01$). FIG. 10 (C) shows the osteocyte differentiation efficiency identified as the expression of osteocyte marker genes such as BGLAP, VDR, MSX2, Osteocalcin, RUNX2. FIG. 10(D) shows the result obtained by incubating adult stem cells in adipocyte induction medium in the presence or absence of CD49f, LY294002, BIO, and 2 weeks after induction visualizing lipid droplet accumulation in cytoplasm via oil red 0 staining. FIG. 10(E) shows the result obtained by eluting Oil Red 0 with 100% isopropanol and then optically measuring the absorbance at 500 nm (*, P<0.05; **, P<0.01). FIG. 10(F) shows the adipocyte differentiation efficiency as identified by the expression of adipocyte marker genes such as CEBP-β, AP2, PPAR-γ, LEPTIN.

FIG. 13(A) shows the infection of adult stem cells with the combination of indicated genes. In this figure, bright-field images and alkaline-phosphate reactivity are represented. FIG. 13(D) shows the expression levels of tridermic markers of hESCs into which CD49f, pluripotent markers, and siCon, and siCD49f are transduced.

FIG. 14(A) shows phase contrast images of human iPSCs and hESCs. For spontaneous differentiation, hiPSCs and hESCs were subjected to suspension-culture for 8 days to form embryoid bodies (EBs). To conduct supplementary differentiation, EBs were transferred to a gelatin-coated plate and then, maintained for 8 days. FIG. 14 (B) shows phase contrast images of hESCs into which control siRNA and CD49f-targeted siRNA are transduced.

BEST MODE

Figure 1:
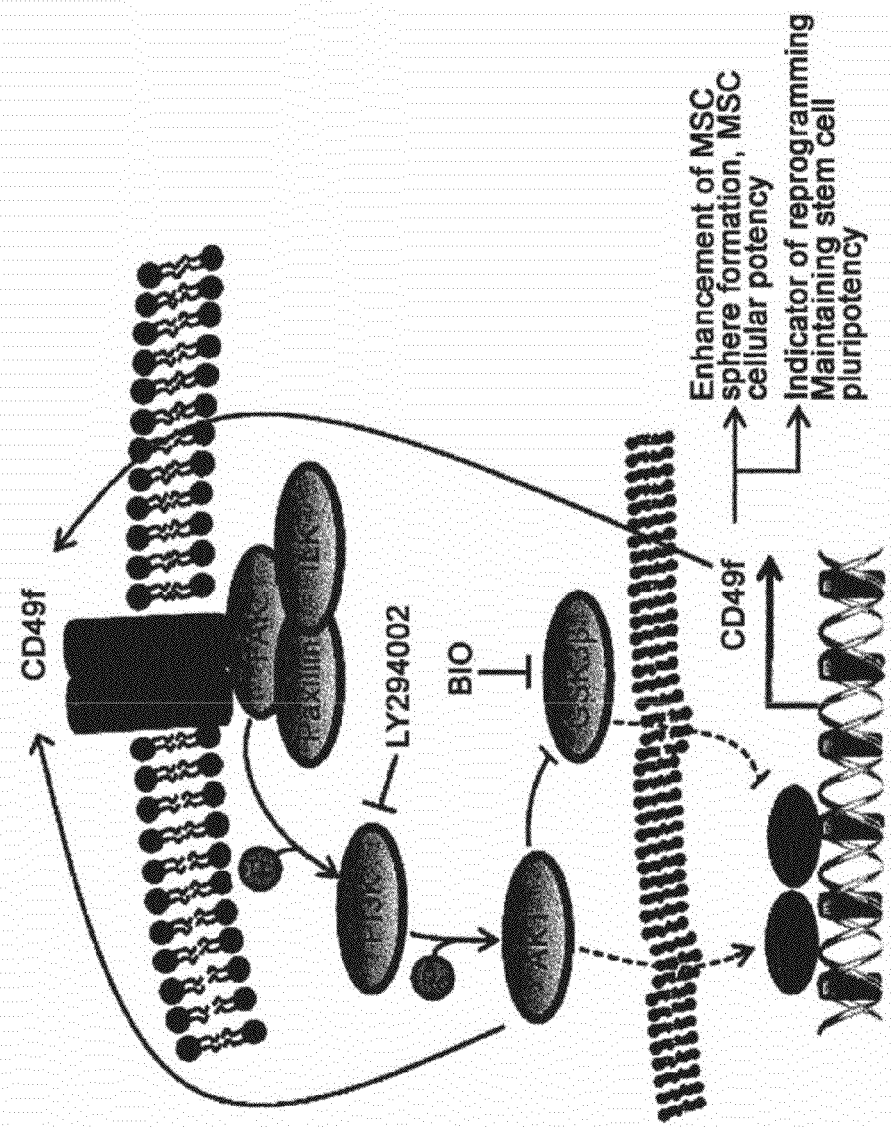
FIG. 1 is a schematic diagram showing a role of CD49f for MSC spheres and reprogramming. It summarizes a role of CD49f in adult stem cells, and shows how CD49f activation causes phosphorylation of PI3K/AKT, and is involved in the enhancement of MSC sphere formation and MSC cellular potency.

Hereinafter, it is intended to illustrate more in detail the present invention through the following Examples. The following Examples are provided only to more specifically explain the present invention, and it will be apparent to by a person skilled in the art that the scope of the present invention is not limited by those Examples according to the gist of the present invention.

Preparation 1: Isolation of MSCs from Umbilical Cord Blood

With the Institutional Review Board (IRB) of Boramae Medical Center and maternities, adult stem cells were extracted from hUCB obtained after delivery. UCB sample was mixed with HetaSep solution (Stem Cell Technology, Vancouver, Canada) in the ratio of 5:1, and the mixture was incubated at room temperature until blood cells were eliminated. Supernatant was collected and centrifuged with 2,500 rpm for 20 minutes using Ficoll density gradient. Mononuclear cells were obtained and then seeded onto culture plate under normal culture conditions.

The growth medium was DMEM (Invitrogen, Carlsbad, USA) comprising 10% FBS, 10 ng/ml bFGF, 5 ng/ml EGF, 20 ng/ml long R3-IGF1, and 1 ug/ml ascorbic acid. All of the procedures were approved by IRB of the Seoul National University (IRB No. 0603/001-002-07C1).

Preparation 2: Preparation of Human Embryonic Stem Cells

Human embryonic stem cells (hESCs) were obtained from CHA stem cell research laboratory under the material transfer agreement. hESCs and human induced pluripotent stem cells (hiPSCs) were maintained using human ES/iPS cell medium in STO feeder cells treated with mitomycin C. As described in the reference (Cowan et al., 2004), 20% knockout serum replacement, 20 ng/ml bFGF, 1% nonessential amino acids, 1% GlutaMAX, 1% penicillin/streptomycin, and 0.1 mM β-mercaptoethanol were added to Knockout DMEM. All of the procedures were approved by IRB of the Seoul National University (IRB No. 1008/001-001).

Example 1

Sphere Formation of Adult Stem Cells Derived from Umbilical Cord Blood

To form adult stem cell spheres with preventing the adhesion of cells to the bottom of plastic container, 100 mm culture plate coated with 1% agarose (Nunc, Rochester, N.Y.) was used, and 1.5×10$^5$ adult stem cells were incubated in the growth medium as described in Preparation 1. A total of 15,000 cells were seeded per 1 ml of the medium, and adult stem cell spheres were incubated for one week. To prevent cell loss the culture solution was partially replaced only two times per week. After 7 days, adult stem cell spheres were collected by means of 40 μm pore cell strainer. Adult stem cell spheres as collected were washed with PBS, and gently centrifuged (800 rpm/5 min) for supplementary experiments.

Example 2

Sphere Formation of Adult Stem Cells Derived from Adipose Tissue and Bone Marrow Spheres of adult stem cells were collected according to the same method as Example 1, except that adult stem cells derived from adipose tissues and bone marrow were used instead of hUCB-derived adult stem cells.

Comparative Example 1

Monolayer Culture of Adult Stem Cells Derived from Umbilical Cord Blood

Cells obtained from Preparation 1 were subjected to monolayer culture in plastic culture plate.

Experiment 1

Identification of Surface Antigens of Adult Stem Cell Spheres

When cells were monolayer-incubated as in Comparative Example 1, adult stem cells displayed a flattened and spindle-shaped morphology, whereas in case of non-adhesive culture as in Examples 1 and 2 floating spheroidal colonies (adult stem cell spheres) were formed. In order to identify surface antigens, which display the characteristics of adult stem cells, in cells obtained from adult stem cell spheres collected by Comparative Example 1 and Examples 1 and 2 the respective cells were collected by centrifugation, stained by treatment with CD44-FITC, CD90-Alexa Fluor 647, CD34-PE and CD117-PE (BD Bioscience, San Jose, Calif., USA) as monoclonal mouse anti-human fluorochrome-conjugated antibodies, and then subjected to the analysis for cell surface markers using FACSAria (BD Bioscience, San Jose, Calif., USA) and FACSDiva software (BD Bioscience, San Jose, Calif., USA).

Figure 2A:
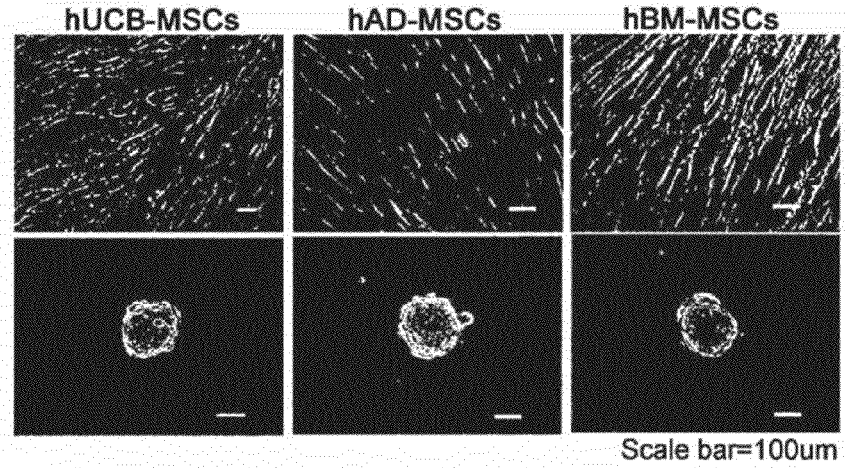
FIG. 2A is microphotographs of adult stem cells incubated from umbilical cord blood (hUCB-MSC), adipose tissue (hAD-MSC) and bone marrow (hBM-MSC).

As the result, it was identified that even in case of the culture in state of spheres there was no change in the surface antigens of stem cells (FIG. 2).

Figure 2B:
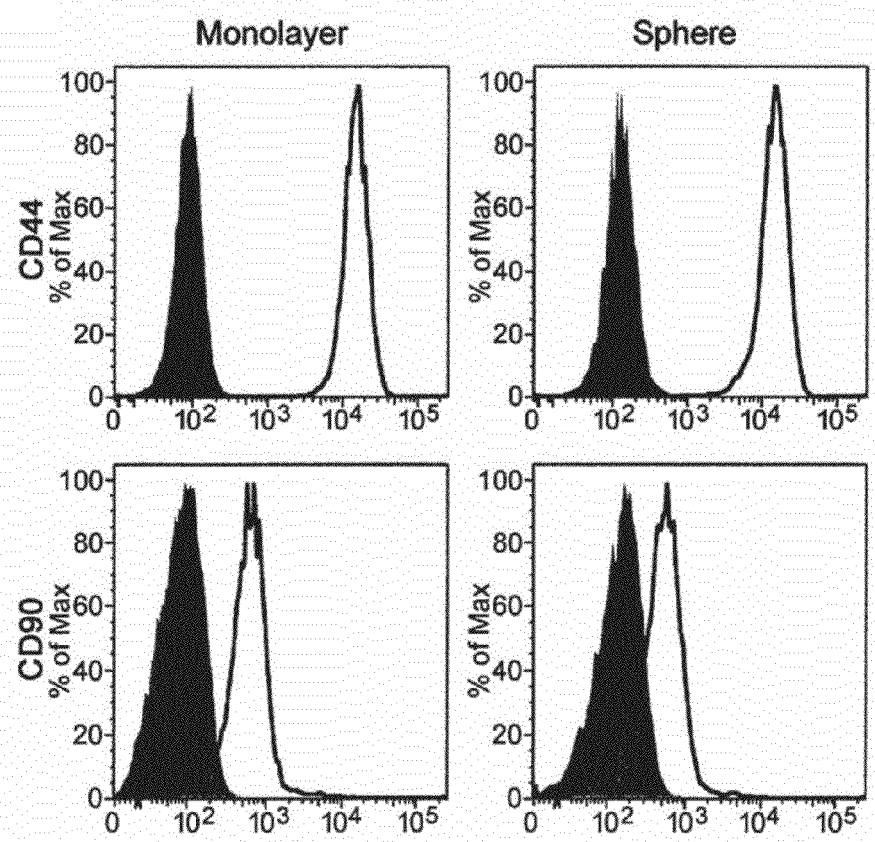
FIG. 2(B) is the expression conditions of adult stem cell positive surface markers, such as CD44 (upper panel) and CD90 (lower panel), in monolayer-incubated adult stem cells and spheres derived from adult stem cells as measured by FACS.

Through FACS analysis, it was identified whether MSC markers were expressed on the surface of monolayer-incubated cells derived from adult stem cells and adult stem cells-derived spheres. As shown in FIG. 2B, both of monolayer-incubated cells and MSC spheres were positive for MSC markers (CD44 and CD90), but negative for CD34 and CD117 as hematopoietic stem cell markers (FIG. 2C).

Experiment 3

Cell Division Potential of Adult Stem Cell Spheres

The spheres collected in Example 1 were changed into single cells, and then maintained in 10% FBS-containing medium along with adult stem cells of Comparative Example 1, and sub-cultured at the interval of every week. Estimated proliferation potential was measured by determining cumulative population doubling level (CPDL) using the following equation as described in the reference (Park et al., 2009, Histone deacetylase inhibitors decrease proliferation potential and multi lineage differentiation capability of human mesenchymal stem cells. Cell Prolif 42, 711-720).

$$CPDL=\ln(Nf/Ni)/\ln 2$$

In the above equation, Ni and Nf are the initial and final numbers of cells, respectively. A total of 50,000 cells were initially plated on 6-well culture plate (Nunc, Rochester, N.Y.), and then cells were counted once per week.

Figure 3A:
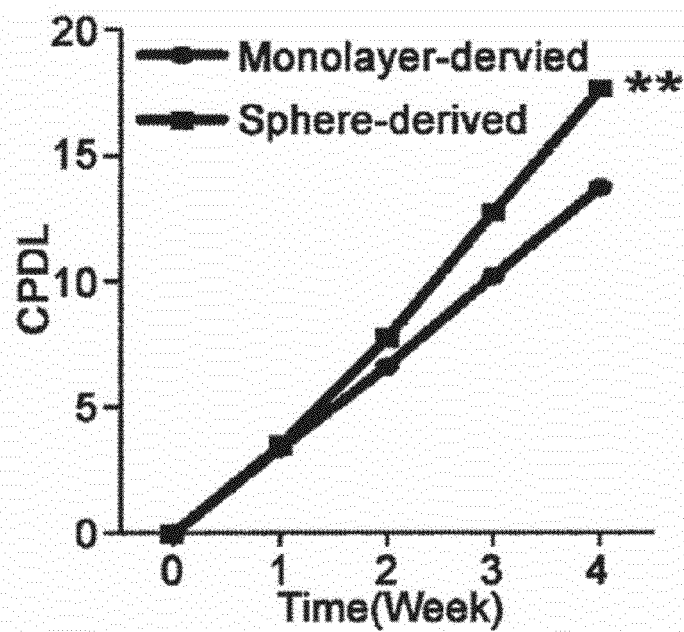
FIG. 3(A) is a graph showing the cellular proliferation potency (CPDL) of monolayer-incubated cells (Comparative Example 1) and sphere-derived cells (Example 1) (*, $P<0.05$; **, $P<0.01$).

From assessment of CPDL, the proliferation potentials of monolayer-incubated cells (Comparative Example 1) and sphere-derived cells (Example 1) were compared. After 2 weeks, at CPDL 7.7 sphere-derived cells exhibited a rapid cell proliferation as compared to monolayer-incubated cells (FIG. 3A). Such data demonstrated that adult stem cell spheres share the immunological properties with adult stem cells, and sphere-derived cells are more violently divided as compared to monolayer-incubated cells.

Experiment 4

Change in Genetic Expression of Cells Constituting Spheres Derived from Adult Stem Cells Adult stem cells were subject to non-adhesive culture according to the same method as Example 1. On the 7 day after initiation of culture, spheres obtained therefrom were collected, passed through 40 μm cell strainer, washed with PBS, and then centrifuged to obtain the first spheres. Said first spheres (P6) were separated into the single cell state with trypsin-EDTA, and transferred to new culture plate coated with agarose to prepare the second spheres (P12).

From said spheres (spheres (P6) and spheres (P12)) and monolayer-incubated adult stem cells as collected in Comparative Example 1, total RNA was extracted using Trizol Reagent™ (Invitrogen, USA) according to the protocol recommended by the manufacturer, and then mixed with oligo dT primer and Accupower RT premix (Bioneer, Korea) to synthesize cDNA. Using said cDNA as the template, PCR was conducted utilizing Accupower PCR premix (Bioneer, Korea) according to the protocol recommended by the manufacturer.

Figure 3B:
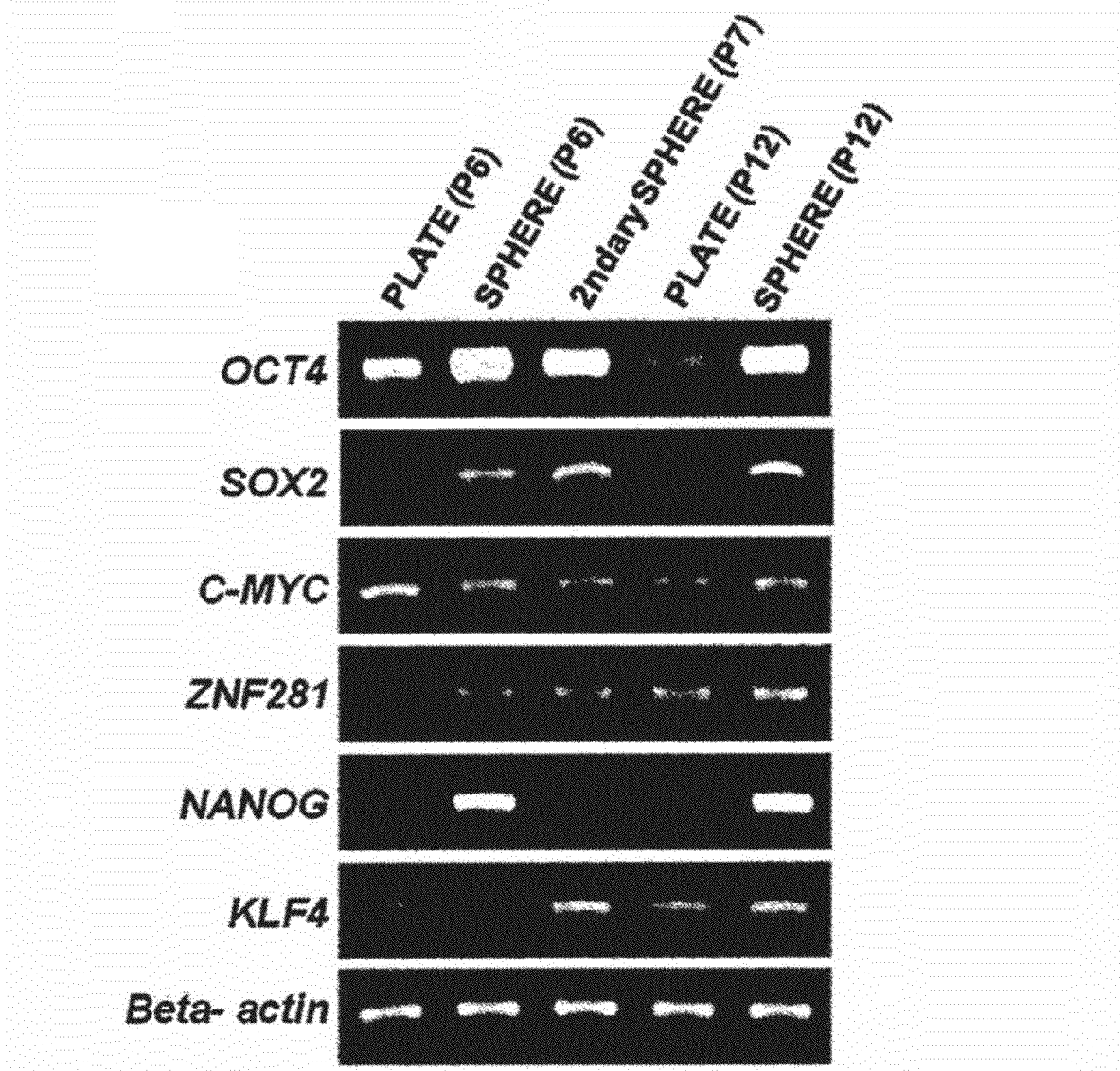
FIG. 3(B) shows a change in genetic expression of monolayer-incubated cells (Comparative Example 1) and sphere-derived cells (Example 1).

As the result, it was identified that the first and second spheres obtained from non-adhesive culture exhibit an improvement in OCT4, SOX2 and NANOG expressions as compared to monolayer-culture, and show no change in ZNF281 and c-MYC expressions (FIG. 3B).

Example 3

Identification of Cell Plasticity of Adult Stem Cell-Derived Spheres

The plasticity of monolayer-incubated cells (Comparative Example 1) and sphere-derived cells (Example 1) into adipose tissue, bone tissue and nerve tissue was observed.

3-1. Differentiation into Adipose Tissue

The cell culture of monolayer-incubated cells (Comparative Example 1) and sphere-derived cells (Example 1) was conducted using DMEM containing 5% FBS, 1 μM dexamethasone, 10 μM insulin, 200 μM indomethacin, and 0.5 mM isobutylmethylxanthine to induce differentiation into adipose tissue.

To determine the differentiation degree from fat accumulation present in cells, incubated cells were stained with Oil Red 0, and then Oil Red ° penetrated into cells was extracted with 100% isopropyl alcohol, and quantified with ELISA plate reader (EL800, Bio-Tek Instruments, USA) at OD 500. In addition, using RT-PCR the expression of C/EBP β, AP2, and PPARγ as adipose tissue-specific genes was examined.

Figure 4A:
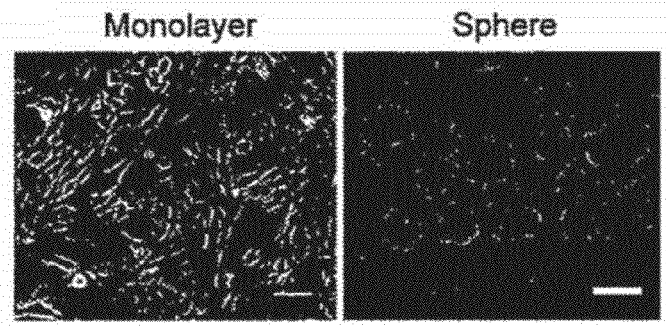
FIG. 4(A) shows phase contrast images of adult stem cells incubated in Comparative Example 1 (adhesive culture—monolayer formation) and Example 1 (non-adhesive culture—sphere formation). On the average, 15,000 cells were seeded per 1 mL of medium. Scale bar=100 μm.
Figure 4B:
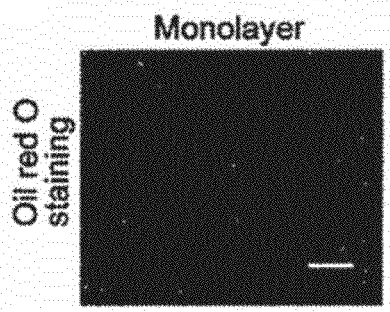
FIG. 4(B-E) shows phase contrast images of monolayer cells (left panel) and sphere-derived cells (right panel) after induction to specific tissues. Lipid droplet accumulation in differentiated cells was visualized by oil red 0 staining after 3 weeks from induct ion of adipocytes (B, C). After 3 weeks from osteocytes induction, mineral deposition was stained with Alizarin Red S (D, E).
FIG. 4(F) shows the result obtained by eluting the dye of Oil red 0 staining with 100% isopropanol and then measuring the absorbance at 500 nm wavelength (*, $P<0.05$; **, $P<0.01$).
FIG. 4(G) shows the result obtained by using a total of 100 nM cetylpyridinium chloride for elution of Alizarin Red S dye and measuring the absorbance at 570 nm wavelength (*, $P<0.05$; **, $P<0.01$).
FIG. 4(I) shows the expression levels of bone-specific OSTEOCALCIN and osteoblast-specific transcription factor RUNX2 as identified for determining the osteocyte induction efficiency.
Figure 4C:
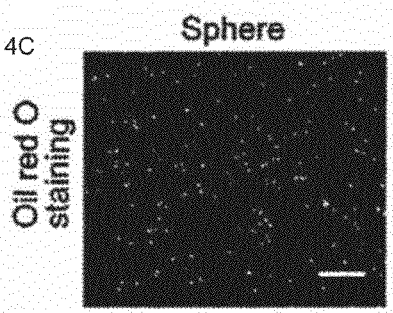
Figure 4D:
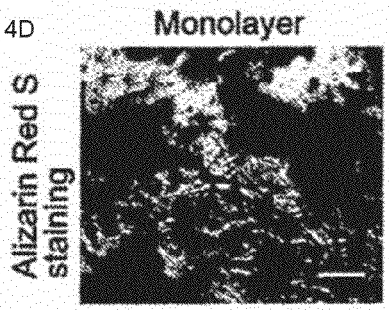
Figure 4G:
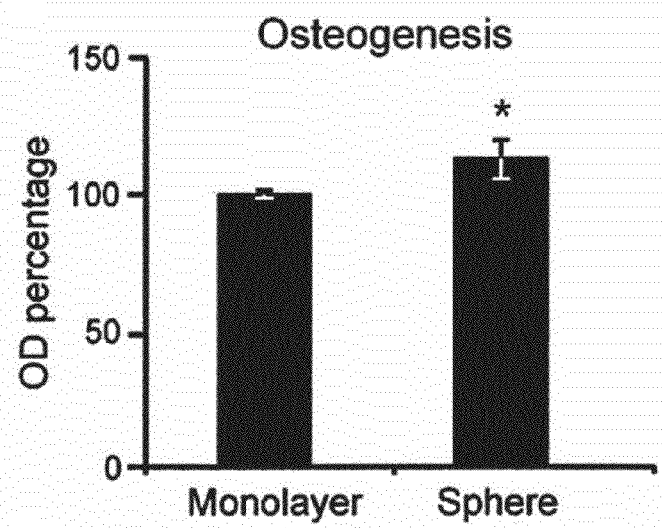
Figure 4H:
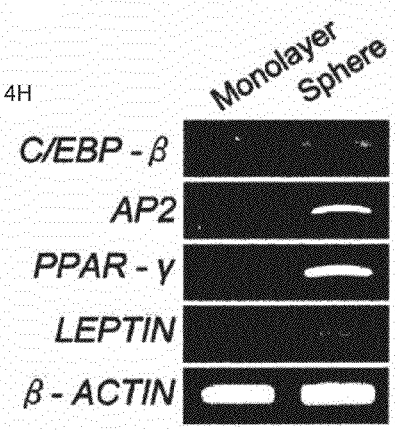

As the result, it was found that the degree of Oil Red 0 staining is higher in spheres, and particularly the expression of C/EBP β, AP2, PPARγ and Leptin as adipose tissue-specific genes is much higher in spheres as compared to monolayer-incubated MSCs (FIGS. 4C, 4F, and 4H). This suggests that MSC sphere-derived cells have a higher potential of differentiation into adipocyte system.

3-2. Differentiation into Bone Tissue

The monolayer-incubated cells (Comparative Example 1) and sphere-derived cells (Example 1) were incubated in DMEM containing 5% FBS, 50 μM L-ascorbate-2-phosphate, 0.1 μM dexamethasone and 10 μM glycerolphosphate to induce differentiation into bone tissue. The cells were stained with Alizarin Red dye specific to calcium, and then the dye was extracted by treating with 100 mM cetylpyridinium chloride (Sigma-Aldrich) for one hour and used for quantitative analysis. The emission of solubilized Alizarin Red S was measured by means of spectrophotometer at 570 nm.

In addition, using RT-PCR the expression of OSTEOCALCIN and RUNX2, which are genes specific to bone tissue, was examined.

Figure 4I:
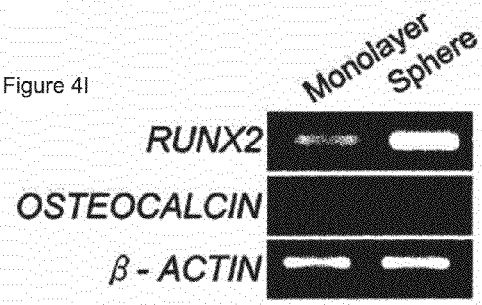

Through Alizarin Red S staining, it was identified that sphere-derived MSCs are more effective for differentiation into osteocytes. The sphere-derived cells exhibited an increase in the expression level of OSTEOCALCIN and RUNX2 after induction of osteocytes (FIGS. 4E, 4G and 4I). This suggests that MSC sphere-derived cells have a higher potential of differentiation into osteocyte system.

3-3. Differentiation into Nerve Tissue

The monolayer-incubated cells (Comparative Example 1) and sphere-derived cells (Example 1) were maintained in pre-induction medium of DMEM containing 5% FBS and 10 ng/ml βFGF at the initial stage of culture, and then incubated with DMEM containing 100 μM BHA, 50 μM forskolin, 2% DMSO, 25 mM KCl, 2 mM valproic acid, 1× B27 supplement, 10 ng/ml βFGF and 10 ng/ml PDGF for 24 hours for differentiation into nerve cells.

RNA was extracted from cells differentiated according to said method, and used as the template for RT-PCR. The expression of MAP2, TUJ-1 and PAX6 as genes specific to nerve cell was examined.

Figure 5:
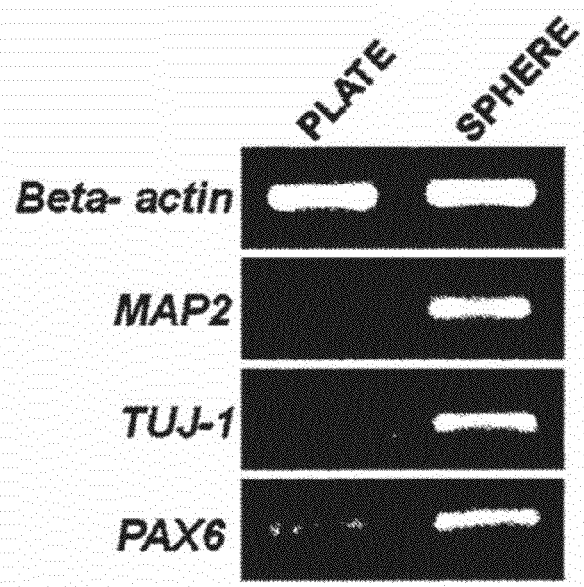
FIG. 5 shows the plasticity of adult stem cells incubated in Comparative Example 1 (adhesive culture—monolayer formation) and Example 1 (non-adhesive culture—sphere formation) into nerve cells.

As the result, it was found that the expression of MAP2, TUJ-1 and PAX6 as genes specific to nerve cell is greatly increased in cells differentiated from sphere-derived cells as compared to cells differentiated from monolayer-incubated cells (FIG. 5).

Experiment 5

Adult Stem Cell Spheres Regulate Cell Proliferation and Survival of MSC Spheres Via PI3K/AKT/GSK3β Pathway To identify the influence of GSK3 and PI3K signal transduction on sphere formation the inhibitory experiment was practiced. After treatment with BIO (Sigma-Aldrich) as GSK3 inhibitor at the concentration of 0 μM, 0.2 μM, or 0.5 μM, or with LY294001 (Calbiochem, La Jolla, Calif.) as PI3K inhibitor at the concentration of 0 μM, 10 μM, 30 μM, or 50 μM the formation of adult stem cell spheres was observed. The number of adult stem cell spheres was counted after 7 days from culture.

Western blot analysis for PI3K, AKT, and GSK3β was conducted according to the reference (Park et al., 2009). Adult stem cells incubated as monolayer or spheres were crushed in 50 mM Tris-HCl buffer comprising 1% Triton X-100 to which 1 mM phenylmethylsulfonyl fluoride, 1 mM aprotinin, 1 mM leupeptin, 1 mM antipain, and 0.1 mM sodium orthovanadate were added, 137 mM NaCl, 2 mM EDTA, and 0.1% SDS. The content of protein was determined using DC assay kit (Bio-Rad, USA), and then SDS-PAGE was conducted by loading a given amount of protein on 0-15% polyacrylamide gel. Then protein was transferred to nitrocellulose membrane at 50 V, 350 mA for 5 hours. All of antibodies were used according to the manufacturer's instructions, and the protein bands were identified using enhanced chemiluminescence detection kit (Amersham Pharmacia Biotech, Buckinghamshire, UK).

Figure 6A:
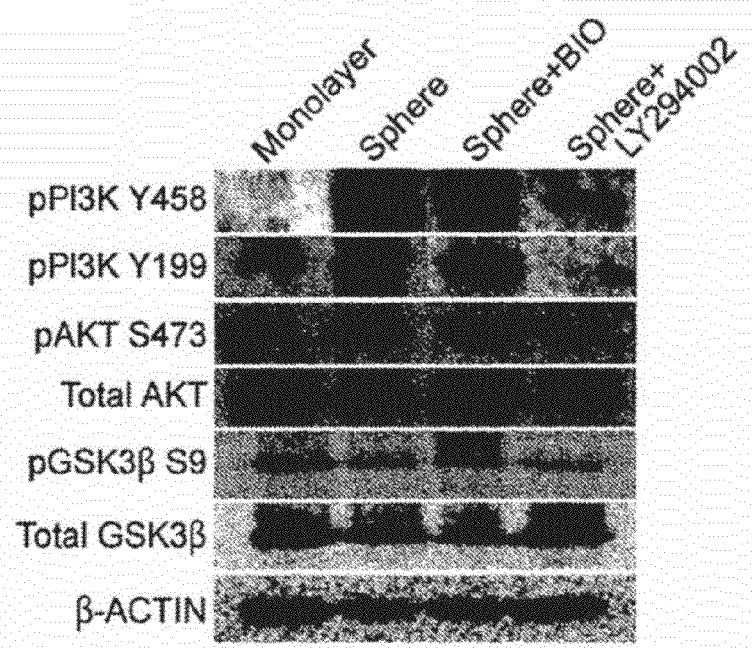
FIG. 6(A) is the result of Western blot analysis conducted after 7 days from sphere culture, wherein MSC spheres were collected by means of 40 μm strainer and then washed two times, and the phosphorylation levels of PI3K and its sequential downstream effectors, AKT and GSK3β were analyzed in monolayer cells, spheres, spheres treated with 0.2 μM BIO, and spheres treated with 30 μM LY294002.

As shown in FIG. 6A, as compared to monolayer-incubated adult stem cells, phospho-PI3K and phospho-AKT were increased in BIO-treated and -untreated adult stem cell spheres, but the treatment with LY294002 essentially caused dephosphorylation of GSK3β(Ser9) as the activated state.

Figure 6B:
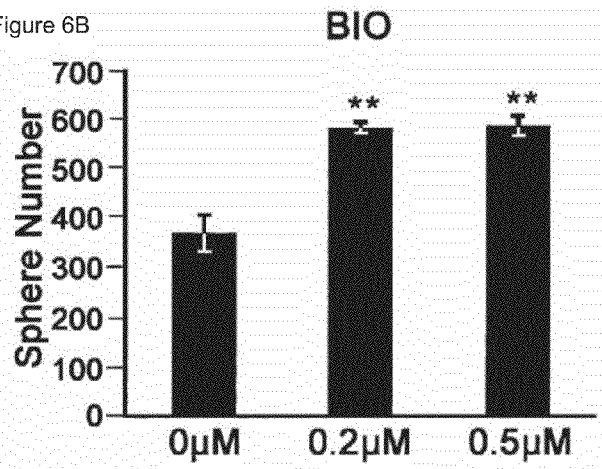
FIG. 6(B) shows the number of MSC spheres incubated in growth medium comprising 0 μM, 0.2 μM, or 0.5 μM of GSK3 inhibitor BIO (*, $P<0.05$; **, $P<0.01$).
Figure 6C:
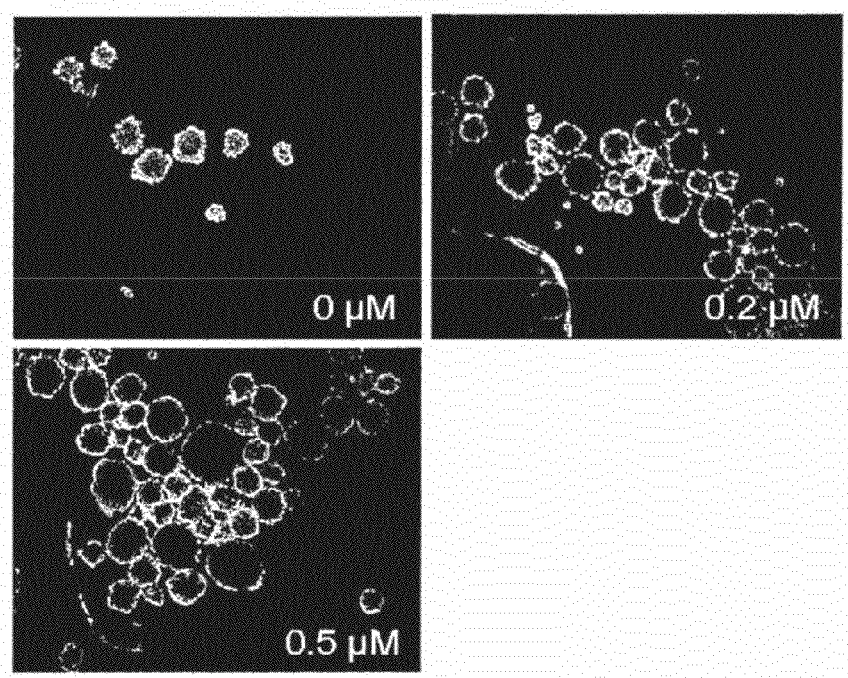
FIG. 6(C) shows phase contrast images of MSC spheres incubated in medium comprising the indicated concentration of BIO.
Figure 6D:
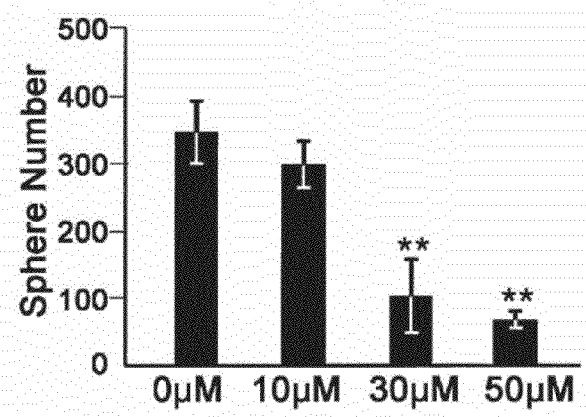
FIG. 6(D) shows the number of MSC spheres incubated in growth medium comprising 0 μM, 10 μM, 30 μM, or 50 μM of PI3K inhibitor LY294002 (*, $P<0.05$; **, $P<0.01$).
Figure 6E:
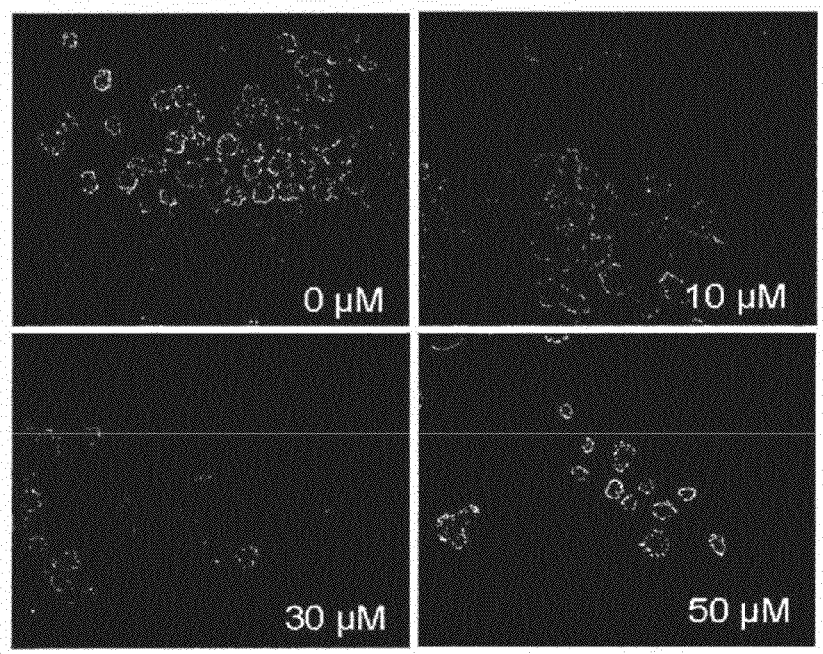
FIG. 6(E) shows phase contrast images of MSC spheres incubated in medium comprising the indicated concentration of LY294002.

Subsequently, the efficiencies of sphere formation after treatment with BIO or LY294002 were determined to identify whether PI3K/AKT/GSK3β pathway is related to the formation of adult stem cell spheres. After 7 days, in the group treated with BIO at the concentration of 0.2 μM to 0.5 μM the number of spheres as formed as well as the size of spheres was significantly increased, suggesting that GSK3β activity is inhibitory to sphere formation (FIGS. 6B and 6C). On the other hand, in the group treated with LY294002 at the concentration of 30 μM to 50 μM the number and size of adult stem cell spheres were significantly decreased (FIGS. 6D and 6E). Such results, together with this, suggest that PI3K/AKT/GSK3β signal transduction pathway is essential for sphere formation, and promotes the anchorage-independent survival.

Experiment 6

Change in Expression of Surface Markers of Spheres Derived from Adult Stem Cells To quantitatively analyze the expression of surface markers from monolayer-incubated cells (Comparative Example 1) and sphere-derived cells (Example 1), respective cells were collected by centrifugation, and then stained with CD49a-PE, CD49b-PE, CD49f-FITC, CD49e-PE, CD104-PE (BD Bioscience, San Jose, Calif., USA) as monoclonal mouse anti-human fluorochrome-conjugated antibodies to conduct the analysis for surface markers of cells using FACSAria (BD Bioscience, San Jose, Calif., USA) and FACSDiva software (BD Bioscience, San Jose, Calif., USA).

From the result of said FACS analysis, it was identified that sphere-derived cells (Example 1) exhibit higher expression of CD49f and CD104 as compared to monolayer-incubated cells (Comparative Example 1) (FIG. 7). Said experiment was repeated three times under the same conditions, and the result was derived from the mean value thereof.

Experiment 7

Upregulation of CD49F Contributes to the Formation of Adult Stem Cell Spheres Through Phosphorylation of FAK/Paxillin Integrins are one of important molecules, which interact with extracellular matrix, and initiate the survival- and growth-related signal transduction pathway such as PI3K/AKT through local protein kinases including FAK and Paxillin. Accordingly, both of monolayer-incubated adult stem cells (Comparative Example 1) and sphere-derived adult stem cells (Example 1) were subjected to FACS analysis to identify the expression profile of integrins.

The immunocytochemical analysis for CD49f was conducted as follows. The monolayer-incubated cells and sphere-derived MSCs were fixed in 4% paraformaldehyde, and then permeated with 0.2% Triton X-100 (Sigma Aldrich, USA). Cells were incubated together with 10% normal goat serum (Zymed Laboratories Inc., USA), labeled with primary antibody, and then incubated together with Alexa 488-labeled secondary antibody (1:1000; Molecular Probes, USA) for one hour. Nucleus was stained with Hoechst 33258 (1 μg/ml; 10 min). Cell images were captured with confocal microscope (Nikon, Eclipse TE200, Japan).

Figure 8A:
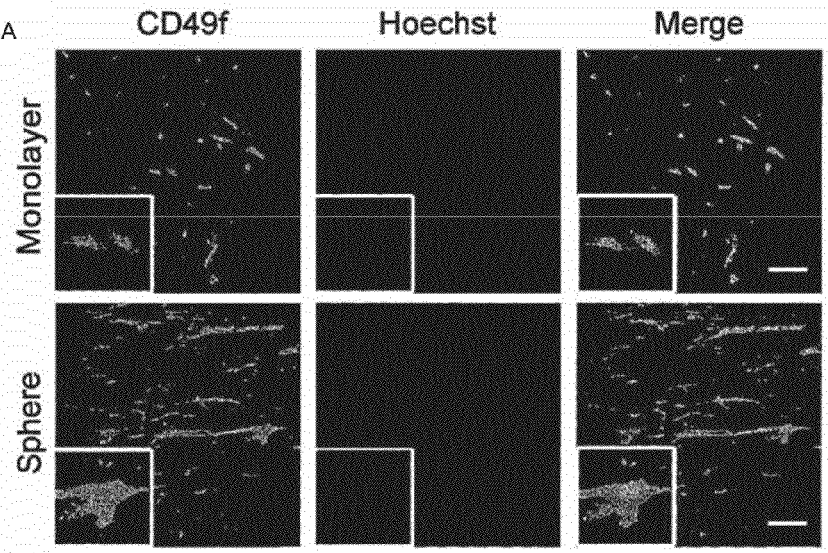
FIG. 8(A) shows the result from immunocytochemical analysis of CD49f expression in monolayer-incubated adult stem cells (Comparative Example 1) and sphere-derived adult stem cells (Example 1). Monolayer MSCs and isolated MSC spheres were seeded in 4-well chamber slide at the same starting number. After 3 days, cells were fixed and analyzed using the indicated antibodies. Scale bar=100 μm.
Figure 8B:
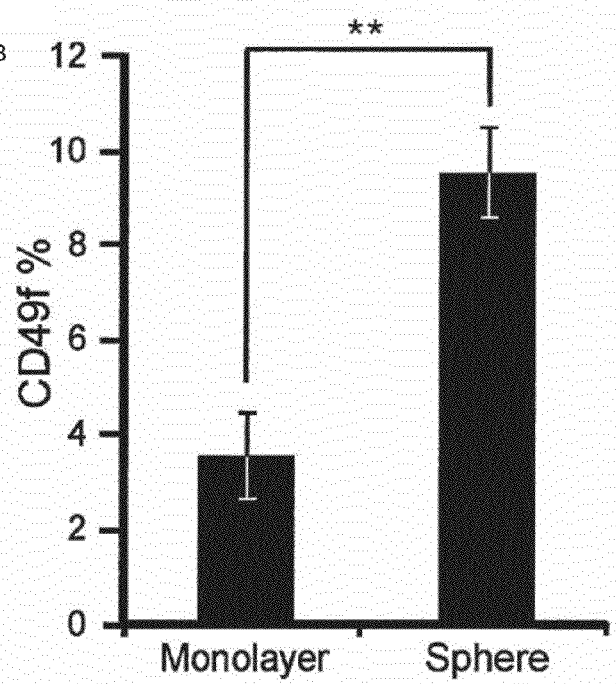
FIG. 8(B) shows the result obtained from FACS analysis of the expression level of CD49f by utilizing FITC-conjugated antibody. Measurement was repeated three times (*, $P<0.05$; **, $P<0.01$).
Figure 8C:
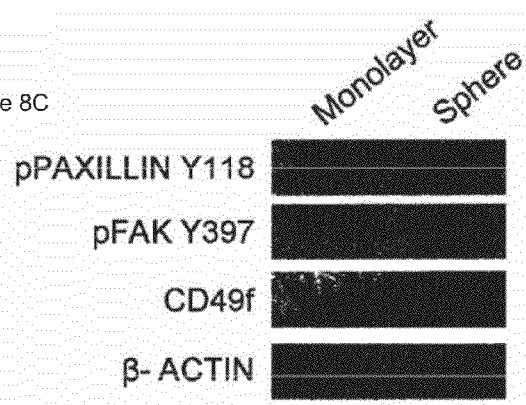
FIG. 8(C) shows the result obtained by identifying activities of downstream signal transducers of integrins such as FAK and PAXILLIN with Western blotting.

Although there was no significant difference in the expression levels of CD49a and CD49b between two conditions, CD49e was greatly decreased in MSC spheres. However, CD49f and CD104, which form a heterodimer, were upregulated in cells derived from adult stem cell spheres (FIG. 7, FIG. 8B). The frequency of CD49f-positive cells in adult stem cell spheres were higher by 167% as compared to adult stem cells grown in plastic culture plate. The result of immunocytochemistry was consistent with the result of FACS analysis. It was observed that as compared to monolayer-incubated (i.e. normal cultured) adult stem cells, sphere-derived adult stem cells exhibited an increase in CD49f expression and an increase in the number of cells positive for such marker (FIG. 8A). Through Western blot analysis, it was observed that in adult stem cell spheres the protein levels of phospho-Paxillin and phosphor-FAK were increased, and CD49f protein level was also increased (FIG. 8C).

Figure 8D:
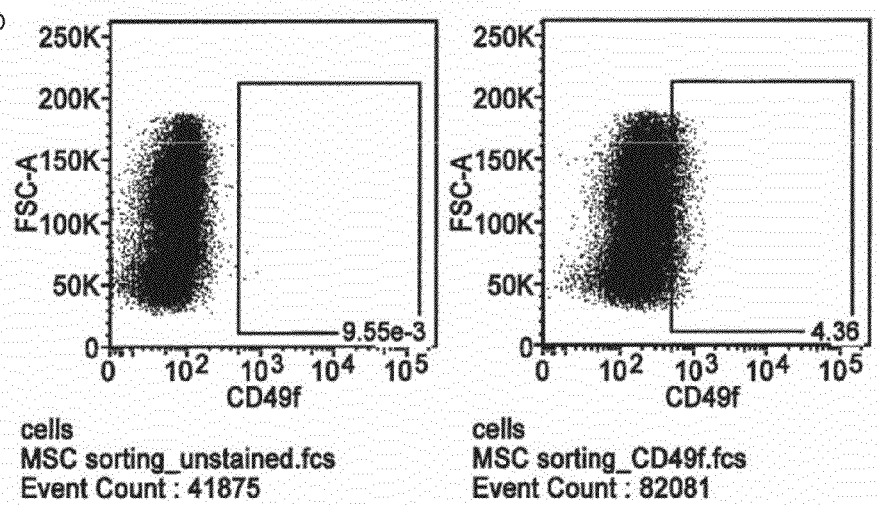
FIG. 8(D) shows the result of FACS sorting of adult stem cells into CD49f-negative and CD49f-positive cell populations.

Further, in order to identify whether the expression of integrins influences on the efficiency of spheres formation, CD49f-positive cell groups were gathered from whole MSC groups, and then subjected to FACS sorting on the basis of CD49f expression profile (FIG. 8D). hUCB-MSCs and adult stem cell spheres were collected, and then changed into single cells by utilizing trypsin-EDTA. Trypsinized cells were disposed in 5% FBS-added PBS for 10 minutes to re-express cell surface marker. Then, cells were collected by centrifugation and labeled with monoclonal mouse anti-human fluorochrome-conjugated antibodies (CD49a-PE, CD49b-PE, CD49f-FITC, CD49e-PE, CD104-PE, CD34-FITC, and CD44-FITC, all from BD Bioscience, San Jose, Calif.; CD90-Alexa Fluor 647 and CD117-PE, both from BioLegend). The labeled cells were sorted and analyzed by means of fluorescence-activated cell sorter, FACSAria (BD Biosciences), utilizing FACSDiva software (BD Biosciences).

The expression levels of OCT4, C-MYC, CD49b, CD49f, Paxillin, FAK and ILK, which are involved in integrin signaling, were determined by RT-PCR.

Figure 8G:
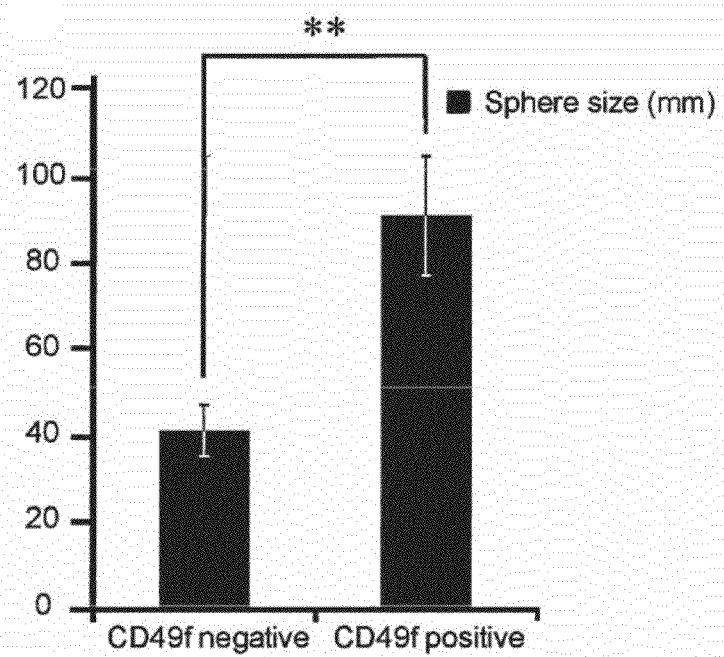
FIG. 8(G) is the result of measuring a size of spheres in CD49f-negative and -positive cell groups. To measure the sphere-size, 15 spheres were randomly selected and statistically analyzed (*, $P<0.05$; **, $P<0.01$).
Figure 8H:
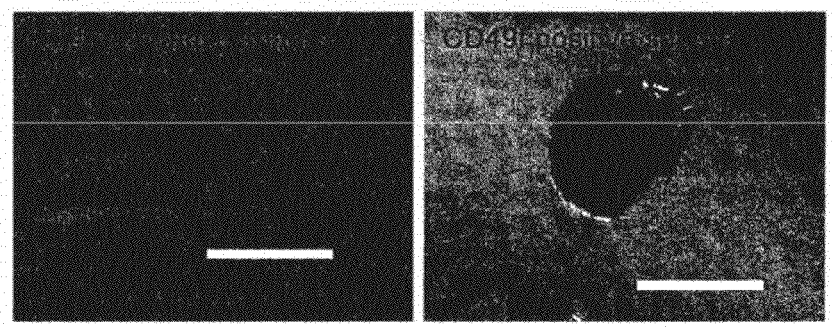
FIG. 8(H) shows phase contrast image of the representative one of spheres derived from CD49f-negative or -positive cells.

The mRNA levels of Paxillin, FAK and ILK as downstream tyrosine kinases of integrins were increased in CD49f-positive cell groups (FIG. 8E). CD49f-positive cells were more efficient for sphere formation, and exhibited an increase of sphere diameter by about 2.2 times as compared to sphere diameter of CD49f-negative cells (FIGS. 8F, 8G and 8H). From such results, it could be deduced that an increase in CD49f expression level is related to the activation of integrin signals, and allows adult stem cells to survive in anchorage-independent growth.

Experiment 8

Overexpression of CD49f Regulates Cell Proliferation and Differentiation by Activating PI3K/AKT/GSK3 Pathway In order to further confirm whether CD49f genetic expression is dependent on the activation of PI3K/AKT/GSK3 pathway, adult stem cells overexpressing CD49f were treated with LY294002 or BIO for 24 hours and 48 hours.

The proliferation potential of cells was measured by MTT assay analysis based on the ability of living cells to convert tetrazolium salt into purple formazan. Adult stem cells were transduced with either control vector or CD49f expression vector. After 24 hours from transduction, cells were seeded onto 24-well plate, and incubated in medium comprising LY294002 and BIO. After culture for 24 hours and 48 hours, 50 ml of MTT stock solution (5 mg/ml, Sigma) was added to each well, and then further incubated at 37° C. for 4 hours. After removing the supernatant, 200 ml of DMSO was added to each well so that insoluble purple formazan crystals can be dissolved in water. Then, cells were transferred to 96-well microplate and then the absorbance was measured using EL800 microplate reader (BIO-TEK Instruments, Winooski, Vt., U.S.A.) at wavelength of 540 nm. All of measurements were repeated three times.

In adult stem cells overexpressing CD49f, it was identified through MTT analysis that the growth rate in BIO-treated adult stem cells was higher than in adult stem cells not treated with BIO, but LY294002 inhibited cell proliferation (FIG. 9A). Consistently with this, in the assay for sphere formation BIO increased the number of adult stem cell spheres but LY294002 inhibited the sphere formation of adult stem cells overexpressing CD49f (FIG. 9B). Through Western blot analysis it was demonstrated that CD49f overexpression induced an increase in phosphorylation levels of PI3K, AKT and GSK3β in adult stem cells. BIO treatment induced phosphorylation of AKT and GSK3, whereas LY294002 treatment inhibited AKT phosphorylation in adult stem cells overexpressing CD49f (FIG. 9C). From such data, it could be deduced that upregulation of CD49f utilizes PI3K/AKT/GSK3 pathway in mediating cell proliferation.

Subsequently, whether in differentiation of adult stem cells into osteocytes and adipocytes CD49f expression can be regulated by PI3K/AKT/GSK3 pathway was identified. CD49f-overexpressed adult stem cells were treated with LY294002 and BIO, and then incubated in osteocyte and adipocyte media, respectively, to induce differentiation into osteogenic and adipogenic lineages.

Figure 10A:
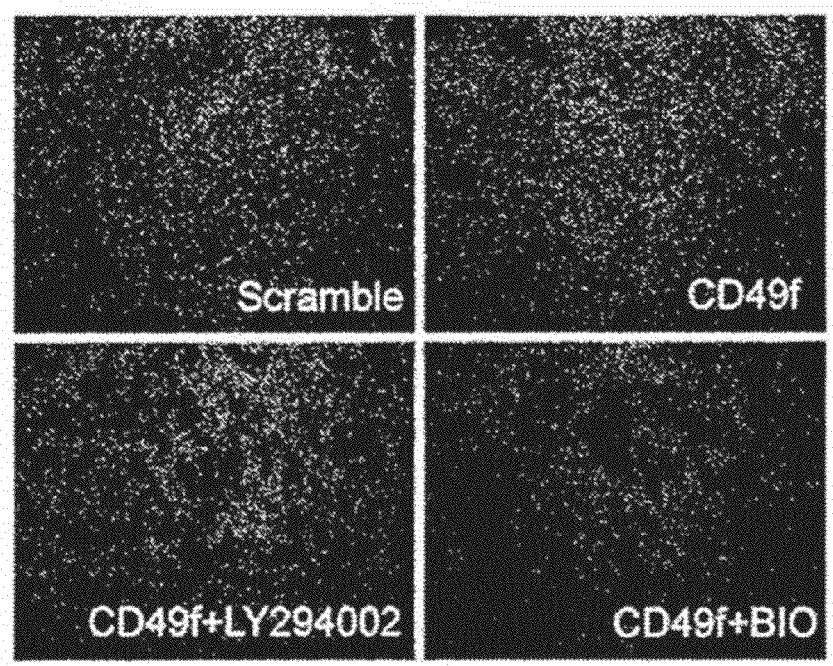
FIG. 10(A) shows the culture of adult stem cells in osteogenic conditioned media in the presence or absence of CD49f, LY294002, BIO. Osteogenesis was confirmed through Alizarin Red S staining.

Through Alizarin Red Staining, it was identified that CD49f increased mineral accumulation in osteocyte-induced cells and BIO treatment further increased mineral accumulation in CD49f-overexpressed MSCs, whereas LY294002 treatment significantly decreased the level of mineral accumulation in CD49f-overexpressed MSCs (FIGS. 10A and 10B). Consistently with this, it could be identified through RT-PCR that mRNA levels of BGLAP, VDR, MSX2, OSTEOCALCIN and RUNX2 as osteocyte-specific markers were increased by CD49f overexpression, and further increased in BIO-treated adult stem cells, but in case of LY294002 treatment mRNA levels of osteocyte-specific markers were decreased (FIG. 10C).

With respect to differentiation into adipocytes, it was identified through Oil Red 0 staining that lipid level was significantly increased in CD49f-overexpressed cells, but BIO and LY294002 inhibited lipid accumulation as compared to untreated control group (FIGS. 10D and 10E). In RT-PCR, mRNA levels of C/EBP β, aP2, PPARγ, and LEPTIN as major adipocyte transcription factors increased under CD49f overexpression, but BIO and LY294002 inhibited mRNA levels of adipocyte transcription factors (FIG. 10F). From such data, it could be known that upregulation of PI3K/AKT/GSK3 pathway promotes differentiation into osteocytes more specifically than differentiation into adipocytes in CD49f-overexpressed adult stem cells.

Experiment 9

OCT4 and SOX2 are Bound to CD49f, and Regulate CD49f Transcription Through CD49f Promoter Domain Since it was identified that CD49f expression is related to upregulation of integrin signals during formation of adult stem cell spheres, the present inventors examined whether CD49f is essential for the pluripotency of stem cells.

Total RNA was extracted using TRIzol™ reagent (Invitrogen) according to the manufacturer's instructions, and mixed with oligo-dT primers. And cDNA was synthesized from the mixture by utilizing SuperScript iii First-Strand Synthesis System (Invitrogen) for RT-PCR according to the manufacturer's instructions. Accupower PCR premix (Bioneer, Daejeon, Republic of Korea) was used to conduct PCR. Primer sets used in this study are listed in Table 1. All of PCR products were analyzed with gel electrophoresis through 1.5% agarose gel and ethidium bromide staining, and subjected to fluorescence digitization by means of Bio-Rad GelDoc XR system (Bio-Rad). cDNAs were mixed with primers relevant for each one and SYBR Green PCR Master Mix (Applied Biosystems, Foster City, Calif.) to conduct real-time PCR. The expression of genes was quantified by means of the given software (Applied Biosystems) and ABI 7300 sequence detection system according to the manufacturer's instructions. Respective genes were normalized with β-actin or RPL13A as the housekeeping control. The experiments were repeatedly conducted at least three times for respective genes.

Figure 11A:
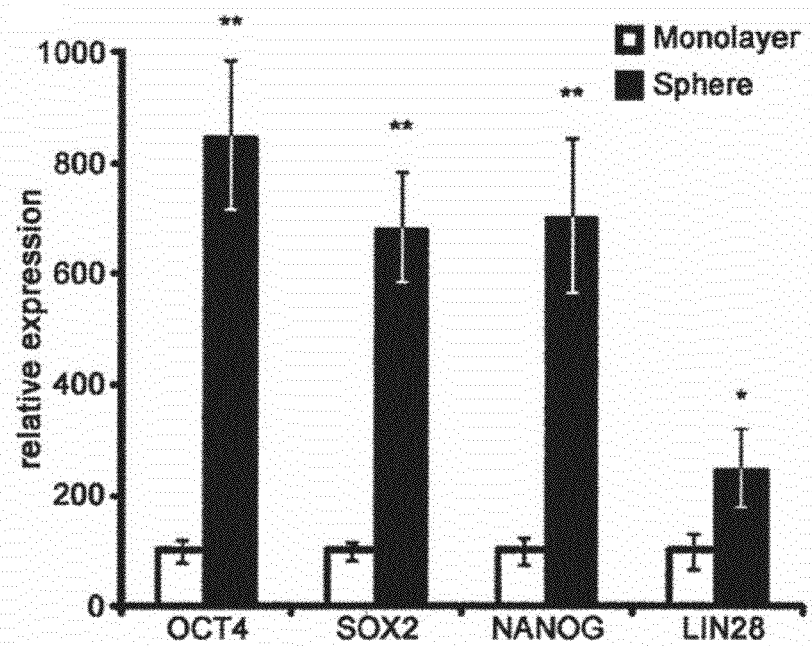
FIG. 11(A) shows the result obtained by quantitatively measuring mRNA expression by means of real-time PCR. In this figure, relative mRNA expression levels of pluripotent markers in monolayer cells (Comparative Example 1) and MSC spheres (Example 1) are presented. All of the analyses were repeated three times, and then normalized with intrinsic β-ACTIN (*, P<0.05; **, P<0.01).

First, the expression of pluripotent markers was identified in adult stem cell spheres. mRNA levels of OCT4, SOX2, NANOG and LIN28, which can reprogram human somatic cells to pluripotent stem cells, were increased in adult stem cell spheres as compared to monolayer-incubated adult stem cells (FIG. 11A).

To identify whether OCT4 and SOX2 have influence on CD49f, siOCT4 and siSOX2 were transduced into adult stem cells.

To specifically inhibit OCT4, SOX2 and CD49f commercial siRNAs targeted to OCT4, SOX2, and CD49f (Dharmacon, ON Target plus SMART pool, OCT4: Cat #L-019591-00, SOX2: Cat #L-011778-00, CD49f: Cat# L-007214-00-0005) and non-targeting siRNAs (Dharmacon, ON Target plus SMART pool, Cat #D-001810-01) were used to conduct siRNA knockdown study. siRNAs were transduced according to the manufacturer's instructions. In brief, cells were seeded at the level of 5×10⁴/well, and when cells reached 50% confluence, siRNA-comprising medium (no antibiotics) was added. Cells were incubated with 100 nM siRNA for 48 hours to enhance mRNA expression, and for 72 hours to enhance protein expression, and then RNA and protein were extracted for analysis of genes and proteins.

Figure 11B:
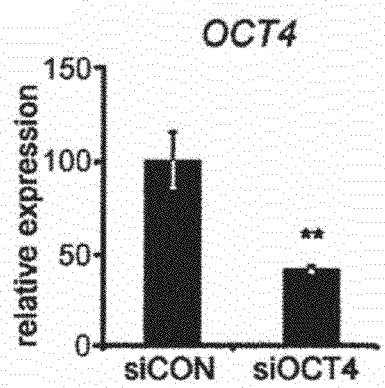
FIG. 11(B, C) shows the result obtained by transfecting siRNAs targeted to OCT4 or SOX2 into adult stem cells and analyzing the expression levels of OCT4 and SOX2 via real-time PCR (*, P<0.05; **, P<0.01). Non-targeted siRNA (siCON) was used as the control group.
FIG. 11(D) shows the result obtained by collecting cells after 48 hours from transduction and then identifying the expression o CD49f via real-time PCR.
FIG. 11(E) shows the sphere-forming efficiency as measured in siRNA-transfected cells and control-transduced cells (*, P<0.05; **, P<0.01).
FIG. 11(F) shows the result of chromatin immunoprecipitation using anti-OCT4, anti-SOX2 antibodies. Specific primer sets targeted to three domains of CD49f promoter are listed in Table 1.
FIG. 11(G) shows the result of immunocytochemical analysis of CD49f, OCT4, SOX2 in cells infected with control virus and OCT4, SOX2 viruses. Nuclei were stained with Hoechst (Blue). Scale bar=50 μm.
FIG. 11(H) shows the CD49f-positive cell groups in the control group and cells in which OCT4 and SOX2 are overexpressed, as identified by FACS.
FIG. 11(I) shows the result obtained by quantitatively measuring the expression of CD49f mRNA as compared to the control group. The combination of cells in which OCT4, SOX2, LIN28, NANOG were overexpressed is indicated.
FIG. 11(J) shows the result of Western blotting for identifying CD49f protein expression in the indicated combination of cells infected with virus.
Figure 11C:
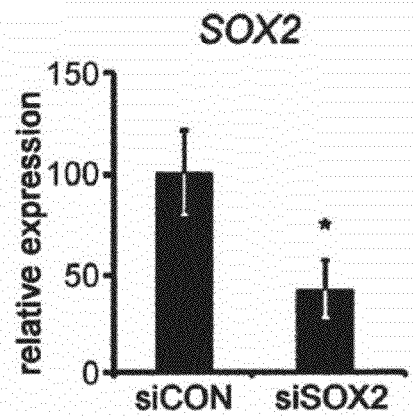
Figure 11D:
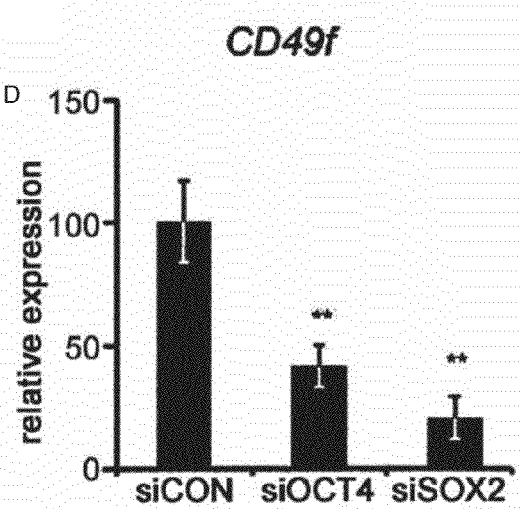
Figure 11E:
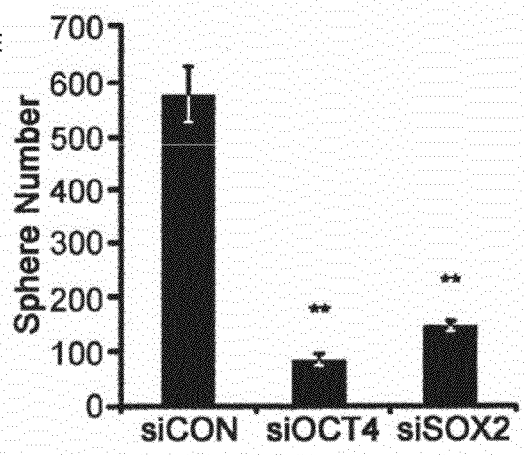

OCT4 and SOX2 siRNA treatment specifically blocked the expression of OCT4 and SOX2 mRNAs (FIGS. 11B and 11C). Further, siRNAs targeted to OCT4 and SOX2 significantly downregulated the expression of CD49f mRNAs, and decreased the number of adult stem cell spheres, as identified through the analysis of sphere formation (FIGS. 11D and 11E). To confirm how OCT and SOX2 regulate CD49f expression adult stem cells were infected with lentivirus overexpressing OCT4 and SOX2, and then the expression of OCT4, SOX2 and CD49f was identified through immunocytochemistry. When both of OCT4 and SOX2 were overexpressed, CD49f expression was increased (FIG. 11G). Overexpression of CD49f in adult stem cells was also identified at the protein level through FACS analysis.

Figure 11F:
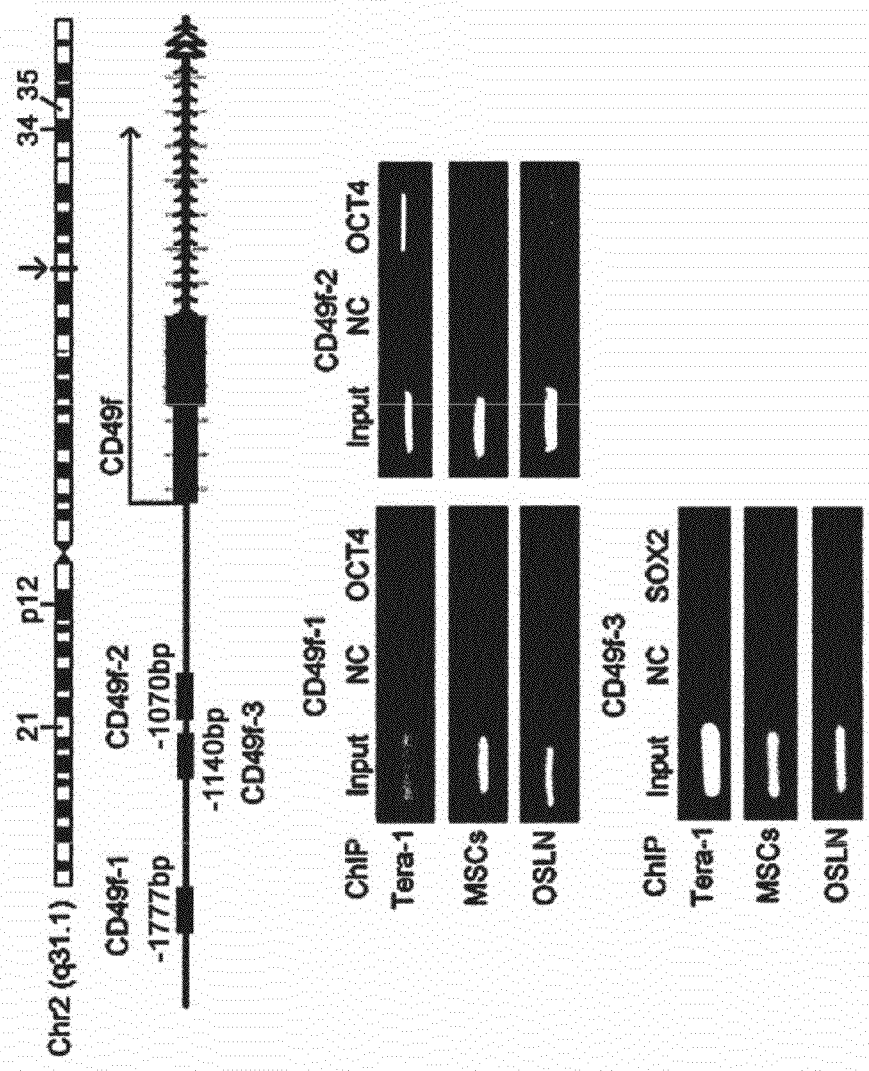
Figure 11H:
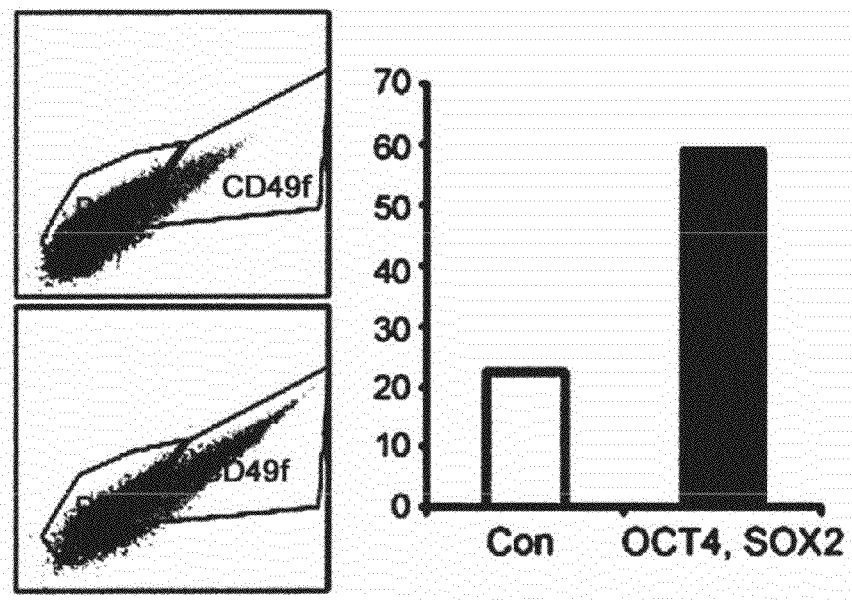
Figure 11I:
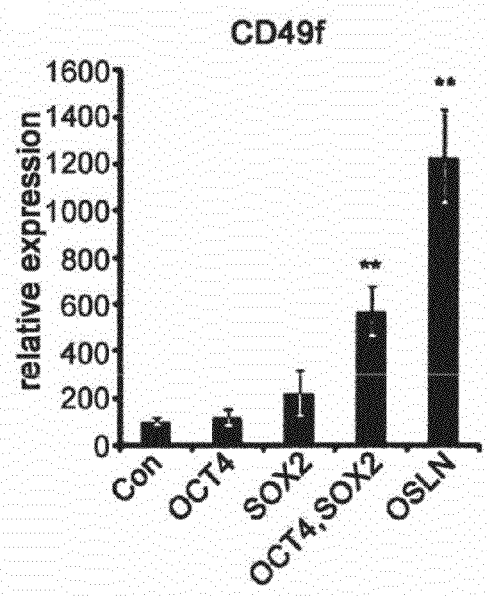
Figure 11J:
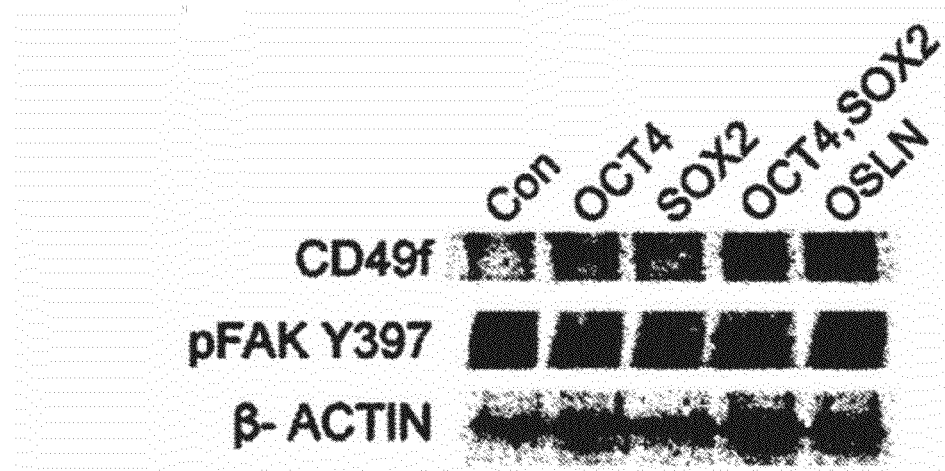

As shown in FIG. 11H, when OCT4 and SOX2 were overexpressed, CD49f-positive sub-population was increased. To confirm how the activity of OCT4 and SOX2 can regulate CD49f expression, antibodies specific to OCT4 and SOX2 were used to conduct ChIP for CD49 promoter site. Fragmented DNAs bound to antibodies were used for RT-PCR, wherein primers designed to be targeted to CD49f promoter site were also used. As shown in FIG. 11F, a certain domain in CD49f promoter was increased together with OCT4 and SOX2 proteins, suggesting that OCT4 and SOX2 bind to CD49f promoters and activate the expression of CD49f. Subsequently, the experiment was conducted to identify whether CD49f expression in adult stem cells can be regulated by OCT4, SOX2, LIN28 and NANOG. Adult stem cells were infected with lentivirus for OCT4, SOX2, LIN28 and NANOG, and mRNA level of CD49f was identified using real-time PCR. When OCT4/SOX2 or OCT4/SOX2/LIN28/NANOG were overexpressed, mRNA level of CD49f was significantly increased (FIG. 11H). According to Western blot analysis, protein level of CD49f and phosphorylation of FAK in adult stem cells were increased together with overexpression of Oct4/Sox2 or OCT4/SOX2/LIN28/NANOG (FIG. 11I). Accordingly, such data suggest that OCT4, SOX2, LIN28 and NANOG have a positive feedback loop, which improves integrin signal pathway in adult stem cells.

TABLE 1

| Gene name | Primer sequence |
|---|---|
| | Names and sequences of the primers for RT-PCR and qRT-PCR assays |
| β-ACTIN | Forward: AGA GCT ACG AGC TGC CTG AC |
| | Reverse: AGC ACT GTG TTG GCG TAC AG |
| C/EBP-β | Forward: GCG CGC TTA CCT CGG CTA CC |
| | Reverse: TGG CCT TGT CGC GGC TCT TG |
| AP2 | Forward: GGG TCA CAG CAC CCT CCT GA |
| | Reverse: GGT TTG GCC ATG CCA GCC AC |
| PPAR-γ | Forward: CCT CCG GGC CCT GGC AAA AC |
| | Reverse: CTC CTG CAC AGC CTC CAC GG |
| LEPTIN | Forward: GAA GAC CAC ATC CAC ACA CG |
| | Reverse: AGC TCA GCC AGA CCC ATC TA |
| OSTEOCALCIN | Forward: CCT ATT GGC CCT GGC CGC AC |
| | Reverse: GAC ACC CTA GAC CGG GCC GT |
| RUNX2 | Forward: CTT GAC CAT AAC CGT CTT CA |
| | Reverse: GTC ATC AAT CTT CTG TCT GT |
| Paxillin | Forward: AAC TGG TTG AAG GGT GTT GC |
| | Reverse: AGG TTC AGT GGG TTC ACA GG |
| FAK | Forward: CGA GAG ATT GAG ATG GCA CA |
| | Reverse: TAC TCT TGC TGG AGG CTG GT |
| ILK | Forward: AAG GTG CTG AAG GTT CGA GA |
| | Reverse: ATA CGG CAT CCA GTG TGT GA |
| VDR | Forward: CGG CCG GAC CAG AAG CCT TT |
| | Reverse: CTG GCA GTG GCG TCG GTT GT |
| MSX2 | Forward: CCC TGG AGC GCA AGT TCC GT |
| | Reverse: GGC GGG ATG GGA AGC ACA GG |
| CD49f | Forward: TCA TGG ATC TGC AAA TGG AA |
| | Reverse: AGG GAA CCA ACA GCA ACA TC |
| OCT4 | Forward: GTG GAG GAA GCT GAC AAC AA |
| | Reverse: ATT CTC CAG GTT GCC TCT CA |
| SOX2 | Forward: TGG CGA ACC ATC TCT GTG GT |
| | Reverse: CCA ACG GTG TCA ACC TGC AT |
| LIN28 | Forward: GGG GAA TCA CCC TAC AAC CT |
| | Reverse: CTT GGC TCC ATG AAT CTG GT |
| NANOG | Forward: ACC TTG GCT GCC GTC TCT GG |
| | Reverse: AGC AAA GCC TCC CAA TCC CAA |
| CMYC | Forward: AAG ACA GCG GCA GCC CGA AC |
| | Reverse: TGG GCG AGC TGC TGT CGT TG |
| KLF4 | Forward: GGC TGC ACA CGA CTT CCC CC |
| | Reverse: GGT GGC GGT CCT TTT CCG GG |
| CK18 | Forward: AAT GGG AGG CAT CCA GAA CGA GAA |
| | Reverse: GGG CAT TGT CCA CAG TAT TTG CGA |
| FOXA2 | Forward: TGG GAG GCG GTG AAG ATG GA |
| | Reverse: TCA TGC CAG CGC CCA CGT AC |
| PEPCK | Forward: TTA GAT GGG ACA AAG CCT G |
| | Reverse: GCA AGA CGG TGA TTG TAA CT |
| HNF4a | Forward: GGA ACA TAT GGG AAC CAA CG |
| | Reverse: AAC TTC CTG CTT GGT GAT GG |
| AFP | Forward: GAA TGC TGC AAA CTG ACC AC |
| | Reverse: TGG CAT TCA AGA GGG TTT TC |
| TUJ-1 | Forward: CAG TGA CCT GCA ACT GGA GA |
| | Reverse: GAT TGG CCA AAC ACG AAG TT |
| MUSASHI | Forward: GCC CAA GAT GGT GAC TCG |
| | Reverse: ATG GCG TCG TCC ACC TTC |
| NESTIN | Forward: AAC AGC GAC GGA CTG TCT CTA |
| | Reverse: TTC TCT TGT CCC GCA GAC TT |

TABLE 1-continued

| Gene name | Primer sequence |
|---|---|
| MAP2 | Forward: CCA ATG GAT TCC CAT ACA GG |
| | Reverse: TCT CCG TTG ATC CCA TTC TC |
| PAX6 | Forward: ACC CAT TAT CCA GAT GTG TT |
| | Reverse: ATG GTG AAG CTG GGC ATA GG |
| MSX1 | Forward: CGA GAG GAC CCC GTG GAT GC |
| | Reverse: GGC GGC CAT CTT CAG CTT CT |
| BRACHYURY | Forward: GCC CTC TCC CTC CCC CTC CAC |
| | Reverse: GGC GCC GTT GCT CAC AGA CC |
| Col 1A2 | Forward: CTG GTG CTG CTG GCC GAG TC |
| | Reverse: GGG ACC AGG GGG ACC ACG TT |

Names and sequences of the primers for ChIP assays

| | |
|---|---|
| CD49f primer-1 | Forward: AGAACAACGGGCTCATTCAG |
| | Reverse: CGACAGGTAGAGCAAGCACA |
| CD49f primer-2 | Forward: TAGGAAAGAACGGCATCGTC |
| | Reverse: CTAGGATTTTGCCCAGGTGA |
| CD49f primer-3 | Forward: AACCCCTGCAGGATAAGGTT |
| | Reverse: AGTTGTGGGGAGAACTGCTG |
| CD49f primer-4 | Forward: TGATGTTCACGCAGCTTTTC |
| | Reverse: GGAATCTGACATCCCTGCAT |
| CD49f primer-5 | Forward: ACATGGGGATATCCAAGCAG |
| | Reverse: TGCCCTTAGTTCCTCACAGG |
| CD49f primer-6 | Forward: CTGGCCAAAACTTGATGGTT |
| | Reverse: CCATCGCAAATGGAAAACTT |

Experiment 10

CD49f Maintains the Pluripotency of iPSCs and hESCs Through PI3K/AKT/GSK3β Pathway Because it was identified that CD49f is closely related to pluripotent markers, the role of CD49f was examined in stem cells in the state of pluripotency.

Adult stem cells were infected with lentivirus (virus produced from plasmids pSin-EF2-Oct4-Pur, pSin-EF2-Sox2-Pur, pSin-EF2-Nanog-Pur and pSin-EF2-Lin28-Pur13 of Addgene (Cambridge, USA)), which expresses OCT4, SOX2, LIN28 and NANOG efficient for reprogramming of human fibroblasts to pluripotent stem cells.

The viral production and transduction process were conducted as described in the reference (Yu et al., (2007), Induced pluripotent stem cell lines derived from human somatic cells. Science 318, 1917-1920).

Figure 12:
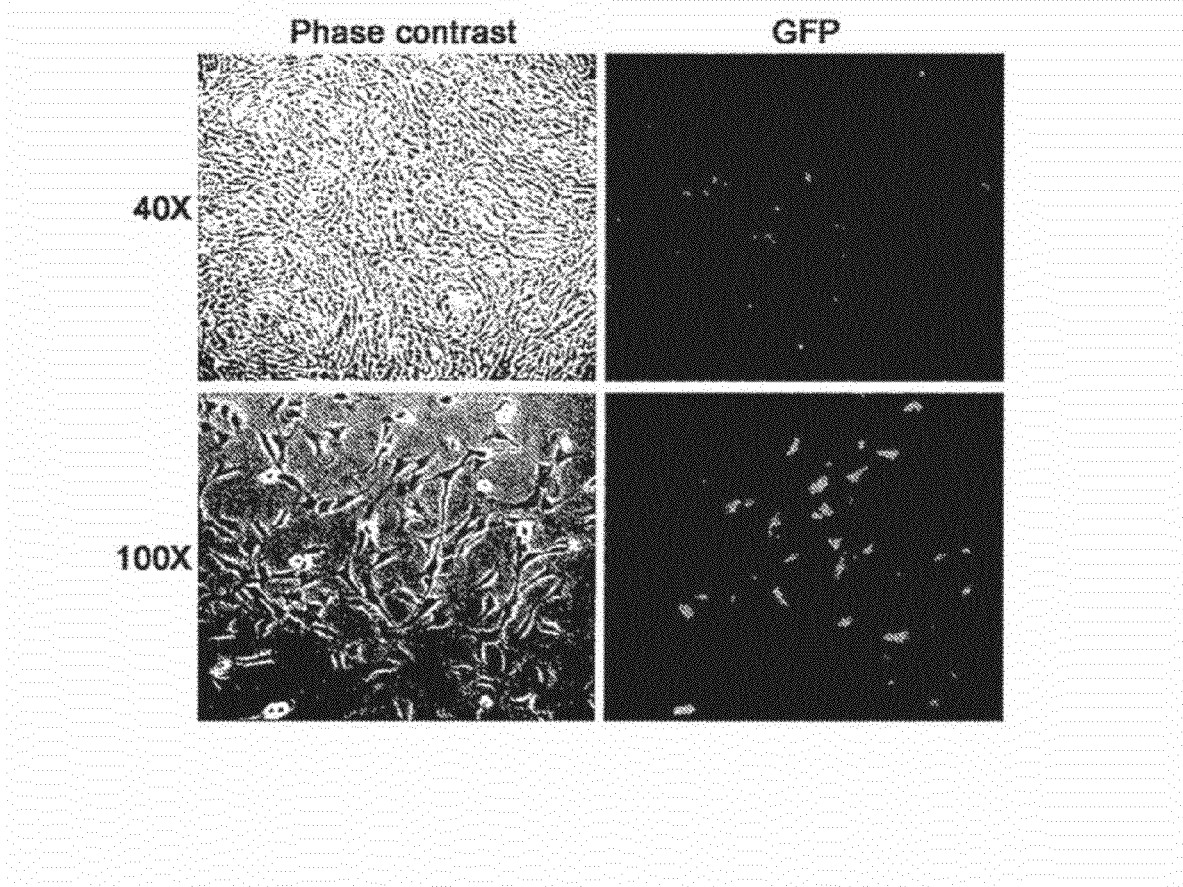
FIG. 12 shows the virus infection efficiency as determined by GFP expression. Sufficient infection efficiency is essential for production of iPSCs. The efficiency of signal transduction was determined using GFP virus.

To produce iPSCs the efficiency of infection using GFP virus must be at least 50%. It was observed that about 50% to 70% of total cells were GFP-positive cells (FIG. 12). Adult stem cells infected with OCT4/SOX2/LIN28/NANOG virus were transferred to hES medium comprising STO feeder cell.

Within 10 to 20 days hESC-like colonies appeared, and high level of alkaline phosphatase (AP) activity was observed. Two clones of minimally differentiated adult stem cell-derived iPSCs (induced pluripotent stem cells) were supplementarily analyzed. iPSCs displayed typical hESC colony morphology, and after additional expansion for 4 weeks displayed a positive reaction under AP staining. Adult stem cells infected only with OCT4 and SOX2 displayed week AP activity, but did not form ES-like colonies (FIG. 13A). To ascertain the pluripotency of iPSCs the analysis for teratoma formation was conducted.

Human iPS cells grown in STO feeder cells were collected, and then subcutaneously injected into non-obese diabetic-severe combined immunodeficient (NOD-SCID) mouse. After 6 to 8 weeks, teratoma was observed. Tumor samples were collected and subjected to paraffin embedding and Hematoxylin and Eosin staining according to the following standard procedures.

Figure 13B:
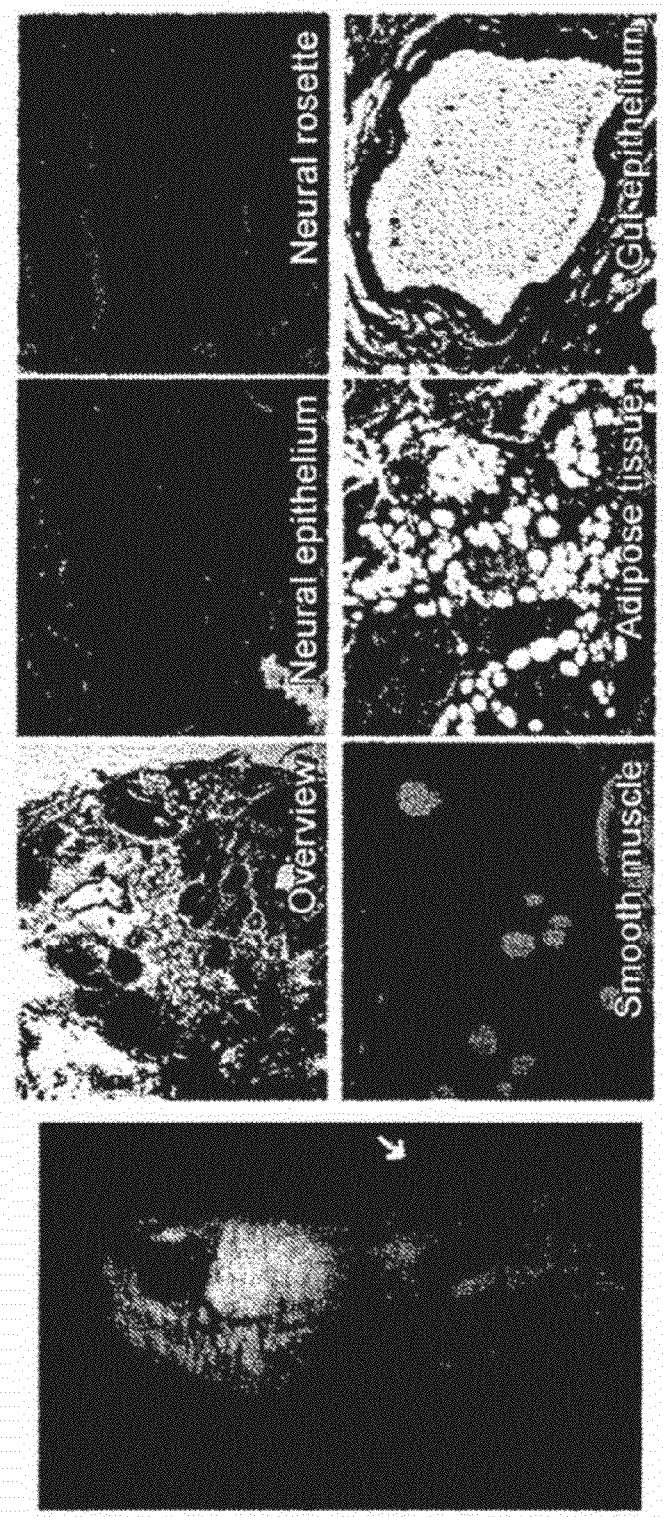
FIG. 13(B) shows the result of Hematoxylin and Eosin staining (H&E staining) of iPSCs-derived teratomas, which display the histological overviews of ectoderm (Neural epithelium, Neural rosette), mesoderm (Smooth muscle), and endoderm (Adipose tissue, Gut epithelium).
Figure 13C:
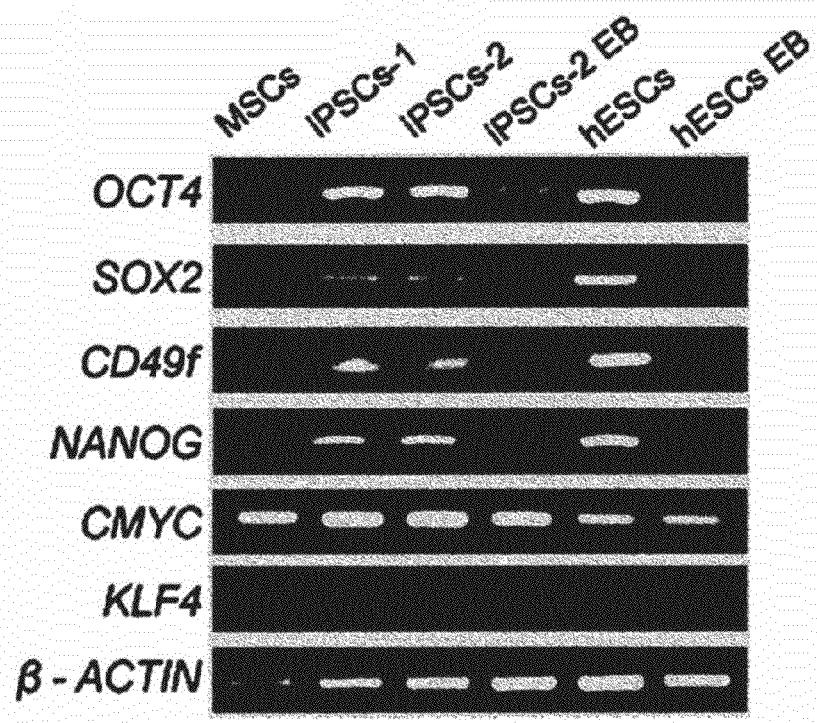
FIG. 13(C) shows the result obtained by analyzing the expression levels of pluripotent marker genes and CD49f, β-ACTIN by means of RT-PCR.

Through hematoxylin and eosin staining it was identified that cells were differentiated into representative tissues generated from embryonic germ layers, including neural epithelium, neural rosette, smooth muscle, adipose tissue and gut epithelium (FIG. 13B). It could be known from RT-PCR analysis that intrinsic mRNA expression levels of pluripotent marker genes such as OCT4, SOX2, NANOG and CD49f were similar to those of hESCs, and significantly increased as compared to parental adult stem cells. hESCs and hiPSCs were subjected to suspension-culture for 8 days to form embryoid bodies (EBs), and then supplementarily incubated for 8 days with adhering to gelatin-coated container for differentiation (FIG. 14A). The expression of pluripotent markers and CD49f was decreased during differentiation period, suggesting that CD49f expression is closely related to the pluripotentcy. To the contrary, CMYC and KLF4 expression was not influenced during differentiation period (FIG. 13C).

Figure 13E:
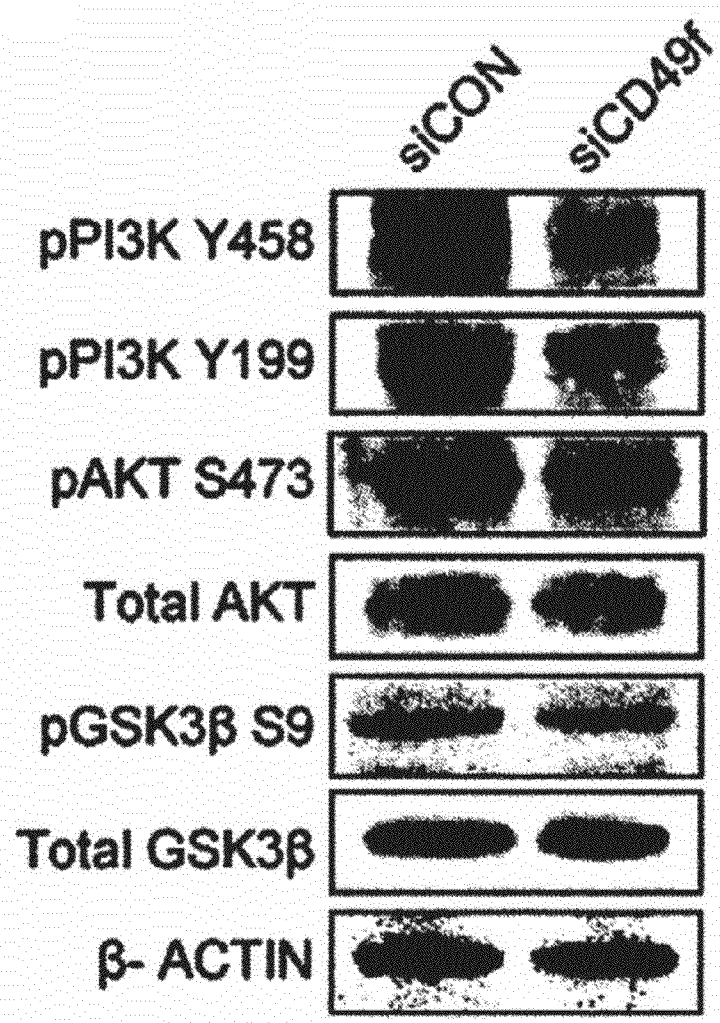
FIG. 13(E) shows the result obtained by transducing hESCs with non-targeted siRNA and CD49f-targeted siRNA, successively repeating said transduction three times, collecting the cell lysates, and then subjecting them to Western blot analysis for PI3K/AKT/GSK3β.
Figure 13F:
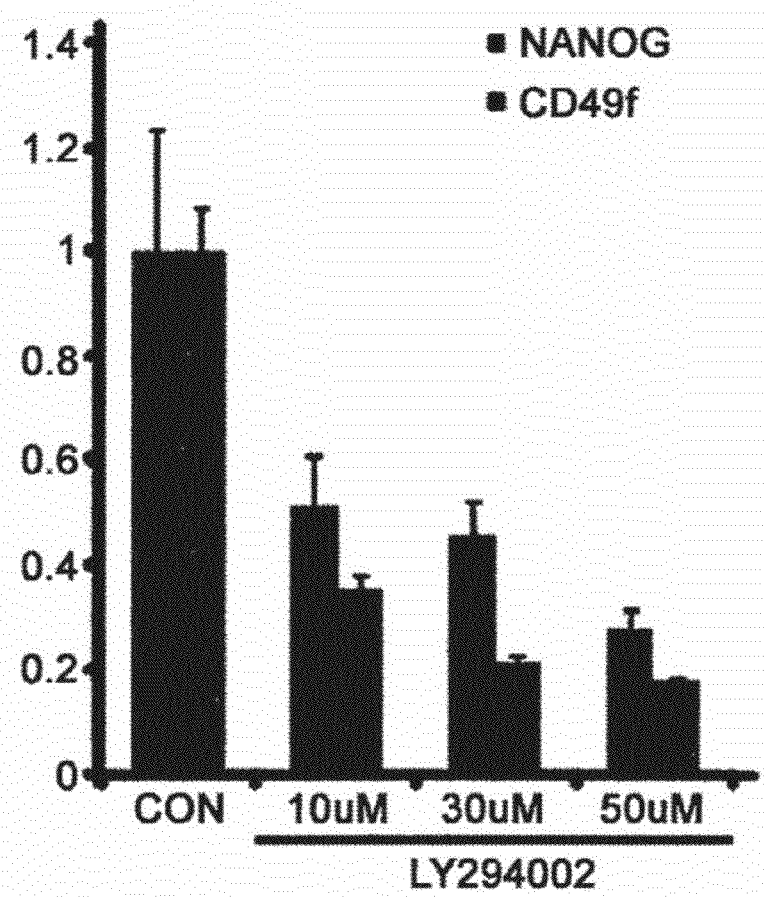
FIG. 13(F) shows the result obtained by treating hESCs with the indicated concentrations of PI3K inhibitor LY294002, and then measuring the expression of NANOG and CD49f by means of real-time PCR.

Subsequently, after inducing CD49f knockdown in hESCs the role of CD49f with respect to the pluripotency was examined. hESCs were transduced with 100 nM of siCD49f two times for 3 days, and subjected to RT-PCR to analyze pluripotent markers and system markers. siCD49f-transduced hESCs showed a partially differentiated form (FIG. 14B), and exhibited a significant decrease in pluripotent marker genes. Contrary to this, in hESCs into which siCD49f was transduced the system-specific marker genes were upregulated. This demonstrated that CD49f plays an important role in maintaining the pluripotency of hESCs (FIG. 13D). FIGS. 6 and 8 show that in adult stem cell spheres PI3K/AKT/GSK3β pathway is activated and CD49f-positive cell populations become abundant. Consistently with adult stem cell spheres, CD49f knockdown induced inhibition of PI3K/AKT/GSK3β pathway in hESCs (FIG. 13E). To supplementarily ascertain whether through PI3K pathway CD49f is necessary for maintaining the undifferentiated state of hESCs, cells were treated with LY294002 as a selective inhibitor of PI3K/AKT. PI3K/AKT inhibition significantly decreased the expression of both NANOG and CD49f (FIG. 13F). Such findings mean that CD49f contributes to reprogramming and maintenance of hiPSCs and hESCs through PI3K/AKT/GSK3β pathway.

Although specific portions of the present invention were specifically described in the above, by a person skilled in the art will apparently understand that such specific description is only preferable embodiments of the present invention, but the scope of the present invention is not limited by them. Accordingly, it should be understood that the practical scope of the present invention is defined only by the appended claims and equivalency thereof.

The invention claimed is:

1. A method for preparing adult stem cells, which express CD49f and exhibit an improved homogeneity as compared to pre-culture stem cells, comprising:
   (a) the first step of culturing adult stem cells in a growth medium comprising basic fibroblast growth factor (bFGF), insulin-like growth factor 1 (IGF-1) and epidermal growth factor (EGF), on an agar or agarose coated plate, wherein culturing of the cells increases the expression of at least one of OCT4, SOX2, LIN28, NANOG, and increases the expression level of CD49f, and thereby forming adult stem cell spheres; and
   (b) the second step of isolating adult stem cells from the adult stem cell spheres produced in (a), wherein the expression of CD49f maintains pluripotency or multipotency of said adult stem cells;
   thereby preparing adult stem cells which express CD49f and exhibit an improved homogeneity as compared to pre-culture stem cells.

2. A method for preparing homogeneous adult stem cells, comprising: (a) the first step of preparing a cell source comprising adult stem cells, wherein the prepared cells are cultured in a growth medium comprising basic fibroblast growth factor (bFGF), insulin-like growth factor 1 (IGF-1) and epidermal growth factor (EGF), on an agar or agarose coated plate, wherein culturing of the cells increases the expression of at least one of OCT4, SOX2, LIN28, NANOG, and increases the expression level of CD49f, and thereby forming adult stem cell spheres; and
   (b) the second step of isolating CD49f-positive adult stem cells from the adult stem spheres produced in (a).

3. The method according to claim 1, wherein after culturing the cells for one week in step (a), the number of adult stem cell spheres is 30 to 50 spheres per $1\times10^4$ cells, and the average diameter of spheres is 100 to 150 μm.

4. The method according to claim 1, wherein the isolated adult stem cells in step (b) exhibit a similar or increased expression level of CD49f as compared to adult stem cells cultured under adhesive culture conditions.

5. The method according to claim 1, characterized in that adult stem cells used in the first step are the adult stem cells with CD49f positive characteristics, which are isolated from a cell source.

6. The method according to claim 1, wherein the first and second steps are repeated 2 times or more, and the method further comprises the step of separating the adult stem cell spheres into single adult stem cells after the second step and before the repeated first step.

7. The method according to claim 1, wherein in the first step said cells are cultured by regulating PI3K/AKT/GSKβ so that said CD49F expression is maintained or further increased.

8. The method according to claim 1, wherein in the first step, the cells are cultured with the addition of a GSK3β inhibitor.

9. The method according to claim 1 or 2, characterized in that wherein the adult stem cells isolated from the second step have increased expression of OCT4, SOX2, or both, as compared to adult stem cells obtained by culturing the adult stem cells derived from the same cell source under adhesive culture conditions.

10. The method according to claim 1 or 2, wherein the isolation in step (b) uses antibodies which recognize surface antigens of CD49f.

11. The method according to claim 1, wherein expression of OCT4, SOX2, c-myc, paxillin, ilk, p13K and nanog is increased in the isolated adult stem cells of (b) as compared to the expression of the same protein in spindle-shaped adult stem cells obtained by culturing the adult stem cells derived from the same cell source under adhesive culture conditions.

12. The method according to claim 1, wherein the isolated adult stem cells of (b), express PI3K and GSK3β, wherein said PI3K and GSK3β are highly phosphorylated as compared to spindle-shaped adult stem cells obtained by culturing the adult stem cells derived from the same cell source under adhesive culture conditions.

13. A method for proliferating adult stem cells which express CD49f, comprising the step of culturing adult stem cells which express CD49f, prepared by the method according to claim 1 or 2.

14. The method for proliferating adult stem cells which express CD49f according to claim 13, wherein the adult stem cells are cultured in suspension culture or adhesive culture.

15. A method for preparing adult stem cells, which have CD49f-positive characteristics comprising:
  (a) plating adult stem cells on an agarose coated plate in a growth medium comprising basic fibroblast growth factor (bFGF), insulin-like growth factor 1 (IGF-1) and epidermal growth factor (EGF);
  (b) culturing the adult stem cells on said agarose coated plate in said growth medium for at least a week;
  (c) isolating and collecting the resultant adult stem cell spheres, wherein said adult stem cell spheres have increased expression of at least one of OCT4, SOX2, LIN28 and NANOG; and
  (d) further isolating CD49f-positive adult stem cells from the adult stem cell spheres of step (b), wherein the CD49f-positive cells exhibit an improved homogeneity as compared to pre-culture stem cells.

16. A method for preparing a homogeneous adult stem cell population, comprising:
  (a) plating adult stem cells on an agarose coated plate in a growth medium comprising basic fibroblast growth factor (bFGF), insulin-like growth factor 1 (IGF-1) and epidermal growth factor (EGF);
  (b) culturing the adult stem cells on said agarose coated plate in said growth medium for at least a week;
  (c) isolating and collecting the resultant adult stem cell spheres, wherein said adult stem cell spheres have increased expression of at least one of OCT4, SOX2, LIN28 and NANOG; and
  (d) further isolating CD49f- positive adult stem cells from the adult stem cell spheres, thereby forming a homogenous adult stem cell population.

* * * * *